US010702540B2

(12) United States Patent
Auerbach et al.

(10) Patent No.: US 10,702,540 B2
(45) Date of Patent: Jul. 7, 2020

(54) METHODS AND COMPOSITIONS FOR TREATING CANCER

(71) Applicant: Janssen Oncology, Inc., Los Angeles, CA (US)

(72) Inventors: Alan H. Auerbach, Hermosa Beach, CA (US); Arie S. Belldegrun, Los Angeles, CA (US); Johann de Bono, London (GB)

(73) Assignees: Janssen Oncology, Inc., Los Angeles, CA (US); British Technology Group Limited, London (GB)

( * ) Notice: Subject to any disclaimer, the term of this patent is extended or adjusted under 35 U.S.C. 154(b) by 0 days.

(21) Appl. No.: 15/703,773

(22) Filed: Sep. 13, 2017

(65) Prior Publication Data

US 2018/0000840 A1 Jan. 4, 2018

Related U.S. Application Data

(63) Continuation of application No. 15/419,148, filed on Jan. 30, 2017, now abandoned, which is a continuation of application No. 15/019,353, filed on Feb. 9, 2016, which is a continuation of application No. 14/750,297, filed on Jun. 25, 2015, now abandoned, which is a continuation of application No. 14/485,083, filed on Sep. 12, 2014, now abandoned, which is a continuation of application No. 14/444,513, filed on Jul. 28, 2014, now abandoned, which is a continuation of application No. 13/034,340, filed on Feb. 24, 2011, now Pat. No. 8,822,438, which is a continuation of application No. 11/844,440, filed on Aug. 24, 2007, now abandoned.

(60) Provisional application No. 60/921,506, filed on Aug. 25, 2006.

(51) Int. Cl.
*A61K 31/58* (2006.01)
*A61K 31/573* (2006.01)

(52) U.S. Cl.
CPC ............ *A61K 31/58* (2013.01); *A61K 31/573* (2013.01)

(58) Field of Classification Search
CPC .............................. A61K 31/56; A61K 31/565
USPC ................................................ 514/170, 182
See application file for complete search history.

(56) References Cited

U.S. PATENT DOCUMENTS

| | | |
|---|---|---|
| 4,717,721 A | 1/1988 | DeLuca et al. |
| 4,851,401 A | 7/1989 | DeLuca et al. |
| 4,857,518 A | 8/1989 | DeLuca et al. |
| 4,866,048 A | 9/1989 | Calverley et al. |
| 5,120,722 A | 6/1992 | Baggiolini et al. |
| 5,145,846 A | 9/1992 | Baggiolini et al. |
| 5,190,935 A | 3/1993 | Binderup et al. |
| 5,237,110 A | 8/1993 | DeLuca et al. |
| 5,411,949 A | 5/1995 | Neef et al. |
| 5,446,035 A | 8/1995 | Neef et al. |
| 5,547,947 A | 8/1996 | Dore et al. |
| 5,604,213 A * | 2/1997 | Barrie ................... C07J 13/005 514/176 |
| 5,618,807 A | 4/1997 | Barrie et al. |
| 5,688,977 A | 11/1997 | Sisti et al. |
| 6,087,350 A | 7/2000 | Johnson et al. |
| 6,310,226 B1 | 10/2001 | Calverley et al. |
| 6,521,608 B1 | 2/2003 | Henner et al. |
| 6,559,139 B1 | 5/2003 | Johnson et al. |
| 6,872,568 B1 | 3/2005 | Ni et al. |
| 7,071,333 B2 | 7/2006 | Combs et al. |
| 7,256,193 B2 | 8/2007 | Kyle et al. |
| 7,482,334 B2 | 1/2009 | Frincke et al. |
| 7,547,687 B2 | 6/2009 | Reading et al. |
| 7,709,517 B2 | 5/2010 | Sawyers et al. |
| 8,183,274 B2 | 5/2012 | Sawyers et al. |
| 8,822,438 B2 | 9/2014 | Auerbach et al. |
| 9,126,941 B2 | 9/2015 | Sawyers et al. |
| 2002/0128240 A1 | 9/2002 | Mazess |
| 2003/0083231 A1 | 5/2003 | Ahlem et al. |
| 2003/0119795 A1 | 6/2003 | Henner et al. |
| 2004/0138187 A1 | 7/2004 | Reading et al. |
| 2005/0020546 A1 | 1/2005 | Laidlaw et al. |
| 2005/0101581 A1 | 5/2005 | Reading et al. |
| 2005/0233958 A1 | 10/2005 | Ni et al. |
| 2006/0003021 A1 | 1/2006 | Strugnell et al. |
| 2006/0003950 A1 | 1/2006 | Strugnell et al. |
| 2006/0018933 A1 | 1/2006 | Vaya et al. |

(Continued)

FOREIGN PATENT DOCUMENTS

DE 10061137 A1 6/2002
EP 0413270 A2 2/1991

(Continued)

OTHER PUBLICATIONS

Datta et al., The Journal of Urology, 1997;158:175-177.* Zhou et al., Asian Pacific Journal of Cancer Prevention, 2014;15:1313-1320.*
Fuse et al. Archives of Andrology, 52:35-38, Jan. 2006 (Year: 2006).*

(Continued)

*Primary Examiner* — San Ming R Hui
(74) *Attorney, Agent, or Firm* — BakerHostetler

(57) ABSTRACT

Methods and compositions for treating cancer are described herein. More particularly, the methods for treating cancer comprise administering a 17α-hydroxylase/$C_{17,\,20}$-lyase inhibitor, such as abiraterone acetate (i.e., 3β-acetoxy-17-(3-pyridyl) androsta-5, 16-diene), in combination with at least one additional therapeutic agent such as an anti-cancer agent or a steroid. Furthermore, disclosed are compositions comprising a 17α-hydroxylase/$C_{17,\,20}$-lyase inhibitor, and at least one additional therapeutic agent, such as an anti-cancer agent or a steroid.

9 Claims, No Drawings

(56) References Cited

U.S. PATENT DOCUMENTS

| | | |
|---|---|---|
| 2006/0018934 A1 | 1/2006 | Vaya et al. |
| 2006/0024365 A1 | 2/2006 | Vaya et al. |
| 2006/0030608 A1 | 2/2006 | Nelson et al. |
| 2007/0203107 A1 | 8/2007 | Frincke et al. |
| 2007/0213309 A1 | 9/2007 | Reading et al. |
| 2007/0265236 A1 | 11/2007 | Reading et al. |
| 2007/0275937 A1 | 11/2007 | Reading et al. |
| 2007/0275938 A1 | 11/2007 | Reading et al. |
| 2008/0004286 A1 | 1/2008 | Wang et al. |
| 2008/0004287 A1 | 1/2008 | Ma et al. |
| 2008/0051375 A1 | 2/2008 | Auerbach et al. |
| 2008/0085873 A1 | 4/2008 | Reading et al. |
| 2008/0138426 A1 | 6/2008 | Hara et al. |
| 2009/0124587 A1 | 5/2009 | Auerbach et al. |

FOREIGN PATENT DOCUMENTS

| | | |
|---|---|---|
| EP | 0912535 A1 | 5/1999 |
| EP | 0914116 A1 | 5/1999 |
| EP | 1140192 A2 | 10/2001 |
| EP | 1336602 A1 | 8/2003 |
| EP | 1379246 A1 | 1/2004 |
| EP | 1385514 A1 | 2/2004 |
| EP | 1385515 A1 | 2/2004 |
| EP | 1385518 A1 | 2/2004 |
| EP | 1423381 A1 | 6/2004 |
| EP | 1463733 A2 | 10/2004 |
| EP | 1466628 A1 | 10/2004 |
| EP | 1487829 A1 | 12/2004 |
| EP | 1515949 A1 | 3/2005 |
| EP | 1556354 A2 | 7/2005 |
| EP | 1562932 A1 | 8/2005 |
| EP | 1562936 A2 | 8/2005 |
| EP | 1572299 A1 | 9/2005 |
| EP | 1583524 A1 | 10/2005 |
| EP | 1583763 A1 | 10/2005 |
| EP | 1598338 A1 | 11/2005 |
| EP | 1598339 A1 | 11/2005 |
| EP | 1598340 A1 | 11/2005 |
| EP | 1631285 A1 | 3/2006 |
| EP | 1307197 B1 | 4/2006 |
| EP | 1648879 A1 | 4/2006 |
| EP | 1664016 A2 | 6/2006 |
| EP | 1664041 A1 | 6/2006 |
| EP | 1674479 A1 | 6/2006 |
| EP | 1676577 A1 | 7/2006 |
| EP | 1803718 A1 | 7/2007 |
| EP | 1810970 A1 | 7/2007 |
| EP | 1412368 B1 | 8/2007 |
| EP | 1673092 B1 | 8/2007 |
| EP | 1862458 A2 | 12/2007 |
| EP | 1867644 A1 | 12/2007 |
| EP | 1918279 A2 | 5/2008 |
| EP | 1927858 A1 | 6/2008 |
| EP | 1930322 A1 | 6/2008 |
| EP | 1942106 A1 | 7/2008 |
| EP | 1975164 A2 | 10/2008 |
| EP | 2478907 A2 | 7/2012 |
| IN | 2005/MUM01012 | 8/2005 |
| IN | 2005/MUM01013 | 8/2005 |
| JP | A-2003-525254 | 8/2003 |
| JP | A-2006-515623 | 6/2006 |
| WO | 92/00992 A1 | 1/1992 |
| WO | 93/20097 A1 | 10/1993 |
| WO | 95/09178 A1 | 4/1995 |
| WO | WO 01/64251 | 9/2001 |
| WO | 01/81364 A1 | 11/2001 |
| WO | 01/93836 A2 | 12/2001 |
| WO | 02/03286 A1 | 1/2002 |
| WO | 02/32861 A2 | 4/2002 |
| WO | 02/53138 A2 | 7/2002 |
| WO | 02/91993 A2 | 11/2002 |
| WO | 2002/102783 A1 | 12/2002 |
| WO | 03/20699 A2 | 3/2003 |
| WO | 03/37252 A2 | 5/2003 |
| WO | 03/39460 A2 | 5/2003 |
| WO | 03/86388 A1 | 10/2003 |
| WO | 03/86404 A1 | 10/2003 |
| WO | 03/92595 A2 | 11/2003 |
| WO | 2004/016753 A2 | 2/2004 |
| WO | 2004/037269 A1 | 5/2004 |
| WO | 2004/041164 A2 | 5/2004 |
| WO | WO 2004/062620 | 7/2004 |
| WO | 2005/016236 A2 | 2/2005 |
| WO | 2005/021487 A1 | 3/2005 |
| WO | 20051107801 A2 | 11/2005 |
| WO | 2006/004917 A2 | 1/2006 |
| WO | 2006/021776 A1 | 3/2006 |
| WO | 2006/027266 A1 | 3/2006 |
| WO | 2006/050402 A1 | 5/2006 |
| WO | 2006/081152 A2 | 8/2006 |
| WO | 2006/116217 A2 | 11/2006 |
| WO | 2006/116716 A2 | 11/2006 |
| WO | 2007/014327 A2 | 2/2007 |
| WO | 2008/024484 A1 | 2/2008 |
| WO | 2008/039254 A2 | 4/2008 |
| WO | 2008/062466 A2 | 5/2008 |
| WO | 2008/100985 A2 | 8/2008 |
| WO | 2008/109740 A2 | 9/2008 |
| WO | 2008/127290 A2 | 10/2008 |

OTHER PUBLICATIONS

Fallowfield et al., "Patients' preference for administration of endocrine treatments by injection or tablets", results from a study of women with breast cancer, Annals of Oncology vol. 17 No. 2 Feb. 2006, pp. 205-210.

Fable Zustovich and Davide Pastorelli,Therapeutic management of bone metastasis in prostate cancer: an update, Expert Review of Anticancer Therapy, http://dx.doi.org/10.1080/14737140.2016.1241148, Sep. 27, 2016.

F. Labrie et al., "Anti-hormone Treatment for Prostate Cancer Relapsing after Treatment with Flutamide and Castration", British Journal of Urology, (1989) 63 ,pp. 634-638.

Excerpts from Seifter, Concepts in Medical Physiology, Chapter 34, pp. 540-553, Chapter 37, pp. 606-620 (2005), Filed for Case IPR2016-00286, Janssen Exhibit 2058.

Ernel Arinc et al., "Molecular Aspects of Monooxygenases and Bioactivation of Toxic Compounds", Series A: Life Sciences vol. 202 Mylan Pharms. Inc., 28 pages.

Erica L. T. Van Den Akker et al., "Differential inhibition of 17alpha-hydroxylase and 17,20-lyase activities by three novel missense CYP17 mutations identified in patients with P450c17 deficiency", The Journal of Clinical Endocrinology 8, Metabolism Dec. 2002, vol. 87 No. 12 pp. 5714-5721.

Eric J. Small et al., "Second-Line Hormonal therapy for Advanced Prostate Cancer: A Shifting Paradigm", journal of Cliniol Oncology, vol. 15, No. 1 Jan. 1997, pp. 382-388.

Eric J. Small et al., "Ketoconazole Retains Activity in Advanced Prostate Cancer Patients With Progression Despite Flutamide Withdrawal", The Journal of Urology, vol. 157 Apr. 1997, pp. 1204-1207.

Eric J. Small et al., "Antiandrogen Withdrawal Alone or in Combination With Ketoconazole in Androgen-Independent Prostate Cancer Patients: A Phase III Trial (CALGB9583)", Journal of Clinical Oncology, *Wockhardt* vs. *Janssen*, Filed for Case IPR2016-01582, Janssen Exhibit 2172, on Apr. 3, 2017, 18 pages.

Ended E. et al., "Establishment of reference values for endocrine tests. Part IV: Adrenal insufficiency", Netherlands, Journal of Medicine 2005, vol. 63, No. 11, pp. 435-443.

Email from Johann De-Bono, "Re: Cougar Biotechnology Advisory Board Meeting for CB7630", (Feb. 10, 2005), 3 pages.

Email from Bellegrun, Arie M.D., "Re: UK abiraterone protocol", (Mar. 7, 2005), 2 pages.

Email from B. Donovan regarding IPR2016-01332—Exhibit 2134 (Apr. 4, 2017), 1 page.

EMA—Zytiga Product Information, http://www.ema.europa.eu/docs/en_GB/document_library/EPAR_-_Product_Information/human/002321/WC500112858.pdf 37 pages.

(56) References Cited

OTHER PUBLICATIONS

Edward G. Biglieri, et al., "17-Hydroxylation De6.ciency in Man", Journal of Clinical Investigation, vol. 45, No. 12, 1966, 10 pages.
ECOG Performance Status, "Developed by the Eastern Cooperative Oncology Group, Robert L. Comis, MD, Group Chair", *Wockhardt v. Janssen*, Field for Case # IPR2016-01582, Janssen Exhibit 2158, http://ecog-acrin.org/resources/ecog-performance-status, Mar. 14, 2017, 2 pages.
Duc et al., "In vitro and in vivo models for the evaluation of potent inhibitors of male rat 17 (Alpha)-hydroxylase/C17,20-lyase," Journal of Steroid Biochemistry & Molecular Biology, 2003, Filed for Case IPR2016-00286, Janssen Exhibit 2012, vol. 84 pp. 537-542.
Dorin et al., "Diagnosis of Adrenal Insufficiency", Academia and Clinic, Annals of Internal Medicine, Filed for Case IPR2016-00286, Janssen Exhibit 2051, on Aug. 5, 2003, vol. 139, No. 3, pp. 194-204.
Donold L. Trump et al., "High-Dose Ketoconazole in Advanced Hormone-Refractory Prostate Cancer: Endocrinologic and Clinical Effects", Journol of Clinicol Oncology, vol. 7, No. 8 Aug. 1989, pp. 1093-1098.
Dizdar 2015, Is Dexamethasone a Better Partner for Abiraterone Than Prednisolone, The Oncologist May 2015 vol. 20, No. 5 e13.
Division of Endocrinologg et al., "Dose-response aspects in the clinical assessment of the hypothalamo-pituitary-adrenal axis and the low-dose adrenocorticotropin test", European Journal of Endocrinology, 1996, 135: pp. 27-33.
Dickstein G., et al., "Low dose ACTH test—A word of caution to the word of caution" when and how to use it, Journal of Clinical Endocrinology and Metabolism 1997, vol. 82 No. 1, 322 pages.
Dickstein G et al., "One microgram is the lowest ACTH dose to cause a maximal cortisol response. There is no diurnal variation of cortisol response to submaximal ACTH stimulation", European Journal of Endocrinology 1997, vol. 137 No. 2 pp. 172-175.
Di Cerbo et al., "Combined 17 alpha-Hydroxylase/17, 20-lyase deficiency caused by Phe93 Cys mutation in the CYP17 gene", The Journal of Clinical Endocrinology & Metabolism 2002, vol. 87, No. 2 pp. 898-905.
Dennis L. Kasper, et al. (Eds.), Harrison's Principles of Internal Medicine, 16th Edition (2005), 12 pages.
DeMario et al., "Oral Chemotherapy", Rationale and Future Directions, Journal of Clinical Oncology, vol. 16, No. 7, Jul. 1998, pp. 2557-2567.
Declaration of Professor Ian Judson, "cited in the Opposition of EP Patent 2061561", Filed for case IPR2016-00286, Janssen Exhibit 2005, on Jun. 29, 2015, 3 pages.
Declaration of Dr. Robert Charnas, Feb. 2, 2016, 3 pages.
Declaration of Dr. Gerhardt Allard, 29 pages.
Declaration of DeForest McDuff, Ph.D. dated Jan. 16, 2017.
De Bono et al., "Abiraterone and Increased Survival in Metastatic Prostate Cancer", New England Journal of Medicine, Filed for Case IPR2016-01582, Janssen Exhibit 2159, on May 26, 2011, Established in 1812, vol. 364, No. 21, pp. 1995-2005.
David Osoba et al., "Health-Related Quality of Life in Men With Metastatic Prostate Cancer Treated With Prednisone Alone or Mitoxantrone and Prednisone", Journal of Clinical Oncology, vol. 17, No. 6 (Jun. 1999), pp. 1654-1663.
Danila et al., "Phase II Multicenter Study of Abiraterone Acetate Plus Prednisone Therapy in Patients With Docetaxel-Treated Castration-Resistant Prostate Cancer," Journal of Clinical Oncology, Filed for Case IPR2016-00286, Janssen Exhibit 2016, on March 20, 2010, vol. 28, No. 9, pp. 1496-1501.
Daniel C. Danila et al., "Prednisone Therapy in Patients With Docetaxel-Treated Castration-Resistant Prostate cancer", Journal of Clinical Oncology, vol. 28, No. 9, Mar. 20, 2010, pp. 1496-1501.
D.E. Rathkopf et al., "Updated Interim Efficacy Analysis and Long-Term Safety of Abiraterone Acetate in Metastatic Castration-Resistant Prostate Cancer Patients Without Prior Chemotherapy(COU-AA-302)", European Urology, filed for Case# IPR2016-00286, No. 66, pp. 815-825, 2014.
D. Trump et al., Phase II Trial of High-Dose, Intermittent Calcitriol (1,25 Dihydroxyvitamin D3) and Dexamethasone in Androgen-Independent Prostate Cancer American Cancer Society vol. 106, No. 10, pp. 2136-2142, May 15, 2006.
D. Lorente et al., Tumour responses following a steroid switch from prednisone to dexamethasone in castration-resistant prostate cancer patients progressing on abiraterone, British Journal of Cancer, (2014) 111, pp. 2248-2253.
D. Feldman, "Ketoconazole and Other Imidazole derivatives as Inhibitiors of steroidogenesis", filed for Case#IPR2016-00286, vol. 7, No. 4, 12 pages.
Credt Suisse, "Prostate Cancer-Implications of Zytiga's Pre-Chemo Approval," Dec. 11, 2012.
Crawford et al., "Treating Patients with Metastatic Castration Resistant Prostate Cancer", A Comprehensive Review of Available Therapies, The Journal of Urology, vol. 194, Dec. 2015. pp. 1537-1547.
Cowen & Company, "Quick Take: Zytiga Gets FDA OK for Use in Pre-Chemo Selling on rPFS Data—Johnson & Johnson,"Accessed (Dec. 11, 2012).
Cowen & Company, "Biotechnology Quarterly," Jul. 2, 2012.
Cougar Biotechnology, Inc., Clinical Study Report: COU-AA-001 and COU-AA-001 EXT, Nov. 17, 2010, 7 pages.
Cougar Biotechnology, A Phase i/ii Open Label Study of the 17-Hydroxylase/ c17-20 lyase Inhibitor, Abiraterone Acetate in Patients with Prostate Cancer Who have Failed Hormone Therapy, Latter to Johann De-Bono, Re: Revised abiraterone protocol, Dec. 6, 2004, 86 pages.
Costa-Santos, M. et al., "Two Prevalent CYP17 Mutations and Genotype-Phenotype Correlations in 24 Brazilian Patients with 17-Hydroxylase Deficiency," J. Clin. Endocrin. & Metabol. vol. (89)1, pp. 49-60, 2004.
Continuing Challenge of Hormone-Refractory Prostate Cancer, Declaration of Oliver Sartor, "Clinical Genitourinary Cancer", filed for case Janssen IPR2016-01582, Janssen Exhibit 2156 on Mar. 2006, pp. 238-239.
Conde and Aronson, "Risk factors for male osteoporosis," Urologic Oncology, Seminars and Original Investigations, Filed for Case IPR2016-00286, Janssen Exhibit 2025, on 2003, vol. 21, pp. 380-383.
ClinicalTrials.gov, "Phase II Clinical Trial of Abiraterone Acetate Without Exogenous Glucocorticoids in Men With Castrationresistant Prostate Cancer With Correlative Assessment of Hormone Intermediates.", NCT02025010, *Amerigen v. Janssen*, Case # IPR2016-00286, 5 pages.
ClinicalTrials.gov Archive, NCT00485303 on Jun. 11, 2007. http://clinicaltrials.gov/archive/NCT00485303/, 3 pages.
Clinical trial patient data extract, for Patient 1, Patient 2, 2 pages.
Mayo Clinic "Prednisone and other corticosteroids" for Case # IPR2016-00286 Janssen Exhibit 2102 Oct. 3, 2016 4 Pages.
Marwan Fakih et al., "Glucocorticoids and Treatment of Prostate Cancer: A Preclinical and Clinical Review", Urology 60:2002, pp. 553-561.
Marked up version of Exhibit C to Bantle declaration—ketoconazole, *Mylan vs. Janssen*, Filed for case IPR2016-01332, Janssen Exhibit 2180, 1 page.
Marked up version of Exhibit C to Bantle declaration—Aminoglutethimide, *Mylan vs. Janssen*, Filed for Case IPR2016-01332, Janssen Exhibit 2181, 1 page.
Marked up version of Exhibit C to Bantle declaration—Abiraterone acetate, *Mylan vs. Janssen*, Filed for Case IPR2016-01332, Janssen Exhibit 2182, 1 page.
Mark. J. Ratain et al., "Statistical and Ethical Issues in the Design and Conduct of Phase I and II Clinical Trials of New Anticancer Agents", Journal of the National Cancer Institute, vol. 85, No. 20, pp. 1637-1649, Oct. 20, 1993.
Marini et al., "The effect of adjuvant prednisone combined with CMF on patterns of relapse and occurrence of second malignancies in patients with breast cancer", Annals of Oncology, file for Case IPR2016-00286, Janssen Exhibit 2060, on 1996, vol. 7, pp. 245-250.
Marik PE et al., "Recommendations for thediagnosis and management of corticosteroid insufficiency in critically ill adult patients" consensus statements from an international task force by the American College of Critical Care Medicine. Critical Care Medicine 2008, vol. 36, No. 6, pp. 1937-1949.

(56) References Cited

OTHER PUBLICATIONS

Maria I., "Male pseudohermaphroditism due to 17 alpha-hydroxylase deficiency", Journal of Clinical Investigation 1970, vol. 49 No. 10 pp. 1930-1941.

Marc B. Garnick, "Management of Metastatic Carcinoma of the Prostate—Treatment Options and Controversies", in Prostatic Disorders, (David F. Paulson et al. eds., 1989), pp. 354-67.

Mantero et al., "Long-term treatment of mineralocorticoid excess syndromes", Divisions of Endocrinology, Universities of Padua and Ancona, Italy, Steroids, file for Case IPR2016-00286, Janssen Exhibit 2066, on Jan. 1995, vol. 60 pp. 81-86.

M.B. Sawyer et al., "Phase I Study of an Oral Formulation of ZD9331 Administered Daily for 28 Days", Journal of Clinical Oncology, filed for IPR2016-00286, vol. 21, No. 9, pp. 1859-1865, May 1, 2003.

M. Morioka et al., Prostate-Specific Antigen Levels and Prognosis in Patients with Hormone-Refractory Prostate Cancer Treated with Low-Dose Dexamethasone, Urologia Internationalis vol. 68, at 10-15 (2002).

Lund, Sweden and Paris, Apr. 16, 2015, "Active Biotech and IPSEN announce their decision to discontinue the levelopment of tasquinimod in prostate cancer", Website: https://globenewswire.com/news-release/2015/04/16/724977/10129220/en/Active-Biotech-and-Ipsen-announce . . . , Janssen Exhibit 2074, *Mylan* v. *Janssen* IPR2016-01332, Sep. 30, 2016.

Lund, Sweden and Paris, Apr. 16, 2015, "Active Biotech and Ipsen announce their decision to discontinue the development of tasquinimod in prostate cancer", Website: https://globenewswire.com/news-release/2015/04/16/724977/10129220/en/Active-Biotech-and-Ipsen-announce . . . , Janssen Exhibit 2074, *Wockhardt* v. *Janssen* Case # IPR2016-01582, Sep. 30, 2016.

Letter to Kevin McNulty, Re: "*BTG International Ltd. et al.* v. *Actavis Laboratories FL, Inc. et al.*, Civil Action No. 15-05909 (KM) (JBC)", Case # 15-cv-05909-KM-JBC Document 203 Filed May 23, 2016 p. 1 of 1.

Letter to Kevin McNulty, Re: "*BTG International Limited, et al.*, vs. *Actavis Laboratories FL, Inc., et al.*," filed for case# 15-cv-05909-KM-JBC, Document No. 232, on Oct. 21, 2016, p. 1 of 2.

Letter to Kevin McNulty, Re: "*BTG International Limited, et al.*, vs. *Actavis Laboratories FL, Inc., et al.*," filed for case# 15-cv-05909-KM-JBC, Document No. 231, on Oct. 21, 2016, p. 1 of 1.

Letter to James B. Clark, "*BTG International Limited, et al.* v. *Actavis Laboratories FL, Inc., et al.* Civil Action No. 15-05909 (KM) (JBC)" Case # 15-cv-05909-KM-JBC, Document # 208 Filed Jun. 27, 2016 p. 1 of 3.

Letter to James B. Clark, "*BTG International Limited, et al.* v. *Actavis Laboratories FL, Inc., et al.* Civil Action No. 15-05909 (KM) (JBC)" Case # 15-cv-05909-KM-JBC, Document # 207 Filed Jun. 24, 2016 p. 1 of 3.

Lara and Meyers, "Treatment Options in Androgen-Independent Prostate Cancer" Cancer Investigation, file for Case IPR2016-00286, Janssen Exhibit 2053, vol. 17, No. 2, on 1999, pp. 137-144.

L. Collette et al., Prostate-specific antigen (PSA) alone is not an appropriate surrogate marker of long-term therapeutic benefit in prostate cancer trials, European Journal of Cancer, 42, pp. 1344-1350 (2006).

L. Collette et al., Is Prostate-Specific Antigen a Valid Surrogate End Point for Survival in Hormonally Treated Patients With Metastatic Prostate Cancer? Joint Research of the European Organisation for Research and Treatment of Cancer, the Limburgs Universitair Centrum, and AstraZeneca Pharmaceuticals, Journal of Clinical Oncology, vol. 23, No. 25, pp. 6139-6148 (Sep. 1, 2005).

Kuzel et aL., "A Phase II Study of Continuous Infusion 5-Fluorouracil in Advanced Hormone Refractory Prostate Cancer", Cancer, file for Case IPR2016-00286, Janssen Exhibit 2054, vol. 72, No. 6, on Sep. 15, 1993, 1965-1968 pages.

Krishnan et al., "A Glucocorticoid-Responsive Mutant Androgen Receptor Exhibits Unique Ligand Specificity: Therapeutic Implications for Androgen-Independent Prostate Cancer," Endocrinology, Filed for Case IPR2016-00286, Janssen Exhibit 2024, on May 2002, vol. 143, No. 5, pp. 1889-1900.

Knol et al., "The Mis-use of Overlap of Confidence Intervals to Assess Effect Modification", Filed for Case *Wockhardt* v. *Janssen* IPR2016-01332, Janssen Exhibit 2183, on 2011, Eur. J. Epidemiol., vol. 26, 253-254 pages.

Kirby M. et al., "Characterising the castration-resistant prostate cancer population: A systematic review", Int'l J. Clinical Practice, vol. 65 No. (11): pp. 1180-1192, (Nov. 2011).

Kasper D.L. et al. (Eds.), "Harrison's Principles of Internal Medicine", 16th Edition (2005), 549 pp. 42.

K. Nishimura et al., Low Doses of Oral Dexamethasone for Hormone-Refractory Prostate Carcinoma, Cancer vol. 89, No. 12, at 2570-2576 (Dec. 15, 2000).

K. Kobayashi et al., " Mineralocorticoid Insufficiency Due to Suramin Therapy, Cancer", vol. 78, No. 11 (Dec. 1, 1996).

K. Akakura et al., Possible Mechanism of Dexamethasone Therapy for Prostate Cancer: Suppression of Circulating Level of Interleukin-6, The Prostate, 56:106-109 (2003).

Juliet Richards et al., Interactions of Abiraterone, Eplerenone, and Prednisolone with Wild-type and Mutant Androgen Receptor: A Rationale for Increasing Abiraterone Exposure or Combining with MDV3100, Cancer Res; 72(9) pp. 2176-2182, May 1, 2012.

Julian Seifter et al, "Concepts in Medical Physiology", Lippincott Williams and Wilkins, *Wockhardt* vs. *Janssen*, Files for Case IPR2016-01582, Janssen Exhibit 2171, 540-620 pages.

Jubelirer and Hogan, "High Dose Ketoconazole for the Treatment of Hormone Refractory Metastatic Prostate Carcinoma: 16 Cases and Review of the Literature," The Journal of Urology, Filed for Case IPR2016-00286, Janssen Exhibit 2018, on Jul. 1989, vol. 142, No. 1, pp. 89-91.

Johnson & Johnson, "Zytiga Approved in the EU for Use in the Treatment of Metastatic Castration-Resistant Prostate Cancer Before Chemotherapy," Jan. 11, 2013, 4 pages.

Johnson & Johnson Reports 2015 Fourth-Quarter Results, *Mylan* v. *Janssen*, Field for Case # IPR2016-01332, Janssen Exhibit 2033, Jan. 26, 2016, 10 pages.

Johnson & Johnson Reports 2013 Fourth-Quarter Full-Year Results, Janssen Exhibit 2034, Jan. 21, 2014, 8 pages.

Johnson & Johnson Press Release, "Zytiga(Registered) approved in the EU for use in the treatment of metastatic aastration-resistant prostate cancer before chemotherapy," Jan. 11, 2013, http://www.jnj.com/media-center/press-releases/zytiga-approvedin- the- eu-for-use-in-the-treatment-of-metastatic-castrationresistant- prostate-cancer-before-chemotherapy, 4 pages.

Johnson & Johnson Announces Definitive Agreement to Acquire Cougar Biotechnology, Inc., "Access to Late-Stage, First-in-Class Prostate Cancer Treatment Strengthens Presence in Oncology" May 21, 2009. pp. 4.

John S. et al., "Secondary Hormonal Therapy for Advanced Prostate Cancer", The Journal fo Urology, vol. 175, Jan. 2006, pp. 27-34.

Jevtana Website, "Dosing and Administration", http://www.jevtana.com/hcp/dosing/default.aspx (accessed Jun. 28, 2016), Mylan Pharms. Inc., Exhibit 1049, 4 pages.

Jevtana prescribing information (Sep. 2016), Jevtana(Registered) (cabazitaxel) injection, for intravenous use Initial U.S. Approval: 2010, 25 pages.

Jevtana (Registered) (cabazitaxel) injection, for intravenous use Initial U.S. Approval: 2010, Jevtana Label, Sep. 2016, *Amerigen* vs. *Janssen* filed for case IPR2016-00286, Amerigen Exhibit 1149, 25 pages.

Jennifer Craft, "Eplerenone (Inspra), a new aldosterone antagonist for the treatment of systemic hypertension and heart failure", Baylor University Medical Center Proceedings, file for Case IPR2016-00286, Janssen Exhibit 2062, on Apr. 2004, vol. 17, No. 2, pp. 217-220.

Janssen Research & Development, Clinical Study Report: Synopsis Protocol JNJ-212082-JPN-201; Phase 2, 9 pages.

Janssen Exhibit 2006, *Amerigen* v. *Janssen* IPR2016-00286, Clinical Cancer Research, A Journal of the American Association for Cancer Research, Letter to Ian Judson, RE: "Manuscript# 030579,

(56) References Cited

OTHER PUBLICATIONS

Hormonal impact of the 17a-hydroxylase/C17, 20-lyase inhibitor abiraterone acetate (CB7630) in patients with prostate cancer", Dated May 12, 2003, 4 pages.
J.A. Storlie et al., Prostate Specific Antigen Levels and Clinical Response to Low Dose Dexamethasone for Hormone-Refractory Metastatic Prostate Carcinoma, Cancer vol. 76, No. 1, at 96-100 (Jul. 1, 1995).
J. Trachtenberg and A. Pont, The Lancet, Ketoconazole Therapy for Advanced Prostate Cancer, Aug. 25, 1984, pp. 433-435.
J. Gonzaalbez et al., "Establishment of reference values for standard dose short synacthen test (250 microgram), low dose short synacthen test (1 microgram) and insulin tolerance test for assessment of the hypothalamo-pituitary-adrenal axis in normal subjects", Clinical Endocrinology 2000, vol. 53, 199-204.
J&J Jan. 22, 2013 Press Release Johnson & Johnson Reports 2012 Fourth-Quarterand Full-Year Results for Case # IPR2016-00286.
Annane D et al., "Effect of treatment with low doses of hydrocortisone and fludrocortisone on mortality in patients with septic shock", JAMA, Aug. 21, 2002, vol. 288, No. 7, pp. 862-871.
Andrew J. Armstrong et al., "New drugs in prostate cancer", Current Opinion in Urology 2006, vol. 16: pp. 138-145.
Amerigen Exhibit1071, Cowen and company, "Biotechnology Quarterly, Industry Outlook", filed for Case# IPR2016-00286, Jul. 2012, 41 pages.
American Cancer Society, "Key Statistics for Prostate Cancer" What is Prostate Cancer? Topics. Filed for Case # IPR2016-01332 Mar. 6, 2017, 3 Pages.
Altman et al., "The Revised CONSORT Statement for Reporting Randomized Trials: Explanation and Elaboration", Annals of Internal Medicine vol. 134, No. 8, Apr. 17, 2001, pp. 663-694.
Alison Reid et al., genitourinary tumors, "Inhibition of Androgen Synthesis Results in a High Response Rate in Castration Refractory Prostate Cancer (CRPC)", Annals of Oncology 18 (Supplement 9), vol. 18, Jul. 2007, pp. 173-174.
Alison H.M. Reid et al., "Significant and Sustained Antitumor Activity in Post-Docetaxel Castration-Resistant Prostate Cancer With the CYP17 Inhibitor Abiraterone Acetate", Journal of Clinical Oncology, vol. 28, No. 9 Mar. 20, 2010, pp. 1489-1495.
Acadamy of Managed Care Pharmacy (AMCP) Nexus 2016, National Harbor, MD, USA; Oct. 3-6, 2016 filed for Janssen IPR2016-01332.
Abiraterone: a story of scientific innovation and commercial partnership, http://www.icr.ac.uk/news-features/latestfeatures/abiraterone-a-story-of-scientific-innovation-andcommercial-partnership, Dec. 19, 2016, pp. 14.
Abiraterone Cougar Biotechnology Ravi A Madan & Philip M Arlen, Idrugs 2006, vol. 9, No. 1, pp. 49-55.
Abiraterone Acetate: Abbreviated Clinical Study Report Synopsis COU-AA-BE (Doc. EDMS-ERI-13494974:2.0) ("BE Synopsis") 5 pages.
Abad L et al., "Male pseudohermaphroditism with 17 alpha-hydroxylase deficiency", A case report. Br J Obstet Gynaecol Dec. 1980, vol. 87 No. 12 pp. 1162-1165.
A O'Donnell et al., "Hormonal impact of the 17 (Alpha)-hydroxylase/C 17,20-lyase inhibitor abiraterone acetate (CB7630) in patients with prostate cancer" British Journal of Cancer filed for Case Amerigen Exhibit 2031 on 2004, vol. 90, No. 12, pp. 2317-2325.
2011 Zytiga(Registered) Approval Prescribing Information, Zytiga(Trademarks), (abiraterone acetate) Tablets for Oral Administration Initial U.S. Approval—2011, Apr. 2011, 22 pages.
"Tokai Pharmaceuticals Announces Clinical Update", Janssen Exhibit 2073, *Amerigen* vs. *Janssen*, filed for Case # IPR2016-00286, Jul. 26, 2016, 2 Pages.
"Takeda Announces Termination of Orteronel (TAK-700) Development for Prostate Cancer in Japan, U.S.A. and Europe", Janssen Exhibit 2075, *Amerigen* vs. *Janssen*, filed for Case # IPR2016-00286, Jun. 19, 2014, 2 Pages.
"OncoGenex Announces Top-Line Survival Results of Phase 3 Synergy Trial Evaluating Custirsen for Metastatic Castrate-Resistant Prostate Cancer", Janssen Exhibit 2077, *Amerigen* vs. *Janssen*, filed for Case # IPR2016-00286, Apr. 28, 2014, 2 Page.
"Bristol-Myers Squibb Reports Results for Phase 3 Trial of Yervoy (Registered) (Ipilimumab) in Previously-Treated Castration-Resistant Prostate Cancer", Janssen Exhibit 2078, *Amerigen* v. *Janssen*, filed for Case # IPR2016-00286, Sep. 12, 2013, 6 Pages.
J& J Jan. 20, 2015 Johnson & Johnson Reports 2014 Fourth-Quarter and Full-Year Results Filed for Case # IPR2016-01332 8 pages.
J J. Body, "Low-dose prednisone and increased risk of development of bone metastases", Annals of Oncology, file for Case IPR2016-00286, Janssen Exhibit 2061, on 1996, vol. 7, pp. 643-645.
Inspra (eplerenone) tablets, Initial U.S. Approval: 2002, *Wockhardt* v. *Janssen* filed for Case # IPR2016-01332, Janssen Exhibit 2129, 8 Pages.
In the United States Patent and Trademark Office, Before the Patent Trial and Appeal Board, *Mylan Pharmaceuticals, Inc.*, (Petitioner) vs. *Janssen Oncology, Inc.*, (Patent Owner) for Patent No. 8,822,438 B2, "Declaration of Christopher A. Vellturo, Ph.D. in Support of Patent Owner Response" filed for Case # IPR2016-01332, Janssen Exhibit 2044.
In the United States Patent and Trademark Office, Before the Patent Trial and Appeal Board, *Mylan Pharmaceuticals Incorporated*, (Petitioner) v. *Janssen Oncology Inc.*, U.S. Pat. No. 8,822,438, to Auerbach et al, "Methods and Compositions for Treating Cancer", Case No. IPR2016-01332, Issue date Sep. 2, 2014., Declaration of Marc B. Garnick, M.D.
In the United States District Court,for the District of New Jersey, *BTG International Limited, Janssen Biotech, Inc., Janssen Oncology, Inc.*, and *Janssen Research & Development, LLC*, (Plaintiffs) vs. *Actavis Laboratories FL, Inc.*, Case # 15-cv-05909-KM-JBC, Document # 77, filed Oct. 13, 2015, p. 1 of 118.
In the United States District Court, for the District of New Jersey, BTG International Limited, Janssen Biotech, Inc., Janssen Oncology, Inc., Janssen Research & Development, LLC, for Case # 15-cv-05909-KM-JBC, "Plaintiffs' Opening Claim Construction Brief" Document # 209 Filed Jun. 30, 2016 p. 1 of 15.
In the United States District Court, for the District of New Jersey, *BTG International Limited, Janssen Biotech, Inc., Janssen Oncology, Inc., Janssen Research & Development, LLC*, (Plaintiffs) vs. *Actavis Laboratories FL, Inc.*, Case # 15-cv-05909-KM-JBC, "Plaintiffs' Responsive Claim Construction Brief" Document 220 Filed Aug. 31, 2016 p. 1 of 25.
In the United States District Court, for the District of New Jersey, *BTG International Limited, Janssen Biotech, Inc., Janssen Oncology, Inc., Janssen Research & Development, LLC*, (Plaintiffs) vs. *Actavis Laboratories FL, Inc.*, Case # 15-cv-05909-KM-JBC, "Plaintiffs Janssen's Answer to Defendant Mylan'S Counterclaims" Document # 202 Filed May 13, 2016 p. 1 of 9.
In the United States District Court, for the District of New Jersey, *BTG International Limited, Janssen Biotech, Inc., Janssen Oncology, Inc., Janssen Research & Development, LLC*, (Plaintiffs) vs. *Actavis Laboratories FL, Inc.*, Case # 15-cv-05909-KM-JBC, "Declaration of Keith J. Miller, ESQ." Document 209-1 Filed Jun. 30, 2016 p. 1 of 2.
In the United States District Court, for the District of New Jersey, *BTG International Limited, Janssen Biotech, Inc., Janssen Oncology, Inc., Janssen Research & Development, LLC*, (Plaintiffs) vs. *Actavis Laboratories FL, Inc.*, Case # 15-cv-05909-KM-JBC, "Declaration of Keith J. Miller, Esq." Document # 220-1 Filed Aug. 31, 2016 p. 1 of 2.
In the United States District Court for the District of New Jersey, *BTG International Limited, Janssen Biotech, Inc., Janssen Oncology, Inc., Janssen Research & Development, LLC*, (Plaintiffs) vs. *Actavis Laboratories FL, Inc., et al.*, (Defendants), "Complaint for Patent Infringement", filed for Case 2:15-cv-05909-KM-JBC, Document No. 1 on Jul. 31, 2015 p. 1 of 106.
In the United States District Court for the District of New Jersey, *BTG International Limited, Janssen Biotech, Inc., et al.*, (Plaintiffs) vs. *Actavis Laboratories FL, Inc., et al.*, (Defendants), "Plaintiffs' Answer to Defendant Actavis's Counterclaims", Field for Case # 2:15-cv-05909-KM-JBC, Document No. 133, on Nov. 9, 2015, p. 1 of 11.

(56) References Cited

OTHER PUBLICATIONS

In the United States District Court for the District of New Jersey, *BTG International Limited, Janssen Biotech, Inc., et al.*, (Plaintiffs) vs. *Actavis Laboratories FL, Inc., et al.*, (Defendants), "Plaintiff Janssen's Answer to Defendant Wockhardt's Counterclaims", Field for Case # 2:15-cv-05909-KM-JBC, Document No. 127, on Nov. 6, 2015, p. 1 of 23.

In the United States District Court for the District of New Jersey, *BTG International Limited, Janssen Biotech, Inc., et al.*, (Plaintiffs) vs. *Actavis Laboratories FL, Inc., et al.*, (Defendants), "Plaintiff Janssen's Answer to Defendant Teva's Counterclaim", Field for Case # 2:15-cv-05909-KM-JBC, Document No. 129, on Nov. 9, 2015, p. 1 of 9.

In the United States District Court for the District of New Jersey, *BTG International Limited, Janssen Biotech, Inc., et al.*, (Plaintiffs) vs. *Actavis Laboratories FL, Inc., et al.*, (Defendants), "Plaintiff Janssen's Answer to Defendant Sun's Counterclaim", Field for Case # 2:15-cv-05909-KM-JBC, Document No. 132, on Nov. 9, 2015, p. 1 of 9.

In the United States District Court for the District of New Jersey, *BTG International Limited, Janssen Biotech, Inc., et al.*, (Plaintiffs) vs. *Actavis Laboratories FL, Inc., et al.*, (Defendants), "Plaintiff Janssen's Answer to Defendant Hikma/West-Ward's Counterclaim", Field for Case # 2:15-cv-05909-KM-JBC, Document No. 131, on Nov. 9, 2015, p. 1 of 9.

In the United States District Court for the District of New Jersey, *BTG International Limited, Janssen Biotech, Inc., et al.*, (Plaintiffs) vs. *Actavis Laboratories FL, Inc., et al.*, (Defendants), "Plaintiff Janssen's Answer to Defendant DRL's Counterclaim", Field for Case # 2:15-cv-05909-KM-JBC, Document No. 130, on Nov. 9, 2015, p. 1 of 9.

In the United States District Court for the District of New Jersey, *BTG International Limited, Janssen Biotech, Inc., et al.*, (Plaintiffs) vs. *Actavis Laboratories FL, Inc., et al.*, (Defendants), "Plaintiff Janssen's Answer to Defendant Amneal's Counterclaim", Field for Case # 2:15-cv-05909-KM-JBC, Document No. 128, on Nov. 9, 2015, p. 1 of 9.

In the United States District Court for the District of New Jersey, *BTG International Limited, Janssen Biotech, Inc., et al.*, (Plaintiffs) vs. *Actavis Laboratories FL, Inc., et al.*, (Defendants), , Field for Case # 2:15-cv-05909-KM-JBC, Document No. 47, on Sep. 28, 2015, p. 1 of 114.

In the United States District Court for the District of New Jersey, *BTG International Limited Janssen Biotech Inc., et al.*, (Plaintiffs) vs. *Actavis Laboratories FL Inc., et al.*, (Defendants), "Second Amended Complaint for Patent Infringement", Case # 2:15-cv-05909-KM-JBC 114 pages.

In the United States District Court for the District of New Jersey, *BTG International Limited Janssen Biotech Inc., et al.*, (Plaintiffs) vs. *Actavis Laboratories FL Inc., et al.*, (Defendants), "First Second Amended Complaint for Patent Infringement", Case # 2:15-cv-05909-KM-JBC, 119 pages.

IMS Health Data 2012-2015 for Zytiga(Registered), Xtandi(Registered) and Jevtana(Registered).

Ian F. Tannock et al., "Chemotherapy With Mitoxantrone Plus Prednisone or Prednisone Alone for Symptomatic Hormone-Resistant Prostate Cancer: A Canadian Randomized Trial With Palliative End Points", Journal of Clinical Dncology, vol. 14, No. 6 (Jun. 1996): pp. 1756-1764.

I.G. Ron et al., "A low-dose adrenocorticotropin test reveals impaired adrenal function in cancer patients receiving Tiegestrol acetate therapy", European Journal of Cancer, filed for Case# IPR2016-00286, vol. 38,pp. 1490-1494, 2002.

I. A. Luthy et al., "Androgenic Activity of Synthetic Progestins and Spironolactone In Androgen-Sensitive Mouse Mammary Carcinoma (Shionogi) Cells in Culture", J. Steroid Biochem, vol. 31, No. 5 1988, pp. 845-852.

I Tannock,et al., "Treatment of metastatic prostatic cancer with low-dose prednisone: evaluation of pain and quality of life as pragmatic indices of response," Journal of Clinical Oncology, vol. 7, No. 590-597, May 1, 1989.

How Zytiga(Registered) (abiraterone acetate) Zytiga (Registered) Inhibits Androgen Production at 3 Sources-Including the Tumor Itself Works, https://www.zytiga.com/print/about-zytiga/how-zytiga-works (accessed Jul. 23, 2015).

Hotte and Saad, "Current management of castrate-resistant prostate cancer," Current Oncology—vol. 17, Supplement 2, S72-S79 2010 filed for Case # IPR2016-00286.

Herr and Pfitzenmaier, "Glucocorticoid use in prostate cancer and other solid tumours: implications for effectiveness of cytotoxic treatment and metastases," The Lancet Oncol, Filed for Case IPR2016-00286, Janssen Exhibit 2023, on May 2006, vol. 7 pp. 425-430.

Heremans GF, Moolenaar AJ, van Gelderen HH. Female phenotype in a male child due to 17-alpha-hydroxylase deficiency. Arch Dis Child., file for Case IPR2016-00286, Amerigen Exhibit 1167 on 1976, vol. 51, No. 9 pp. 121-723.

Hellerstedt B.A. et al., "The current state of hormonal therapy for prostate cancer", CA Cancer J. Clin., vol. 52: pp. 154-179, (2002).

Healthline, Prednisone vs. Prednisolone for Ulcerative Colitis, http://www.healthline.com/health/ulcerative-colitis/prednisone-vs-prednIsolone?ptint=true, Dec. 19, 2016, 3 pages.

Harris et al., "Low dose Ketoconazole with replacement doses of hydrocortisone in patients with progressive androgen Independent prostate cancer," The Journal of Urology, vol. 168, pp. 542-545, Aug. 2002.

Hadaschik et al., "Novel targets and approaches in advanced prostate cancer", Current Opinion in Urology 2007, vol. 17: pp. 182-187.

H.I. Scher et al., Design and End Points of Clinical Trials for Patients with Progressive Prostate Cancer and Castrate Levels of Testosterone: Recommendations of the Prostate Cancer Clinical Trials Working Group, Journal of Clinical Dncology, vol. 26, No. 7, at 1148-1159 (Mar. 1, 2008).

Grinspoon and Biller, "Clinical Review 62 Laboratory Assessment of Adrenal Insufficiency", Journal of Clinical Endocrinology and Metabolism, Filed for Case IPR2016-00286, Janssen Exhibit 2052, on 1994, vol. 79, No. 4, pp. 923-931.

Gordon Williams et al., "Objective Responses to Ketoconazole Therapy in Patients with Relapsed Progressive Prostatic Cancer" British Journal of Urology vol. 58, pp. 45-51 (1986).

Gerber G.S. et al., "Prostate specific antigen for assessing response to ketoconazole and prednisone in patients with hormone refractory metastatic cancer", Journal of Urology vol. 144 No. (5), Nov. 1990, pp. 1177-1179.

Gerard A. Potter et al., "Novel Steroidal Inhibitors of Human Cytochrome P450 17alpha (17alpha-Hyaroxylase-C1720-lyase): Potential Agents for the Treatment of Prostatic Cancer", Journal of Medicinal Chemistry, vol. 38, No. 13 1995 pp. 2463-2471.

Genentech Provides Update on Phase III Study of Avastin in Men With Late Stage Prostate Cancer Janssen Exhibit 2081, *Amerigen* vs. *Janssen* filed for Case # IPR2016-00286, Mar. 12, 2010, 3 Pages.

Garnick Deposition Blackhard, Letter to Editor, The Journal of Urology, "Official Journal of the American Urological Association, Inc.", file for Case IPR2016-01332, Janssen Exhibit 2011 on Dec. 1991, vol. 146, No. 6, pp. 1621-1622.

G. Sonpavde et al., Impact of single-agent daily prednisone on outcomes in men with metastatic castration-resistant prostate cancer, Prostate Cancer and Prostatic Diseases (2016) 00, pp. 1-5.

G. Attard et al., Phase I study of continuous oral dosing of an irreversible CYP17 inhibitor, abiraterone (A), in castration refractory prostate cancer (CRPC) patients (P) incorporating the evaluation of androgens and steroid metabolites in plasma and tumor, Journal of Clinical Oncology, vol. 25, No. 18S Jun. 20, 2007.

Food and Drug Administration, (FDA) letter approving Taxotere (May 19, 2004).

FDA Website, Orange Book, Zytiga (NDA 202379),http://www.accessdata.fda.gov/scripts/cder/ob/docs/patexclnew.cfm?Appl_No=202379&Product_No=001&table1=OB_Rx (accessed Jul. 24, 2015).

(56) References Cited

OTHER PUBLICATIONS

FDA Website, Orange Book, Zytiga (NDA 202379),"Orange Book: Approved Drug Products with Therapeutic Equivalence Evaluations" http://www.accessdata.fda.gov/scripts/cder/ob/docs/patexclnew.cfm?Appl_No=202379&Product_No=001&table1=OB_Rx (accessed Jun. 30, 2016).
FDA Website, Drugs@FDA : FDA Approved Drug Products,http://www.accessdata.fda.gov/scripts/cder/drugsaffda/index.cfm?fuseaction=Search_DrugDetails (accessed Jul. 23, 2015).
FDA News Release, "FDA expands Zytiga's use for late-stage prostate cancer," Dec. 10, 2012, http://www.fda.gov/NewsEvents/Newsroom/PressAnnouncements/ucm331492.htm.
Farwell, et al., "Total Suppression of Cortisol Excretion by Ketoconazole in the Therapy of the Ectopic Adrenocorticotropic Hormone Syndrome", American Journal of Medicine, filed for case IPR2016-00286, Janssen Exhibit 2065, on Jun. 1988, vol. 84, pp. 1063-1066.
Zytiga, "Orange Book: Approved Drug Products with Therapeutic Equivalence Evaluations", Amerigen 1035, Sep. 24, 2015, 2 pages.
Zytiga WebsiteHow Zytiga(Registered) (abiraterone acetate) Works, "Zytiga(Registered) Inhibits Androgen Production at 3 Sources— Including the Tumor Itself", https://www.zytiga.com/print/about-zytiga/how-zytiga-works (accessed Jun. 28, 2016).
Zytiga Website, About Zytiga(Registered) (abiraterone acetate), "Prescribed Oral Medication for Metastatic Castration-Resistant Prostate Cancer", https://www.zytiga.com/choosing-zytiga/results-of-zytiga (accessed Apr. 3, 2017), 10 pages.
Zytiga Usage-total promotional spend Janssen Exhibit 2096 *Amerigen vs. Janssen* filed for Case # IPR2016-00286, 3 Pgaes.
Zytiga Usage-prednisone information Janssen Exhibit 2095, *Amerigen vs. Janssen* filed for Case # IPR2016-00286.
ZYTIGA Market Share data, Janssen Exhibit 2134, *Mylan vs. Janssen* for Case # IPR2016-01332.
Zytiga Label, May. 20, 2015, Zytiga(Registered) (abiraterone acetate) Tablets for Oral Administration Initial U.S. Approval: 2011, May 2015, Mylan Pharms. Inc., Exhibit 1065, 30 pages.
Zytiga Brochure, Putting Prednisone in Perspective, "Prednisone reduces the incidence and severity of mineralocorticoid-related adverse reactions associated with Zytiga(Registered)", Janssen Biotech, Inc. Mar. 15, 2015.
ZYTIGA (Trademark) (abiraterone acetate) Tablets for Oral Administration Initial U.S. Approval Issued Apr. 2011, *Wockhardt vs. Janssen*, Filed for Case IPR2016-01582, Janssen Exhibit 2168, 22 pages.
Zafeiris Zaferiou et al. In Balaji, Chapter 9, Abiraterone for the Treatment of mCRPC , *Amerigen v. Janssen*, Case #IPR2016-00286, pp. 125-155.
Z. Zaferiou et al., Managing Metastatic Castration-Resistant Prostate Cancer in the Pre-chemotherapy Setting: A Changing Approach in the Era of New Targeted Agents, Drugs, 76:421-430, Feb. 12, 2016.
Yanase T et al., "17 alpha hydroxylase/17,20-lyase deficiency: from clinical investigation to molecular definition", Endocrine Revews 1991; vol. 12 No. 1 pp. 91-108.
Xiao-Yan Zhao et al., Glucocorticoids can promote androgen-independent growth of prostate cancer cells through a mutated androgen receptor, Nat Med vol. 6 No. 6, Jun. 2000, pp. 703-706.
Williams, "Discontinued Drugs in 2007: oncology drugs," Expert Opinion on Investigational Drugs, vol. 17 No. 12: pp. 1791-1816 (2008).
William D. Figg et al., "A Randomized Phase II Trial of Ketoconazole Plus Alendronate Versus Ketoconazole Alone in Patients With Androgen Independent Prostate Cancer and Bone Metastases", The Journal of Urology, vol. 173, pp. 790-796, Mar. 2005.
William Blair, Medivation, Inc. "Looking into Recent Weaknesses: Second-Quarter Preview and Breast Cancer Prospect; Lowering Price Target to $150 on Adjusting Share Count," Jul. 14, 2015.
William Blair, "Biotechnology—Zytiga Fourth-Quarter Sales Imply Xtandi Strength," Jan. 22, 2013.
Wiliam Meakin et al., Treatment of Metastatic Prostatic Cancer With Low-Dose Prednisone: Evaluation of Pain and Quality of Life as Pragmatic Indices of Response, Journal of Clinical Oncology, vol. 7, No. 5 May 1989, pp. 590-597.
White, P.C., "Synthesis and Metabolism of Corticosteroids," Principles and Practice of Endocrinology and Metabolism, Ed. Kenneth L. Becker, Philadelphia: Lippincott Williams & Wilkins, Janssen Exhibit 2086 *Amerigen vs. Janssen* for Case # IPR2016-00286, 2001, Chapter 72, 704-714.
What You Need to Know About Prostate Cancer, NIH Publication No. 23-1576 (2012) Janssen Exhibit 2091 *Amerigen vs. Janssen* filed for Case # IPR2016-00286.
Wells Fargo Securities, LLC., Equity Research, "Johnson & Johnson," Jun. 29, 2015.
Wedbush Quick Note, "Medivation: Zytiga Market Share Decline Accelerates From Last Quarter," Jul. 14, 2015.
W. H. J. Kruit et al. ,"Effect of combination therapy with aminoglutethimide and hydrocortisone on prostate-specific antigen response in metastatic prostate cancer refractory to standard endocrine therapy", Anti-Cancer Drugs, 2004, vol. 15, No. 9, pp. 843-847.
W. Berry et al., Phase III Study of Mitoxantrone Plus Low Dose Prednisone Versus Low Dose Prednisone Alone in Patients with Asymptomatic Hormone Refractory Prostate Cancer, The Journal of Urology, vol. 168, 2439-2443 (Dec. 2002).
Vivek K. Arora et al., Glucocorticoid Receptor Confers Resistance to Anti-Androgens by Bypassing Androgen Receptor Blockade, Cell. Dec. 5, 2013; 155(6): 1309-1322.
Vidal et al., "Reversing Resistance to Targeted Therapy", vol. 16—Supplement No. 4, 2004, pp. 7-12.
United States Patent and Trademark Office, Before the Patent Trial and Appeal Board, *Mylan Pharmaceuticals Inc* (Petitioners) vs. *Janssen Oncology, Inc.* (Patent Owner)for U.S. Pat. No. 8,822,438, "Petition for Inter Partes Review of U.S. Pat. No. 8,822,438", filed for Case IPR2016-01332, Jun. 30, 2016, 77 Pages.
United States Patent and Trademark Office, Before the Patent Trial and Appeal Board,*Amerigen Pharmaceuticals Limited*(Petitioner) vs. *Janssen Oncology, Inc.*(Patent Owner) for U.S. Pat. No. 8,822,438, "Methods and Compositions for Treating Cancer", 74 pages.
United States Patent and Trademark Office, Before the Patent Trial and Appeal Board, *Amerigen Pharmaceuticals Limited* vs. *Janseen Oncology, Inc.*, U.S. Pat. No. 8,822,438 B2, "Declaration of DeForest McDuff, Ph.D. in Support of Amerigen Pharmaceuticals Limited's Petition", filed for Case# IPR2016-00286, 44 pages.
United States Patent and Trademark Office, Before the Patent Trial and Appeal Board, *Amerigen Pharmaceuticals Limited* (Petitioner) vs. *Janssen Oncology, Inc.* (Patent Owner) for U.S. Pat. No. 8,822,438 B2, "Before Lora M. Green, Rama G. Elluru, and Kristina M. Kalan, Administrative Patent Judges.", filed for Case IPR2016-00286, Jul. 21, 2016, 6 Pages.
United States Patent and Trademark Office, Before the Patent Trial and Appeal Board, Wockhardt Bio AG (Petitioner), Janssen Oncology, Inc. (Patent Owner) for U.S. Pat. No. 8,822,438 B2, "Declaration of Matthew B. Rettig, M.D. in Support of Janssen Oncology, Inc.'s Patent Owner Response" filed for Case IPR2016-01582, Janssen Exhibit 2038.
United States Patent and Trademark Office, Before the Patent Trial and Appeal Board, *Wockhardt Bio AG* (Petitioner) vs. *Janssen Oncology, Inc.* (Patent Owner) for U.S. Pat. No. 8,822,438 B2, "Declaration of Richard Auchus, M.D., Ph.D. in Support of Janssen Oncology, Inc.'s Patent Owner Response" filed for Case IPR2016-01582, Janssen Exhibit 2040.
United States Patent and Trademark Office, Before the Patent Trial and Appeal Board, *Wockhardt Bio AG* (Petitioner) vs. *Janssen Oncology, Inc.* (Patent Owner) for U.S. Pat. No. 8,822,438 , "Declaration of Jennifer Reda in Support of Janssen Oncology Inc.'s Preliminary Response" filed for Case IPR2016-01582, Janssen Exhibit 2004 on Nov. 16, 2016, 3 pages.
United States Patent and Trademark Office, Before the Patent Trial and Appeal Board, *Mylan Pharmaceuticals, et al.* (Petitioners) vs. *Janssen Oncology, Inc.* (Patent Owner)for U.S. Pat. No. 8,822,438 B2, "Petitioners' Response to Patent Owner's Motion for Observations on Cross-Examination", filed for Case IPR2016-01332, May 10, 2017, 18 Pages.

(56) References Cited

OTHER PUBLICATIONS

United States Patent and Trademark Office, Before the Patent Trial and Appeal Board, *Mylan Pharmaceuticals, et al.* (Petitioners) vs. *Janssen Oncology, Inc.* (Patent Owner) for U.S. Pat. No. 8,822,438 B2, "Petitioners' Reply to Janssen's Patent Owner Response", filed for Case PR2016-01332, Apr. 19, 2017, 36 Pages.

United States Patent and Trademark Office, Before the Patent Trial and Appeal Board, *Mylan Pharmaceuticals, et al.* (Petitioners) vs. *Janssen Oncology, Inc.* (Patent Owner) for U.S. Pat. No. 8,822,438 B2, "Patent Owner's Motion for Observations on Cross-Examination", filed for Case PR2016-01332, May 3, 2017, 18 Pages.

United States Patent and Trademark Office, Before the Patent Trial and Appeal Board, *Mylan Pharmaceuticals Inc., et al.*, (Petitioner) vs. *Janssen Oncology, Inc.*, "Declaration of Ivan T. Hofmann, CPA/CFF, CPL.", Case # IPR2016-01332, U.S. Pat. No. 8,822,438, 5 pages.

United States Patent and Trademark Office, Before the Patent Trial and Appeal Board, *Mylan Pharmaceuticals Inc., et al.* (Petitioners) vs. *Janssen Oncology Inc.*, "Reply Declaration of Ivan T. Hofmann", Case # IPR2016-01332, U.S. Pat. No. 8,822,438, Mylan Pharms. Inc. 36 pages.

United States Patent and Trademark Office, Before the Patent Trial and Appeal Board, *Mylan Pharmaceuticals Inc., Actavis Laboratories FL, Inc., et al.*, (Petitioners) vs. *Janssen Oncology, Inc.*, "Declaration of Ivan T. Hofmann, CPA/CFF, CLP", Case # IPR2016-01332, U.S. Pat. No. 8,822,438, 3 pages.

United States Patent and Trademark Office, Before the Patent Trial and Appeal Board, *Mylan Pharmaceuticals Inc., Actavis Laboratories FL, Inc., et al.*, (Petitioners) vs. *Janssen Oncology, Inc.*, "Declaration of Bryan D. Beel", Case # IPR2016-01332, U.S. Pat. No. 8,822,438, 8 pages.

United States Patent and Trademark Office, Before the Patent Trial and Appeal Board, *Mylan Pharmaceuticals Inc., Actavis Laboratories FL, Inc., et al.*, (Petitioner) vs. *Janssen Oncology, Inc.*, "Reply Declaration of Ian McKeague, Ph.D. in Support of Petition for Inter Partes Review", for U.S. Pat. No. 8,822,438, Case IPR2016-01332, 56 pages.

United States Patent and Trademark Office, Before the Patent Trial and Appeal Board, *Mylan Pharmaceuticals Inc., Actavis Laboratories FL Inc., et al.*, (Petitioner) v. *Janssen Oncology Inc.*, "Reply Declaration of Marc B. Garnick M.D. in Support of Petition for Inter Partes Review", Case # IPR2016-013321, U.S. Pat. No. 8,822,438 B2, Mylan Pharms. Inc., 83 pages.

United States Patent and Trademark Office, Before the Patent Trial and Appeal Board, *Mylan Pharmaceuticals Inc.*, (Petitioner) vs. *Janssen Oncology Inc.*, "Declaration of Marc B Garnick M.D.", Case No. IPR2016-01332, U.S. Pat. No. 8,822,438, Mylan Pharms. Inc., 4 pages.

United States Patent and Trademark Office, Before the Patent Trial and Appeal Board, *Mylan Pharmaceuticals Inc.*, (Petitioner) vs. *Janssen Oncology Inc.*, "Declaration of Ivan T. Hofmann CPA/CFF CLP", Case # No. IPR2016-01332, U.S. Pat. No. 8,822,438, Mylan Pharms. Inc., 5 pages.

United States Patent and Trademark Office, Before the Patent Trial and Appeal Board, *Mylan Pharmaceuticals Inc. Actavis Laboratories FL Inc. et al.*, (Petitioner) vs. *Janssen Oncology Inc.*, "Reply Declaration of Ian McKeague Ph.D. in Support of Petition for Inter Partes Review", Case # IPR2016-01332, U.S. Pat. No. 8,822,438, Mylan Pharms. Inc., 55 pages.

United States Patent and Trademark Office, Before the Patent Trial and Appeal Board, *Mylan Pharmaceuticals Inc. Actavis Laboratories FL Inc. et al.*, (Petitioner) v. *Janssen Oncology Inc.*, "Reply Declaration of John Bantle M.D. in Support of Petition for Inter Partes Review", For U.S. Pat. No. 8,822,438, Case # IPR2016-01332, Mylan Pharms. Inc., 78 pages.

United States Patent and Trademark Office, Before the Patent Trial and Appeal Board, *Mylan Pharmaceuticals Inc.* (Petitioners) vs. *Janssen Oncology, Inc.*, (Patent Owner) for U.S. Pat. No. 3,822,438 B2, "Declaration of Richard Auchus, M.D., Ph.D. In Support of Janssen Oncology, Inc.'s Patent Owner Response" filed for Case IPR2016-01332, Janssen Exhibit 2040.

United States Patent and Trademark Office, Before the Patent Trial and Appeal Board, *Mylan Pharmaceuticals Inc.* (Petitioners) vs. *Janssen Oncology, Inc.* (Patent Owner) for U.S. Pat. No. 3,822,438 B2, "Declaration of Matthew B. Rettig, M.D. in Support of Janssen Oncology, Inc.'s Patent Owner Response" filed for Case # IPR2016-01332, Janssen Exhibit 2038.

United States Patent and Trademark Office, Before the Patent Trial and Appeal Board, Mylan Pharmaceuticals Inc. (Petitioners) Janssen Oncology, Inc. (Patent Owner) for U.S. Pat. No. 8,822,438 B2, "Declaration of Ian Judson, MD in Support of Janssen Oncology, Inc.'s Patent Owner Response" filed for Case IPR2016-01332, Janssen Exhibit 2028 on 2017, 6 pages.

United States Patent and Trademark Office, Before the Patent Trial and Appeal Board, Mylan Pharmaceuticals Inc. (Petitioner), Janssen Oncology, Inc. (Patent Owner) for U.S. Pat. No. 8,822,438 B2, "Patent Owner's Response", filed for Case IPR2016-01582, Janssen Exhibit 2154, on Mar. 8, 2017, 66 pages.

Clinical Cancer Research, "A Journal of the American Association for Cancer Research", Letter to Ian Judson, RE: "Manuscript# 030579, Hormonal impact of the 17a-hydroxylase/C17, 20-lyase inhibitor abiraterone acetate (CB7630) in patients with prostate cancer", Filed for case IPR2016-01332, Janssen Exhibit 2030, on May 12, 2003, 4 pages.

Cheol Kwak, et al., "Abiraterone acetate and prednisolone for metastatic castration-resistant prostate cancer failing androgen deprivation and docetaxel-based chemotherapy", International Journal of Urology (2014), vol. 21, pp. 1239-1244.

Charted—ChemoHormonal Therapy versus Androgen Ablation Randomized Trial for Extensive Disease in Prostate Cancer, Declararion of Christopher J. Sweeney, "Clinical Advances in Hematology and Oncology", filed for Case IPR2016-01582, Janssen Exhibit 2157, on Aug. 2006, vol. 4, No. 8, pp. 588-590.

Charles L. James et al., "Antimicrobial Therapy, in Trauma Critical Care", vol. 2, (William C. Wilson et al. eds., 2007), pp. 927-960.

Charles J. Ryan et al., Phase I evaluation of abiraterone acetate (CB7630), a 17 alpha hydroxyiase C17,20-Lyase Inhibitor in androgen-independent prostate cancer (AIPC), Journal of Clinical Oncology, vol. 25, No. 18S Jun. 20, 2007.

Charles J. Ryan et al., "Phase I clinical trial of the CYP17 inhibitor abiraterone acetate demonstrating clinical activity in patients with castration-resistant prostate cancer who received prior ketoconazole therapy", Journal of Clinical Oncology Mar. 20, 2010, vol. 28, No. 9, pp. 1481-1488.

Charles J. Ryan et al., "Abiraterone in Metastatic Prostate Cancer without Previous Chemotherapy", The new england journal of medicine, vol. 368, pp. 138-148, Jan. 10, 2013.

Centers for Disease Control and Prevention, "Prostate Cancer" Janssen Exhibit 2100, *Amerigen* vs. *Janssen* filed for Case # IPR2016-00286, 2 Pages.

Carducci et al., "A Phase 3 Randomized Controlled Trial of the Efficacy and Safety of Atrasentan in Men With Metastatic Hormone-refractory Prostate Cancer," vol. 110, No. 9, Nov. 1, 2007, pp. 1959-1966.

Canger.gov (NIH NCI), "Prostate-specific antigen (PSA) test," https://www.cancergov/types/prostate/psa-fact-sheet (accessed Apr. 11, 2017), 8 pages.

Cancer.org (ACS), "What are the key statistics about prostate cancer?", http://www.cancer.org/cancer/prostatecancer/detailedguide/prostat e-cancer-key-statistics (accessed Jun. 28, 2016), Mylan Pharms. Inc., Exhibit 1041, 2 pages.

Cancer.org (ACS), "Hormone therapy for prostate cancer," https://www.cancer.org/conten/cancer/en/cancer/prostatecancer/treating/hormone-therapy.html (accessed Apr. 10, 2017), 11 pages.

Cancer.net (ASCO Patient Website), "Treatment of Metastatic Castration-Resistant Prostate Cancer Sep. 8 2014", http://www.cancer.net/research-and-advocacy/asco-care-andtreatment- recommendations-patients/treatment-metastaticcastration- resistant-prostate-cancer (accessed Jun. 28, 2016), 4 pages.

Cancer.Net "Treatment of Metastatic Castration-Resistant Prostate Cancer" filed for Case # IPR2016-00286 on Sep. 8, 2014 3 pages.

(56) References Cited

OTHER PUBLICATIONS

Cancer.gov (NIH NCI), "Metastatic cancer," https://www.cancer.gov/types/metastatic-cancer (accessed Oct. 3, 2016), pp. 3 for Case # IPR2016-00286.

Cancer.gov (NIH NCI), "Metastatic cancer," https://www.cancer.gov/about-cancer/treatment/drugs/docetaxel (accessed Oct. 3, 2016), pp. 3 for Case # IPR2016-01332.

C.W. Ryan et al., "Dose-Ranging Study of the Safety and Pharmacokinetics of Atrasentan in Patients with Refractory Malignancies", Clinical Cancer Research, filed for IPR2016-00286, vol. 10, pp. 4406-4411, Jul. 1, 2004.

C.N. Sternberg et al., Phase III Trial of Satraplatin, an Oral Platinum plus Prednisone vs. Prednisone alone in Patients with Hormone-Refractory Prostate Cancer, Oncology, 68, pp. 2-9 (2005).

C.J. Ryan et al., Abiraterone in Metastatic Prostate Cancer without Previous Chemotherapy, The New England Journal of Medicine, 368; 2, pp. 138-148 (Jan. 10, 2013).

C.J. Ryan et al., "Abiraterone acetate plus prednisone versus placebo plus prednisone in chemotherapy-naive men with metastatic castration-resistant prostate cancer (COU-AA-302): final overall survival analysis of a randomised, double-blind, placebo-controlled phase 3 study", The Lancet, filed for Case# IPR2016-00286, vol. 16, pp. 152-160, Feb. 2015.

Burgess and Roth et al., "Changing Perspectives of the Role of Chemotherapy in Advanced Prostate Cancer," urologic Clinics of North America 2006, filed for Case IPR2016-00286, Janssen Exhibit 2007, vol. 33, pp. 227-236.

Bubley et al., "Eligibility and Response Guidelines for Phase II Clinical Trials in Androgen-Independent Prostate Cancer: Recommendations From the Prostate-Specific Antigen Working Group", Journal of Clinical Oncology, file for case IPR2016-00286, Janssen Exhibit 2057, on Nov. 1999, vol. 17, No. 11, pp. 3461-3467.

BTG Webpage from WayBack Machine dated Feb. 11, 2002, http://web.archive.org/web/20020211122029/http:/www.btgplc.com/portfolio_available/index.html.

BTG Press Release, "BTG licenses new prostate cancer drug to Cougar Biotechnology," Apr. 20, 2004, http://www.ptgplc.com/media/press-releases/btg-licenses-newprostate-cancer-drug-to-cougar-biotechnology (accessed Apr. 3, 2017), 2 pages.

BTG Annual Report, 2004, Filed for Case *Wockhardt* v. *Janssen* IPR2016-01332, Janssen Exhibit 2138, 60 pages.

BTG Annual Report, 2003, "Commercialising high-value technologies", *Mylan* v. *Janssen*, for Case # IPR2016-01332, Janssen Exhibit 2137, 60 pages.

Brooke et al., "A novel point mutationin P450c17 (CYP17) causing combined 17alpha-hydroxylase/17,20-lyase deficiency", The Journal of Clinical Endocrinology & Metabolism, 2006, vol. 91 No. 6 pp. 2428-2431.

Boumpas et al., "Glucocorticoid Therapy for Immune-mediated Diseases: Basic and Clinical Correlates," Annals of Internal Medicine, Filed for Case IPR2016-00286, Janssen Exhibit 2021 on Dec. 15, 1993, vol. 119, No. 12 1198-1208.

Borner et al., "Answering Patients' Needs", Oral Alternatives to Intravenous Therapy, The Oncologist 2001 vol. 6, suppl 4, pp. 12-16.

Booth et al., "Oncology's trials," Nature Reviews, vol. 2: Aug. 2003, pp. 609-610.

Boehringer-Ingelheim—Newspage "New Treatment for Prostate Cancer Under Development," Filed for Case IPR2016-00286, Janssen Exhibit 2013 on May 22, 1996, 1 page.

Blackard, "Letters to the Editor," Journal of Urology, Re: Prostate Specific Antigen for Assessing Response to Ketoconazole and Prednisone in Patients With Hormone Refractory Metastatic Prostate Cancer, Filed for Case IPR2016-00286, Janssen Exhibit 2049, on Dec. 1991, vol. 146, No. 6, pp. 1621-1622.

Biglieri EG et al., "Herron MA, Brust N. 17-hydroxylation deficiency in man", Journal of Clinical Investigation 1966, vol. 45 No. 12, pp. 1946-1954.

Biff F. Palmer, "Managing Hyperkalemia Caused by Inhibitors of the Renin—Angiotensin—Aldosterone System", New England Journal of Medicine, file for Case IPR2016-01332, Janssen Exhibit 2067 on Aug. 5, 2004, vol. 351, No. 6, pp. 585-592.

Bernard P. Schimmer and Keith L. Parker, Andrenocorticotropic Hormone: Adrenocortical Steroids and Their Synthetic Analogs; Inhibitors of the Synthesis and Actions of Adrenocortical Hormones, in Goodman & Gilman's The Pharmacological Basis of Therapeutics , (10th ed. 2001), pp. 1649-1677.

Balaji, Managing Metastatic Prostate Cancer in Your Urological Oncology Practice (2016).

B. A. J. Ponder et al., "Response to aminoglutethimide and cortisone acetate in advanced prostatic cancer", Br. J. Cancer, (1984) 50 ,pp. 757-763.

Austin and Hux, "A Brief note on overlapping confidence intervals", *Mylan* vs. *Janssen*, Filed for Case IPR2016-01332, Janssen Exhibit 2184, on 2002, Journal of Vascular Surgery, vol. 36, No. 1, 194-195 pages.

Auerbach et al., United States Patent and Trademark Office , Before the Patent Trial and Appeal Board, Amerigen Pharmaceuticals Limited and Argentum Pharmaceuticals LLC (Petitioners), Janssen oncology, Inc. (Patent Owner) for Patent# 8,822,438, "Methods and Compositions for Treating Cancer", filed for Case IPR2016-01582, Amerigen Exhibit 2019 Issued on Sep. 2, 2014, 13 pages.

Auchus, R.J. "The genetics, pathophysiology, and management of human deficiencies of P450c17," Endocrinology and Metabolism. Clinics of North America. vol. 30, No. 1, pp. 101-119, Mar. 2001.

Auchus RJ et al., "Use of prednisone with abiraterone acetate in metastatic castration-resistant prostate cancer", The Oncologist 2014, vol. 19 No. 12, pp. 1231-1240.

Attard, Poster: A randomized trial of abiraterone acetate (AA) administered with 1 of 4 glucocorticoid (GC) regimens in metastatic castration-resistant prostate cancer (mCRPC) patients (pts), J. Clin Oncol 34, 2016 (Suppl 2S: abstr 261). pp. 1-4, Nov. 15, 2016.

Attard G. et al., "Selective blockade of androgenic steroid synthesis by novel lyase inhibitors as a therapeutic strategy for treating metastatic prostate cancer", Br. J. Urol. vol. 96 No. (9): pp. 1241-1246 (2005).

Attard G et al., "Clinical and biochemical consequences of CYP17A1 inhibition with abiraterone given with and without exogenous glucocorticoids in castrate men with dvanced prostate cancer", Journal of Clinical Endocrinol Metab Feb. 2012, vol. 97 No. 2 pp. 507-516.

Attard et al., "Selective Inhibition of CYP17 With Abiraterone Acetate Is Highly Active in the Treatment of Castration-Resistant Prostate Cancer," Journal of Clinical Oncology, Filed for Case IPR2016-00286, Janssen Exhibit 2015, vol. 27, No. 23, on August 10, 2009, pp. 3742-3748.

Attard et al., "Phase I Clinical Trial of a Selective Inhibitor of CYP17, Abiraterone Acetate, Confirms That Castration-Resistant Prostate Cancer Commonly Remains Hormone Driven," Journal of Clinical Oncology, Filed for Case IPR2016-00286, Janssen Exhibit 2014, vol. 26, No. 28, on Oct. 1, 2008, pp. 4563-4571.

Armstrong and Carducci, "New drugs in prostate cancer," Current Opinions Urology, 2006, Filed for Case IPR2016-00286, Janssen Exhibit 2011, vol. 16, pp. 138-145.

Arlt, W. et al., "Adrenal insufficiency," Lancet, vol. 361 • May 31, 2003, pp. 1881-1893.

Antonarakis and Eisenberger, "Phase III Trials With Docetaxel-Based Combinations for Metastatic Castration-Resistant Prostate Cancer: Time to Learn From Past Experiences" Journal of Clinical Oncology, vol. 31, No. 14. May 10, 2013: pp. 1709-1712.

Antifungal Treatment Should Be Taken Off the Market, Public Citizen Tells FDA filed for Case # IPR2016-01582 on Feb. 24, 2015 1page.

Seale and Compton, "Side-effects of corticosteroid agents", The Medical Journal of Australia vol. 144, No. 3 Feb. 3, 1986 pp. 139-142.

Schulte et al., The corticotropinreleasing hormone stimulation test: a possible aid in the evaluation of patients with adrenal insufficiency. Journal of Clinical Endocrinology Metabolism 1984, vol. 58 No. 6, pp. 1064-1067.

Scher H.I. et al., "Increased survival with enzalutamide in prostate cancer after chemotherapy", New Eng. J. Med., vol. 367 No. 13, Sep. 27 2012, pp. 1187-1197.

(56) References Cited

OTHER PUBLICATIONS

Scher et al., "Bicalutamide for Advanced Prostate Cancer: The Natural Versus Treated History of Disease", Journal of Clinical Oncology, file for Case IPR2016-00286, Janssen Exhibit 2055, vol. 15, No. 8 on Aug. 1997, pp. 2928-2938.
S. Wilkinson, S. and G. Chodak., "An Evaluation of Intermediate-Dose Ketoconazole in Hormone Refractory Prostate Cancer," European Urology, vol. 45, pp. 581-585, Nov. 26, 2004.
S. Udhane et al., Specificity of Anti-Prostate Cancer CYP17A1 Inhibitors on Androgen Biosynthesis, Biochemical and Biophysical Research Communications,filed for Case# IPR2016-00286, vol. 477, pp. 1005-1010, (Elsevier 2016).
S. Oudard et al., Prostate-Specific Antigen Doubling Time Before Onset of Chemotherapy as a Predictor of Survival for Hormone-Refractory Prostate Cancer Patients, Annals of Oncology vol. 18, pp. 1828-1833, (Nov. 2007).
S. M. Wilhelm et al., "BAY 43/9006 Exhibits Broad Spectrum Oral Antitumor Activity and Targets the RAF/MEK/ERK Pathway and Receptor Tyrosine Kinases Involved in Tumor Progression and Angiogenesis", Cancer Research,filed for Case# IPR2016-00286, vol. 64, pp. 7099-7109, (Oct. 1, 2004).
S. Halabi et al., Prostate-Specific Antigen Changes As Surrogate for Overall Survival in Men With Metastatic castration-Resistant Prostate Cancer Treated With Second-Line Chemotherapy, Journal of Clinical Oncology, vol. 31, No. 31, pp. 3944-3950 (Nov. 1, 2013).
S. E. Barrie et al., "Pharmacology of Novel Steroidal Inhibitors of Cytochrome P450 17alpha (17alpha-Hydroxylase/C17-20 Lyase)", J. Steroid Biochem. Molec. Biol., vol. 50 No. 5/6, pp. 267-273. 1994.
S. D. Fosso et al. ,"Flutamide Versus Prednisone in Patients With Prostate cancer Symptomatically Progressing After Androgen-ablative Therapy: A Phase iii Study of the European Organization for Research and Treatment of Cancer Genitourinary Group", journal of Clinical Oncology, vol. 19, No. 1 Jan. 1, 2001, pp. 62-71.
Ryan et al., "Phase II Study of Abiraterone in Chemotherapy-Naive Metastatic Castration-Resistant Prostate Cancer Displaying Bone Flare Discordant with Serologic Response", Clinical Cancer Research, 2011, Filed for Case IPR2016-00286, Janssen Exhibit 2017, vol. 17, No. 14, pp. 4854-4861.
Rumohr et al., "Current Chemotherapeutic approaches for androgen-independent prostate cancer", Current Opinion in Investigational Drug, Filed for Case IPR2016-01332, Janssen Exhibit 2027, on 2006, vol. 7, No. 6, pp. 529-533.
Ruben H. Munoz, Akin Gump Strauss Hauer & Feld LLP, "Zytiga IPR", Mailed for Case# IPR2016-00286, Jun. 29, 2016, 1 page.
Robert Twycross, "Corticosteroids in Advanced Cancer",filed for Case# IPR2016-00286, vol. 305, pp. 969-970, Oct. 24, 1992.
Richard J. Auchus, "Steroid 17-hydroxylase and 17,20-lyase deficiencies, genetic and pharmacologic", Journal of Steroid Biochemistry & Molecular Biology, 2017, vol. 165, pp. 71-78.
Remington—The Science and Practice of Pharmacy, 20th Edition, filed for Case IPR2016-00286, Janssen Exhibit 2003 on 2000, pp. 1363-1370.
RBC Capital Markets, "Xtandi Beats Casodex, Set to Top Zytiga," Apr. 3, 2015, http://online.barrons.com/articles/xtandi-beats-casodexset-to-topzytiga-1428075331 (accessed Jul. 24, 2015).
R. Venkitaraman et al., A Randomised Phase 2 Trial of Dexamethasone Versus Prednisolone in Castration-resistant Prostate Cancer, European Urology, 67, pp. 673-679 (2015).
R. De Coste et al., "Effects of high-dose ketoconazole and dexamethasone on ACTH-stimulated adrenal steroidogenesis in orchiectomized prostatic cancer patients", Acta Endocrinologica (Copenh), 1987 155: pp. 265-271.
Public Citizen Press Room Release—"Antifunal Treatment Should Be Taken Off the Market, Public Citizen Tells FDAD," Filed for Case IPR2016-00286, Janssen Exhibit 2019, on Feb. 24, 2015, 1 page.
Prostate Cancer End Points Workshop Jun. 21-22, 2004, Bethesda Marriott—Bethesda MD, 66 pages.

PMLiVe Website, "Top 50 Pharmaceutical Products by Global Sales", http://www.pmlive.com/top pharma list/Top 50 pharmaceutical products by global sales (accessed Jun. 30, 2016), Mylan Pharms. Inc., Exhibit 1055, 3 pages.
Petrylak et al., "Docetaxel and Estramustine Compared with Mitoxantrone and Prednisone for Advanced Refractory Prostate Cancer", New England Journal of Medicine, file for Case IPR2016-00286, Janssen Exhibit 2059, on Oct. 7, 2004, vol. 351, No. 15, pp. 1513-1520.
Patrick Therasse et al., "New Guidelines to Evaluate the Response to Treatment in Solid Tumors", Journal of the National Cancer Institute, vol. 92, No. 3, Feb. 2, 2000, pp. 205-216.
Patient Affordability, "Protective Order Material" Janssen Exhibit 2093, *Amerigen* vs. *Janssen*, filed for Case # IPR2016-00286, Nov. 6, 2013.
Patent Owner Janssen Oncology, Inc., for U.S. Pat. No. 8,822,438, *Mylan* vs. *Janssen*, filed for case IPR2016-01332, Janssen Exhibit 2189, 86 pages.
Papatsoris et al., "Novel Biological Agents for the Treatment of Hormone-Refractory Prostate Cancer (HRPC)", Current Medicinal Chemistry 2007, filed for Case IPR2016-00286, Janssen Exhibit 2010, vol. 12, pp. 277-296.
P. M. Clark et al., "Defining the normal cortisol response to the short Synacthen test", Implications for the investigation of hypothalamic-pituitary disorders,Clinical Endocrinology 1998 vol. 49 pp. 287-292.
Ospina et al., "ACTH Stimulation Tests for the Diagnosis of Adrenal Insufficiency: Systematic Review and Meta-Analysis", The Journal of Clinical Endocrinology & Metabolism Feb. 2016, vol. 101 No. 2 pp. 427-434.
Orange Book, "Xtandi,", Approved Drug Products with Therapeutic Equivalence Evaluations, https://www.accessdata.fda.gov/scripts/cder/ob/patent_info.cfm? Product_No=001&Appl_No=203415 &Appl_type=N. html.
Oliver Sartor et al., "Effect of Prednisone on Prostate-Specific Antigen in Patients With Hormone-Refractory Prostate Cancer", Urology, 52: 1998, pp. 252-256.
Oh W.K., "Secondary hormonal therapies in the treatment of prostate cancer", Urology 60(Supp. 3A): pp. 87-93, (Sep. 2002).
Offiecial Journal of the American Urological Association, Inc., "The Journal of Urology", vol. 135, No. 4, part 2, filed for Case IPR2016-00286, Janssen Exhibit 2022 on Apr. 1986, 203A pages, Abstract 397.
Official Journal of the American Urological Association, "Postate Cancer", Journal Urology, vol. 177, No. 4, Apr. 2007, 2 pages.
Oelkers W. et al., Dose-response relationships between plasma adrenocorticotropin (ACTH), cortisol, aldosterone, and 18-hydroxycorticosterone after injection of ACTH-(1-39) or human corticotropin-releasing hormone in man, Journal of Clinical Endocrinology Metabolism, 1988, vol. 66, No. 1, pp. 181-186.
O'Donnell, A. et al., "Hormonal impact of the 17(Alpha)-hydroxylase/C17-20-lyase inhibitor abiraterone acetate (CB7630) in patients with prostate cancer," British Journal of Cancer, vol. 90, pp. 2317-2325, 2004.
New Treatment for Prostate Cancer Under Development May 22, 1996 filed for Case # IPR2016-01582.
NCT01867710 Clinicaltrials.gov, "A Randomized Phase 2 Study Evaluating Abiraterone Acetate With Different Steroid Regimens for Preventing Symptoms Associated With Mineralocorticoid Excess in Asymptomatic, Chemotherapy-naïve and Metastatic Castration-resistant Prostate Cancer (mCRPC) Patients" file for Case IPR2016-00286, Amerigen Exhibit 1187, on Jan. 14, 2017, 4 pages.
National Cance Institute-Seer Stat Fact Sheets: Prostate Cancer Janssen Exhibit 2089, *Amerigen* vs. *Janssen* filed for Case # PR2016-00286, Oct. 3, 2016, pp. 1-11.
N. Romero-Laorden et al., Prospective Evaluation of the Response to Prednisone-Dexamethasone Switch in castration-Resistant Prostate Cancer Patients Treated with abiraterone pre-and post-docetaxel, Journal of Clinical Oncology vol. 34, Nov. 14, 2016.
Murphy W.J. J.L. Orcutt & P.C. Remus (2012) Patent Valuation: Improving Decision Making through Analysis Hoboken NJ: Wiley.

(56) References Cited

OTHER PUBLICATIONS

Mulcahy, "Phase 3 Trial of Immunotherapy for Metastatic Prostate Cancer Terminated" Janssen Exhibit 2082 *Amerigen* vs. *Janssen* for Case # IPR2016-00286, Oct. 17, 2008, 2 Pages.

Millikan, et al., "Randomized phase 2 trial of ketoconazole and ketoconazole/doxorubicin in androgen independent prostate cancer", Urologic Oncology, tile for Case IPR2016-00286, Janssen Exhibit 2064, on 2001, vol. 6, pp. 111-115.

Michaelson et al., "Randomized, Placebo-Controlled, Phase III Trial of Sunitinib Plus Prednisone Versus Prednisone Alone in Progressive, Metastatic, Castration-Resistant Prostate Cancer," Journal of Clinical Oncology, vol. 31. pp. 1-8, (2013).

Melby JC et al., "Comparative studies on adrenal cortical function and cortisol metabolism in healthy adults and in patients with shock due to infection", Journal Clin Invest 1958, vol. 37 No. 12 pp. 1791-1798.

MedlinePlus, "ACTH stimulation test", Available at https://medlineplus.gov/ency/article/003696.htm, last visited Sep. 30, 2016, file for Case IPR2016-00286, Janssen Exhibit 2050, 4 pages.

Medivation Press Release, "U.S. FDA Approves New Indication for the Use of XTANDI (Registered) (Enzalutamide) Capsules for Patients With Metastatic Castration-Resistant Prostate Cancer," Sep. 10, 2014, http://investors.medivation.com/releasedetail.cfm?ReleaseID=870267.

Medical Dictionary, "Refractory cancer definition of refractory cancer by Medical dictionary" Janssen Exhibit 2103 *Amerigen* vs. *Janssen* filed for Case # IPR2016-00286, Oct. 3, 2016, 1 page.

Mayo Clinic Website, "Prostate cancer", http://www.mayoclinic.org/diseasesconditions/prostatecancer/basics/definition/con-20029597?p=1 (accessed Jun. 28, 2016), Mylan Pharms. Inc., Exhibit 1051, 11 pages.

Nishiyama, et al., Hormone/Antihormone Withdrawal and Dexamethasone for Hormone-Refractory Prostate Cancer, International Journal of Urology, Mar. 10, 1997, vol. 5, 44-47.

Nishimura, et al., Potential Mechanism for the Effects of Dexamethasone on Growth of Androgen-Independent Prostate Cancer, Journal of the National Cancer Institute, Nov. 21, 2001, vol. 93, No. 22, 1739-1746.

Stein, et al., Randomized Phase 2 Therapeutic Equivalence Study of Abiraterone Acetate Fine Particle Formulation vs. Originator Abiraterone Acetate in Patients With Metastatic Castration-Resistant Prostate Cancer: The STAAR Study, Urologic Oncology: Seminars and Original Investigations, 36, 2018, 81.e9-81.e16.

Loose, D.S., et al., "Ketoconazole Blocks Andrenal Steroidogenesis by inhibiting Cytochrome P450-dependent Enzymes", J. Clin. Invest., 71, (1983) pp. 1495-1499.

Logothetis et al., "Identification of an androgen withdrawal responsive phenotype in castrate resistant prostate cancer (CRPC) patients (pts) treated with abiraterone acetate (AA)," J. Clin. Oncol. (Meeting abstracts), vol. 26 (May 20 Supplement), abstract No. 5017 (2008).

Ling et al., "17-imidazolyl, pyrazolyl, and isoxazolyl androstene derivatives. Novel steroidal inhibitors of human cytochrome C17,20-lyase (P45017alpha)," J. Med. Chem., vol. 40:3297-3304 (1997).

Leo Pharma Licenses Rights to Seocalcitol to Cougar Biotechnology http://www.mediconvalley.com/NewsAndEvents/News/LeoPharma%20Licenses%20Rights (2005).

Lam et al., "Secondary Hormonal Therapy for Advanced Prostate Cancer," J Urology, vol. 175(1):27-34 (2006).

Koshizuka et al., "Combined effect of vitamin D3 analogs and paclitaxel on the growth of MCF-7 breast cancer cells in vivo," Breast Cancer Research and Treatment, Springer, New York, NY, vol. 53(2):113-120 (1999).

Kissmeyer, A.M. et al., "The Tissue-specific Distribution of 3H-Seocalcitol (EB 1089) and 3H-calcitriol in Rats", J. of Steroid Bioch. & Mol. Biol. 89-90: 43-47 (2004).

Kaye et al., "New Drug Treatment for Cancer in 2007—Real Progress at Last?" EJC Supplements, vol. 5(4):35, 14th European Cancer Conference, abstract No. 126 (2007).

Jhun et al., "Gene expression signature of Gleason score is associated with prostate cancer outcomes in a radical prostatectomy cohort", Oncotarget, Jun. 2017, vol. 8, No. 26, pp. 43035-43047.

Jemal, A., et al, "Cancer Statistics, 2007", CA Cancer J Clin, 57, (2007) pp. 43-66.

Jarman et al., "The Mechanism of Irreversible Inhibition of Human Cytochrome P45017alpha by Abiraterone, a Potential New Drug for the Treatment of Prostate Cancer," Annals of Oncol.), vol. 9(Suppl. 2):135, 10th NCI-EORTC Symposium on New Drugs in Cancer Therapy, abstract No. 516 (1998).

Jarman et al., "The 16,17-Double Bond is Needed for Irreversible Inhibition of Human Cytochrome P45017alpha by Abiraterone (17-(3-Pyridyl)androsta-5, 16-dien-3Beta -ol) and Related Steroidal Inhibitors," J. Med. Chem., vol. 41:5375-5381 (1998).

Jarman et al., "Enzyme Inhibitors in Endocrinology," J. Endocrinology, vol. 148 (Suppl.), abstract No. S23 (1996).

Jakobsen et al., "Medroxyprogesterone Acetate and Prednisone in Advanced Breast Cancer. A Randomized Trial," Eur. J Cancer Clin. Oncol., vol. 22:9, pp. 1067-1072 (1986).

Isaacs et al., Identification of ABR-215050 as lead second generation quinoline-3-carboxamide anti-angiogenic agent for the treatment of prostate cancer, The Prostate, Dec. 2006, vol. 66, No. 16, pp. 1768-1778.

Internet article: http://clinicaltrials.gov/ct2/show/study/NCT00485303?sec=X501, 2014.

Internet article: http://clinicaltrials.gov/archive/NCT00485303/2007.sub.-06.sub.-11.

International Search Report, PCT/US2007/018769, filed Aug. 23, 2007.

International Search Report for International Application No. PCT/US2008/008540, filed Jul. 11, 2008.

International Preliminary Report on Patentability dated Jan. 21, 2010 for International Application No. PCT/US2008/008540.

International Application No. PCT/US2007/018770, filed Aug. 23, 2007 document entitled: "Annex to Form PCT/ISA/206, Communication Relating to the Results of the Partial International Search". Information concerning Zytiga (abiraterone acetate) from http://www.kompendium,ch/prod/pnr/1183238/de?Plafform=Desktop as of Mar. 25, 2014.

Huggins, Charles, et al. Studies on Prostatic Cancer.l. The Effect of Castration, of Estrogen and of Androgen Injection on Serum Phosphatases in Metastatic Carcinoma of the Prostate, Cancer Research, 1941, pp. 293-297, vol. 1.

Huggins, C., et al, "Studies on Prostatic Cancer. I. The Effect of Castration, of Estrogen and Androgen Injection on Serum Phosphatases in Metastatic Carcinoma of the Prostate", Cancer Res, 22(4), (1972) pp. 232-240.

Hsieh et al., "Novel Concepts in Androgen Receptor Blockade," The Cancer Journal (Jan./Feb. 2008), vol. 14(1):11-14.

Horsham, Pa., Dec. 10, 2012—U.S. FDA Approves Expanded ZYTIGA (Registered) Indication for Treatment of Metastatic Castration-Resistant Prostate Cancer Johnson & Johnson, Services, Inc. 1997-2017, 5 pages.

Hildesheim, "Prostate cancer pill extends life", Lancastria.net, May 26, 2011, 5 pages.

Higlights of Alimta prescribing information.

Highlights of Zytiga Prescribing Information, 2018.

Highlights of Zytiga Prescribing Information, 2015.

Highlights of Xtandi Prescribing Information, 2015.

Highlights of Rayos Prescribing Information, 2012.

Highlights of Jevtana Prescribing Information, 2010.

Highlights of Amneal AA prescribing information.

Hellerstedt et al., "The current state of hormonal therapy for prostate cancer", CA A Cancer Journal for Clinicians, May-Jun. 2002, vol. 52, No. 3, pp. 154-179.

Haynes et al., "Pharmacology of CB7598, a Highly Potent Inhibitor of Cytochrome P450c17," Proceedings American Association for Cancer Research, vol. 35, Eighty-fifth Annual Meeting, abstract No. 2507 (1994).

Harzstark et al., "Therapies in Development for Castrate-Resistant Prostate Cancer," Expert Rev. Anticancer Ther., vol. 8(2):259-268 (2008).

(56) References Cited

OTHER PUBLICATIONS

Harzstark et al., "Novel Therapeutic Strategies in Development for Prostate Cancer," Expert Opin. investig. Drugs, vol. 17(1):13-22 (2008).
Hartmann et al., "Synthesis and evaluation of novel steroidal oxime inhibitors of P450 17 (17alpha-hydroxylase/Cm17-20-lyase) and 5alpha-reductase types 1 and 2," J. Med. Chem., vol. 43:4266-4277 (2000).
Harrison's 15th Edition Principles of Internal Medicine, Braunwald Fauci Kasper Hauser Longo Jameson, N Engl J. Med. 341 : 156, 1999.
Hansen. C. M. et al., "Seocalcitol (EB 1089): A Vitamin D. Analogue of Anti-Cancer Potential, Background, Design, Synthesis, Pre-Clinical and Clinical Evaluation", 6 Current Pharmaceutical Design, 803-828 (2000).
Hakki et al, CYP17- and CYP11B-dependent steriod hydroxylases as drug development targets, Elsevier, 2006, pp. 27-52, vol. 11.
Haidar et al., "Novel steroidal pyrimidyl inhibitors of P450 17 (17alpha-hydroxylase/C17-20-lyase)," Arch. Pharm. Pharm. Med. Chem., vol. 334:373-374 (2001).
Haidar et al., "Effects of novel 17alpha-hydroxylase/C17.20-lyase (P450 17, CYP 17) inhibitors on androgen biosynthesis in vitro and in vivo," J. Steroid Bioch. & Mol. Biol., vol. 84:555-62 (2003).
Haidar et al., "Effects of novel 17alpha-hydroxylase/C17, 20-lyase (P450 17, CYP 17) inhibitors on androgen biosynthesis in vitro and in vivo", Journal of Steroid Biochemistry & Molecular Biology, Apr. 2003, vol. 84, No. 5, pp. 555-562.
Grove, M. et al., "Bioavailability of Seocalcitol i: Relating Solubility in Biorelevant Media with Oral Bioavailability in Rats-Effect of Medium and Long Chain Triglycerides", 94(8) J. Pharm. Sci. No. 1830-1838 (2005).
Gleave et al., "Use of antisense oligonucleotides targeting the cytoprotective gene, clusterin, to enhance androgen-and chemosensitivity in prostate cancer", World J Urol. Feb. 2005, vol. 23, No. 1, pp. 38-46.
Gill et al., "Efficacy of Eplerenone in the Management of Mineralocorticoid Excess in Men With Metastatic Castration-resistant Prostate Cancer Treated With Abiraterone Without Prednisone", Clinical Genitourinary Cancer, vol. 15, No. 4, Aug. 2017, pp. e599-e602.
Gignac et al., "Castration Resistant, Taxane Naive Metastatic Prostate Cancer: Current Clinical Approaches and Future Directions," J. Urology, vol. 178:S30-S35 (2007).
Ghatalia et al., "Effect of Single-agent Daily Prednisone on Outcomes and Toxicities in Metastatic Castration-resistant Prostate Cancer: Pooled Analysis of Prospective Studies", Clinical Genitourinary Cancer, vol. 16, No. 2, Apr. 2018 pp. e277-e287.
"Cougar Biotechnology Presents Positive CB7630 Clinical Data at AACR Annual Meeting Late-Breaking Clinical Trials Session," News Release, available at: http://www.cougarbiotechnology.com (2007).
"Cougar Biotechnology Presents Positive CB7630 (Abiraterone Acetate) Phase I and Phase II Data at ASCO 2008 Annual Meeting," News Release, available at: http://www.cougarbiotechnology.com (2008).
"Cougar Biotechnology Presents CB7630 Phase I Data at Prostate Cancer Foundation Scientific Retreat," News Release, available at: http://www.cougarbiotechnology.com (2004).
"Cougar Biotechnology Presents CB7630 Phase I Clinical Data at the 2005 Prostate Cancer Symposium," News Release, available at: http://www.cougarbiotechnology.com (2005).
Cougar Biotechnology Initiates Phase II Trial of CB7630 (Abiraterone Acetate), News Release, available at: http://www.cougarbiotechnology.com (2006).
"Cougar Biotechnology Announces Presentation of Positive Phase I and Phase II Data at ASCO Prostate Cancer Symposium," News Release, available at: http://www.cougarbiotechnology.com (2007).

"Cougar Biotechnology Announces Presentation of Positive CB7630 Phase I Clinical Data at ASCO 2008 Genitourinary Cancers Symposium," News Release, available at: http://www.cougarbiotechnology.com (2008).
"Cougar Biotechnology Announces Presentation of Positive CB7630 Clinical Data at ESMO Conference," News Release, available at: http://www.cougarbiotechnology.com (2007).
"Cougar Biotechnology Announces Presentation of Positive CB7630 Clinical Data at AUA Annual Meeting," News Release, available at: http://www.cougarbiotechnology.com (2007).
"Cougar Biotechnology Announces Presentation of Positive CB7630 Clinical Data at ASCO Annual Meeting," News Release, available at: http://www.cougarbiotechnology.com (2007).
"Cougar Biotechnology Announces Presentation of Positive CB7630 Clinical Data at AACR-NCI-EORTC International Conference on Molecular Targets and Cancer Therapeutics," News Release, available at: http://www.cougarbiotechnology.com (2007).
"Cougar Biotechnology Announces Presentation of Positive CB7630 (Abiraterone Acetate) Phase II Data at ASCO 2009 Genitourinary Cancers Symposium," News Release, available at: http://www.cougarbiotechnology.com (2009).
"Cougar Biotechnology Announces Positive CB7630 Phase I Data Presented at the National Cancer Research Institute Conference," News Release, available at: http://www.cougarbiotechnology.com (2006).
"Cougar Biotechnology Announces Positive CB7630 Phase I Data at the AACR Innovations in Prostate Cancer Research Conference," News Release, available at: http://www.cougarbiotechnology.com (2006).
"Cougar Biotechnology Announces Initiation of Phase III Trial of CB7630 (Abiraterone Acetate)," News Release, available at: http://www.cougarbiotechnology.com (2008).
"Cougar Biotechnology Announces Initiation of Phase I/II Trial of CB7630 (Abiraterone Acetate) in Advanced Breast Cancer Patients," News Release, available at: http://www.cougarbiotechnology.com (2008).
"Cougar Biotechnology Announces Initiation of Phase I/II Trial for CB7630 (Abiraterone Acetate)," News Release, available at: http://www.cougarbiotechnology.com (2005).
"Cougar Biotechnology Announces Initiation of Phase I Trial for CB7630 (Abiraterone Acetate)," News Release, available at: http://www.cougarbiotechnology.com (2006).
"Cougar Biotechnology Announces CB7630 Phase I Data to be Presented at National Cancer Research Institute Conference," News Release (Sep. 27, 2006), available at: http://www.cougarbiotechnology.com (2006).
"Cougar Biotechnology Announces Approval of IND for Abiraterone Acetate," News Release, available at: http://www.cougarbiotechnology.com (2006).
"Cougar Biotechnology Announces Agreement with FDA on Special Protocol Assessment for Phase III Trial of CB7630 (Abiraterone Acetate)," News Release, available at: http://www.cougarbiotechnology.com (2008).
"Cougar Biotechnology Announces Agreement with FDA on Special Protocol Assessment for Phase III Trial of CB7630 (Abiraterone Acetate) in Chemotherapy Naive Castration Resistant Prostate Cancer Patients", News Release, available at: http://www.cougarbiotechnology.com (2008).
"Cougar Biotechnology Announces Acceptance of CTA for Abiraterone Acetate," News Release, available at: http://www.cougarbiotechnology.com (2005).
"CB-7630 Shows Activity in Prostate Cancer Trials," Daily Essentials (2007).
"BTG Licenses New Prostate Cancer Drug to Cougar Biotechnology," News Release, available at: http://www.cougarbiotechnology.com (2004).
"A Phase 3, Randomized, Double-Blind, Placebo-Controlled Study of Abiraterone Acetate (CB7630) Plus Prednisone in Patients with Metastatic Castration-Resistant Prostate Cancer Who Have Failed Docetaxel-Based Chemotherapy," Clinical Genitourinary Cancer, vol. 6(2):140 (2008).
Zytiga Promotional Brochure—Zytiga abiraterone acetate—an Oral Androgen Biosynthesis Inhibitor.

(56) References Cited

OTHER PUBLICATIONS

Zytiga Promotional Brochure—Zytiga (abiraterone acetate)—Introducing a New Option for Patients with mCRPC before Chemotherapy.
Zytiga Promotional Brochure—Prednisone reduces the incidence and severity of mineralocorticoid-related adverse reactions with Zytiga.
Zytiga Promotional Brochure—in Men with mCRPC—Mechanism of Action.
Zytiga Promotional Brochure—for patients with mCRPC who received prior Chemotherapy containing Docetaxel.
Zytiga Promotional Brochure—A comparison of the Mechanisms of Action of Select Prostate Cancer Treatments.
Zytiga Presentation—Key Clinical Findings for Patients with mCRPC who have progressed on Androgen Deprivation Therapy.
Zoladex(Rregisterd) 10.8 mg 3-Month (goserelin acetate implant), AstraZeneca (2004), package insert.
Zoladex(Rergisterd) 10.8 mg (goserelin acetate implant), AstraZeneca (2004), package insert.
Zoladex (Registered) 3.6 mg (goserelin acetate implant), AstraZeneca (2004), package insert.
Zoladex (Registered) 10.8 mg 3-Month (goserelin acetate implant), AstraZeneca (2004), package insert.
Zoladex (Registered) 10.8 mg (goserelin acetate implant), AstraZeneca (2004), package insert.
Yap et al., "Targeting CYP17: Established and Novel Approaches in Prostate Cancer," Current Opinion in Pharmacology (Jul. 28, 2008), vol. 8:449-457 (2008).
Yap et al., "Abiraterone acetate, an oral irreversible inhibitor of CYP450C17, administered to castration refractory prostate cancer patients is safe, suppresses androgen and steroid precursor levels, and has a high degree of durable antitumor activity," J Urology, vol. 177(4)p. 199 (2007).
Yano, A., et al., "Glucocorticoids Suppress Tumor Lymphangiogenesis of Prostate Cancer Cells", Clin Cancer Res (2006), vol. 12, pp. 6012-6017.
Yano, A., et al., "Glucocorticoids Suppress Tumor Angiogensis and In vivo Growth of Prostate Cancer Cells", Clin. Cancer Res., (2006) 12, 3003-3009.
Yano et al., "Glucocorticoids Suppress Tumor Angiogenesis and In vivo Growth of Prostate Cancer Cells", Clinical Cancer Reserch, May 15, 2006, vol. 12, No. 10, pp. 3003-3009.
Xu et al., Correlation between Prostate-Specific Antigen Kinetics and Overall Survival in Abiraterone Acetate-Treated Castration-Resistant Prostate Cancer Patients, Clinical Cancer Reserch, Jul. 15, 2015, vol. 21, No. 14 pp. 3170-3177.
Written Opinion of the International Searching Authority for PCT/US2008/008540.
Written Opinion of the International Searching Authority for PCT/US2007/018769.
Wikipedia, Corticosteriod, undated, website, 2013.
Whitworth, "Mechanism of glucocorticoid-induced hypertension," Kidney International, vol. 31:1213-1224 (1987).
Wang, C., et al., "Hypertension due to 17a-Hydroxylase deficiency", Australian and New Zealand Journal of Medicine (1978), 8(3), p. 295-299.
Walsh et al., "Docetaxel Plus Prednisone or Mitoxantrone Plus Prednisone for Advanced Prostate Cancer," J Urology, vol. 173 :2 p. 456 (2005).
Vogelzang, N.J., Curriculum Vitae, 15 pages.
Vitamin D Boosts Cancer Treatment, http://news.bbc.co.uk/l/hi/health/2961806.stm (2003).
Vitamin D Aids Chemotherapy for Advanced Prostate Cancer, http://www.supplementquality.com/efficacy/VitD. prostate chemo.html (2002).
Vink-Van Wijingaarden et al., "Inhibition of breast cancer cell growth by combined treatment with vitamin D3 analogues and tamoxifen," Cancer Research, American Association for Cancer Research, Baltimore, MD:5711-5717, abstract (1994).
Vijayakumar, S. et al., "Clinical Trials Involving Vitamin D Analogs in Prostate Cancer", Cancer J. vol. 11(5): 362-73 (2005).
Viadur(Rregisterd) (leuprolide acetate implant). Bayer Pharmaceuticals Corporation (2004), package insert.
Venkitaraman, R., et al., "Efficacy of Low-Dose Dexarnethasone in Castration-Refractory Prostate Cancer", BJU Int (2008), 101, pp. 1756-1764.
Twenty Nineth Edition Physicians' Desk Reference, 1975, PDR, 4 pages.
Trial of Abiraterone Without Exogenous Glucocorticoids in Men With CRPC With Correlative Assessment of Hormone Intermediates, 10 pages.
TRELSTAR(Trademark) LA 11.25 mg (triptorelin pamoate for injectable suspension), Pharmacia & Upjohn Company (2001), package insert.
TRELSTAR (Trademark) Depot 3.75 mg (triptorelin pamoate for injectable suspension), Pharmacia & Upjohn Company (2001), package insert.
Tomic, R., et al "Hormonal Effects of High Dose Medroxyprogesterone Acetate Treatment in Males with Renal or Prostatic Adenocarcinoma", (1988), vol. 22 (1), Abstract.
Thirty Second Edition Physicians' Desk Reference, 1978, PDR, 6 pages.
Third Party Observations dated Oct. 18, 2012 for EP Appln. No. 07837326.3.
Third Party Observations dated Mar. 28, 2013 for EP Appln. No. 07837326.3.
Third Party Observations dated Jul. 1, 2013 for EP Appln. No. 078373263.
Theodore, "Cancers Genito-Urinaires," Oncologie, vol. 10:497-500 (2008) (partial English translation enclosed).
The reply of applicant (i.e. The Proprietor of herein opposed patent) dated Jun. 4, 2013 in relation to the corresponding US2011/0144016A1 US proceedings.
TAXOTERE (docetaxel) Injection Concentrate, Aventis Pharmaceuticals Inc. (2005). prescribing information.
TAXOL (Registered) (paclitaxel) Injection. Bristol-Myers Squibb Company (2003). package insert.
Taplin, "Drug Insight: Role of the Androgen Receptor in the Development and Progression of Prostate Cancer," Nature Clin. Practice Oncol, vol. 4(4):236-244 (2007).
Tannock., et al., "Docetaxel Plus Prednisone or Mitoxantrone Plus Prednisone for Advanced Prostate Cancer", Journal of Urology (2005), 173(2), p. 456.
Tannock, IF, et al. Docetaxel plus prednisone or mitoxantrone plus prednisone for advanced prostate cancer, The New England Journal of Medicine, 2004, pp. 1502-1512, vol. 351(15).
Tanagho, E.A., et al., "The Leading Single-Volume Resource in Urology", Smith's General Urology, 16th Edition, (2004), Chapter 19, pp. 321-323; Chapter 22, pp. 380-385.
Takeda et al., "Inhibitors of the Key Enzymes of Androgen Synthesis: Potential Agents as Targets for Prostate Cancer," Japanese Journal of Clinical Medicine, vol. 58(Suppl.):312-316 (2000) (partial English translation enclosed).
Szmulewitz et al., "Antiandrogen Therapy in Prostate Cancer," Update on Cancer Therapeutics, vol. 2:119-131 (2007).
Remington, The Science and Practice of Pharmacy, 20th Edition (2000), p. 1363-1370.
Reid, A., et al., "Annals of Oncology", Educational and Abstract Book of the ESMO Conference Lugano (ECLU), (2007), 18(Supplement 9), ix173-ix174. Abstract 50PD.
Reid et al., "Selective CYP17 Inhibition With Abiraterone Acetate Results in a High Response Rate in Castration-Resistant Prostate Cancer Confirming the Continued Importance of Targeting Androgen Receptor Signaling," poster (2008).
Reid et al., "Selective CYP17 Inhibition with Abiraterone Acetate (AA) Results in a High Response Rate (RR) in Castration-Resistant Prostate Cancer (CRPC) Confirming the Continued Importance of Targeting Androgen Receptor (AR) Signaling," ASCO 2008 Genitourinary Cancers Symposium, abstract No. 50 (2008).
Reid et al., "CYP17 Inhibition as a Hormonal Strategy for Prostate Cancer," Nature Clin. Prac. Urology, vol. 5(11):610-620 (2008).

(56) References Cited

OTHER PUBLICATIONS

Randy Osborne, "'Historic' and 'practice-changing' Zytiga delivers in prostate cancer at ASCO", 2 pages.
Ramiah et al., "Clinical Endpoints for Drug Development in Prostate Cancer," Current Opinion in Urology, vol. 18:303-308 (2008).
Raghavan et al., "Prostate Cancer: Moving Forward by Reinventing the Wheel . . . But This Time it is Round," J. Clin. Oncol., vol. 26(28):4535-4536 (2008).
Prostate Cancer Principles and Practice, Taylor & Francis (2006) Chapter 93.
Prelone, Physician's Desk Reference, 54th edition: 1959-1960 (2000).
PredniSONE Tablets USP, 1 mg, 2.5 mg, 5 mg, 10 mg, 20 mg and 50 mg, PredniSONE Oral Solution USP, 5 mg per 5 mL and PredniSONE Intensol (Trademark) Oral Solution (Concentrate), 5 mg per mL, Revised Nov. 2012, 18 pages.
Prednisone Side Effects from http://www.drugs.com/sfx/prednisone-side-effects.html?printable=1, (Jul. 8, 2010).
Potter et al., "Highly potent inhibitors of human cytochrome P-450 (17alpha)," Poster presented at the third drug discovery and development symposium, San Diego, California (1993).
Potter et al., "Discovery of highly potent and selective enzyme inhibitors with potential for the treatment of prostate cancer; the important dual role of transition metal chemistry in both drug design and synthesis," Poster presented at the SmithKline Beecham Research Symposium, Robinson College, Cambridge, England (1993).
Potter et al., "A Convenient, Large-Scale Synthesis of Abiraterone Acetate [3Beta-acetoxy-17-(3-pyridyl) androsta-5,16-diene], a Potential New Drug for the Treatment of Prostate Cancer," Organic Preparations and Procedures Intl, vol. 29(1):123-134 (1997).
Posner. G.H. et al.,—A non-Calcemic Sulfone Version of the Vitamin D3 Analogue Seocalcitol (EB1089): Chemical Synthesis. Biological Evaluation and Potency Enhancement of the Anticancer Drug Adriamycin, Bioorganic & Medicinal Chem. 9: 2365-71 (2001).
Porter et al., "Novel Steroidal Inhibitors of Human Cytochrome P45017.alpha.-Hydroxylase-C17,20-lyase): Potential Agents for the Treatment of Prostatic Cancer", J. Med. Chem., 1995, vol. 38, No. 13, pp. 2463-2471.
Petrylak, D.P., "New Paradigms for Advanced Prostate Cancer", Rev. Urol. (2007), 9, Suppl. 2, S3-S12.
Petrylak, "Future Directions in the Treatment of Androgen-Independent Prostate Cancer," Urology 65 (Supplement 6A), pp. 8-13 (2005).
Peehl et al., "Preclinical activity of Ketoconazole in combination with calcitriol or the vitamin D analogue EB 1089 in prostate cancer cells," J. Urology, vol. 168, pp. 1583-1588 (2002).
PCT Written Opinion of the International Searching Authority for PCT/US2007/018770, published Feb. 28, 2008.
PCT International Search Report for PCT/US2007/018770, published Feb. 28, 2008.
Paltiel et al., "Management of severe hypokalemia in hospitalized patients: a study of quality of care based on computerized databases", Arch Intern Med. Apr. 23, 2001, vol. 161, No. 8, pp. 1089-1095.
Oudard et al., "Prostate Cancer: update," Bull. Cancer, 92(10), pp. 865-73 (2005).
Oudar, Stephane, et al. Actualite dans le cancer de la prostate, Synthese, Bull Cancer 2005; 92 (10), pp. 865-873 (relevance in English abstract).
Opar, Alisa, "ASCO Presentations Highlight Value of Cancer Biomarkers," Nature Reviews, vol. 7:547-548 (2008).
Olmos et al., "Reply: Clinical Outcome and Prognostic Factors for Patients Treated Within a Phase I Study: The Royal Marsden Hospital Experience," British Journal of Cancer, vol. 99:1365 (2008).
Novantrone (Registered) (nixtoxantrone for injection concentrate), Serono Inc. (2005), package insert.

Non-Final Office Action dated May 7, 2010 from the United States Patent and Trademark Office for U.S. Appl. No. 12/171,352, filed Jul. 11, 2008.
Non-final Office Action dated May 14, 2009 for U.S. Appl. No. 11/844,445, filed Aug. 24, 2007.
Nimalasena et al., "Paraneoplastic Cushing's Syndrome in Prostate Cancer: A Difficult Management Problem," BJU International, vol. 101 :424-427 (2007).
Newell et al, the Cancer Research UK experience of pre-clinical toxicology studies to support early clinical trials with novel cancer therapies, Elsevier, 2004, pp. 899-906, vol. 40.
NCCN Practice Gudelines in Oncology—V. 1.2005, Prostate Cancer, 41 pages.
Nakabayashi, M., et al., "Response to Low-Dose Ketoconazole and Subsequent Dose Escalation to High-Dose Ketoconazole in Patients with Androgen-Independent Prostate Cancer", Amer Cane Soc., 107(5), (2006) pp. 975-981.
Mottet et al., "Highlights on Prostate Cancer from Urological and Oncological Congresses in 2007," European Urology Supplements, vol. 7:460-476 (2008).
Mostaghel, EA. et al. Molecular Pathways: Targeting resistance in the androgen receptor for therapeutic benefit, Clin Cancer Res, Dec. 4, 2013.
Mostaghel, E.A., "Abiraterone in the treatment of metastatic castration-resistant prostate cancer", Cancer Management Res. (2014) 6, p. 39-51.
Mostaghel et al., "Intracrine Androgen Metabolism in Prostate Cancer Progression: Mechanisms of Castration Resistance and Therapeutic Implications," Best Practice & Research Clinical Endocrinology & Metabolism, vol. 22(2): 243-258 (2008).
Morgan et al., "Impact of prednisone on toxicities and survival in metastatic castration-resistant prostate cancer: A systematic review and meta-analysis of randomized clinical trials", Critical Reviews in Oncology/Hematology, Jun. 2014, vol. 90, No. 3, pp. 253-261.
Moreira et al., "CYP17 Inhibitors for Prostate Cancer Treatment—An Update," Current Medicinal Chemistry), vol. 15:868-899 (2008).
Moreira et al, Synthesis and evaluation of novel 17-indazole androstene derivatives designed as CYP17 inhibitors, Elsevier, 2007, pp. 939-948, vol. 72.
Milliken et al., "EB1089, a vitamin D receptor agonist, reduces proliferation and decreases tumor growth rate in a mouse model of hormone-induced mammary cancer," Cancer Letters, New York, NY, vol. 229 (2):205-215 (2005).
Mendel et al., "In vivo antitumor activity of SU11248, a novel tyrosine kinase inhibitor targeting vascular endothelial growth factor and platelet-derived growth factor receptors: determination of a pharmacokinetic/pharmacodynamic relationship", Clinical Cancer Research, Jan. 2003, vol. 9, No. 1, pp. 327-337.
McPhaul, Michael J., "Mechanisms of Prostate Cancer Progression to Androgen Independence," Best Practice & Research Clinical Endocrinology & Metabolism, vol. 22(2):373-388 (2008).
McKay et al., "A phase II trial of abiraterone acetate (AA) without prednisone in castration resistant prostate cancer (CRPC)", Genitourinary (Prostate) Cancer, An American Society of Clinical Oncology Journal, 5 pages.
Masuda et al., "Promise of vitamin D analogues in the treatment of hyperproliferative conditions," Mol. Cancer Ther., vol. 5(4) pp. 797-808 (2006).
Martins et al., "A Validated Liquid Chromatographic-Tandem Mass Spectroscopy Method for the Quantification of Abiraterone Acetate and Abiraterone in Human Plasma," J. Chromatography B, vol. 843:262-267 (2006).
Lupron Depot (Registered)—7.5 mg (leuprolide acetate for depot suspension). TAP Pharmaceutical Products Inc., 1-9 (2005). package insert.
Lupron Depot (Registered)—4 Month 30 mg (leuprolide acetate for depot suspension). TAP Pharmaceutical Products Inc.. 1-11 (2005), package insert.
Lupron Depot (Registered)—3 Month 22.5 mg (leuprolide acetate for depot suspension). TAP Pharmaceutical Products Inc. 1-10 (2005), package insert.
Summary of Product Characteristics for Zytiga 250mg tablets (Jan. 16, 2014).

(56) References Cited

OTHER PUBLICATIONS

Sternberg, "Systematic Chemotherapy and New Experimental Approaches in the Treatment of Metastatic Prostate Cancer," Annals of Oncol., vol. 19 (Supp. 7):vii91-vii95 (2008).
Statement of Opposition, Zentiva k.s., 2014.
Statement of Opposition, Teva Pharmaceutical Industries, Ltd., 2014.
Statement of Opposition, Synthon B.V., 2014.
Statement of Opposition, Stada Arzneimittel, 2014.
Statement of Opposition, Stada Arzneimittel AG (translated in English).
Statement of Opposition, Maiwald Patentanwalts GmbH, 2014.
Statement of Opposition, Laboratorios Leon Farma, S.A., 2014.
Statement of Opposition, Isenbruck Bosl Horschler LLP, 2014.
Statement of Opposition, Hetero Drugs, 2014.
Statement of Opposition, Helm AG, 2014.
Statement of Opposition, Helm AG (translated in English).
Statement of Opposition, Generics Ltd., 2014.
Statement of Opposition, Galenicum Health, S.L., 2014.
Statement of Opposition, Cabinet Lavoix, 2014.
Statement of Opposition, Arnold Siedsma, 2014.
Statement of Opposition, Alison Gallafent, 2014.
Statement of Opposition, Alfred E. Tiefenbacher, 2014.
Statement of Opposition, Alfred E. Tiefenbacher (translated in English).
Statement of Opposition, Actavis Group Ptc ehf, 2014.
St. Louis, a Division of J. B. Lippincott, Drug Facts and Comparisons, 1985 Edition, 13 pages.
Sonpavde et al., "Impact of single-agent daily prednisone on outcomes in men with metastatic castration-resistant prostate cancer", Prostate Cancer and Prostatic Diseases, Mar. 2017, vol. 20, No. 1, pp. 67-71.
Small, E.J., et al., "Simultaneous Antiandrogen Withdrawal and Treatment with Ketoconazole and Hydrocortisone in Patients with Advanced Prostate Carcinoma", Amer Canc Soc., 80(9), (1997) pp. 1755-1759.
Small et al, The Case for Socondary Hormaonal Therapies in the Chemotherapy Age, The Journal of Urology, 2006, pp. S66-S71, vol. 176.
Sills, Irene N., et al., "17a-hydroxylase deficiency in a genetic male and female sibling pair", Int. J. Gynaecol. Obstet., (1981), 19, p. 473-479.
Sharifi et al., "Secondary Hormonal Therapy for Prostate Cancer: What Lies on the Horizon," BJU International, vol. 101:271-74 (2007).
Seventy One Edition Physicians' Desk Reference, the trusted drug reference for over 70 years, 2017, PDR, 5 pages.
Seocalcitol Versus Placebo in Advanced Hepatocellular Carcinoma. LEO Pharma Study http://www.clinicaltrials.gov/c1/show, No. 100051532 (2004).
Schroder, "Progress in Understanding Androgen-Independent Prostate Cancer (AIPC): A Review of Potential Endocrine-Mediated Mechanisms," Eurovean Urology, vol. 53: 1129-1137 (2008).
Scholz, et al., Long-Term Outcome for Men with Androgen Independent Prostate Cancer Treated with Ketoconazole and Hydrocortisone, The Journal of Urology, 2005, pp. 1947-1952, vol. 173.
Scher et al., "Biology of Progressive, Castration-Resistant Prostate Cancer: Directed Therapies Targeting the Androgen-Receptor Signaling Axis," J. Clin. Oncol. vol. 23(32):8253-61 (2005).
Saunders et al., "Inhibition of breast and ovarian carcinoma cell growth by 1,25-dihydroxyvitamin D3 combined with retinoic acid or dexamethasone," Anti-Cancer Drugs, Rapid Communications of Oxford, vol. 6 (4):562-569 (1995).
Sartor, et al, Abiraterone Prolongs Survival in Metastatic Prostate Cancer, Nature Reviews Clinical Oncology, 2011, pp. 515-516, vol. 8.
Sartor et al., "Novel Therapeutic Strategies for Metastatic Prostate Cancer in the Post-Docetaxel Setting", Academia-Pharma Intersect: Genitourinary Cancer: Prostate, The Oncologist, Nov. 2, 2011, vol. 16, pp. 1487-1497.
Sartor et al., "Combination therapy: Abiraterone prolongs survival in metastatic prostate cancer", Nature Reviews Clinical Oncology, Aug. 2, 2011, vol. 8, No. 9, pp. 515-516.
Sahu, B., et al "FoxA1 Specifies Unique Androgen and Glucocorticoid Receptor Binding Events in Prostate Cancer Cells", Cancer Research (2013), vol. 73, pp. 1570-1580.
Sabroe, T.P. et al., "An Efficient Synthesis of a Key Intermediate for the Biologically Active Vitamin D Analogue. Seocalcitol", Organic Process Research & Deli. vol. 8(1): 133-35 (2004).
Ryan, "Secondary Hormonal Manipulations in Prostate Cancer," Hematology/Oncology Clinics of North America, vol. 20(4):925-934 (2006).
Ryan et al., "Prostate Specific Antigen Only Androgen Independent Prostate Cancer: Natural History, Challenges in Management and Clinical Trial Design," J. Urology, vol. 178:S25-S29 (2007).
Ryan et al., "Phase I Evaluation of Abiraterone Acetate (CB7630), a 17 alpha hydroxylase C17,20-Lyase Inhibitor as Secondary Hormonal Therapy in Castration Resistant Prostate Cancer (CRPC)," poster (undated).
Ryan et al., "Phase I Evaluation of Abiraterone Acetate (CB7630), a 17 alpha hydroxy lase C17,20-Lyase Inhibitor in Androgen-Independent Prostate Cancer (AIPC)," ASCO 2007 Prostate Cancer Symposium, abstract No. 278 (2007).
Ryan et al., "Impact of prior ketoconazole therapy on response proportion to abiraterone acetate, a 17-alpha hydroxy lase C17,20-lyase inhibitor in castration resistant prostate cancer (CRPC)," J. Clin. Oncol. (Meeting abstracts), vol. 26 (May 20 Supplement), abstract No. 5018 (2008).
Ryan et al., "Impact of Prior Ketoconazole Therapy on Response Proportion to Abiraterone Acetate, a 17 alpha hydroxylase C17,20-Lyase Inhibitor in Castration Resistant Prostate Cancer (CRPC)," presentation (2008).
Ryan et al., "Effect of Concomitant Food Intake on Pharmacokinetics of Abiraterone Acetate, a 17 alpha Hydroxylase C17,20-Lyase Inhibitor in Castration-Resistant Prostate Cancer (CRPC)," Molecular Cancer Therapeutics (Dec. 2007), vol. 6(12):3527s, 2007 AACR-NCI-EORTC International Conference, Poster Session C, abstract No. C2 (2007).
Ryan et al., "Abiraterone Acetate Plus Prednisone in Chemotherapy (Chemo)-Naive Castration Resistant Prostate Cancer (CPRC) Patients Not Exposed to Ketoconazole: Results of a Multi-Center Phase II Study," 2009 Genitourinary cancers Symposium (Feb. 26-28, 2009), abstract Submission (2008).
Runge, Marschall S., et al., Principles of Molecular Medicine; Second edition; (2006) Humana Press Inc. ISBN: 1-58829-202-9. pp. 365-376 and 482-484.
Rowlands et al., "Esters of 3-Pyridylacetic Acid that Combine Potent Inhibition of 17alpha- Hydroxylase/C17.20-Lyase (Cytochrome P45017alpha) with Resistance to Esterase Hydrolysis," J. Med. Chem., vol. 38:4191-4197 (1995).
Ross et al., "Hormone Refractory Prostate Cancer: Choosing the Appropriate Treatment Option," Oncology, vol. 21(2):185-193 (2007).
Report to the Nation on Prostate Cancer 2004. Prostate Cancer Foundation.
Chang, Ching-Yi, et al. Glucocorticoids Manifest Androgenic Activity in a Cell Derived from a Metastatic Prostate Cancer, Cancer Research, 2001, pp. 8712-8717, vol. 61.
Cecil Textbook of Medicine, Wyngaarden & Smith 18th edition; Chapter on "Glucocorticosteroid Therapy", Wyngaarden & Smith 18th edition, (1988) p. 128-131.
CB1089 http://www.cougarbiotechnology.com/eb1089.html (Jul. 2006).
Carducci, M.A,, "What is more exciting? The Activity of Docetaxel in Early Prostate Cancer or the Successful Collaboration between Urologists and Medical Oncologists to complete a study in early Prostate Cancer'?", Journal of Clinical Oncology (2005), vol. 23, No. 15, pp. 3304-3307.
Carden et al., "Crossover Pharmacokinetics (PK) Study to Assess Oral Administration of Abiraterone Acetate Capsule and Tablet Formulations in Fasted and Fed States in Patients with Prostate Cancer," J. Clin. Oncol. (Meeting abstracts), vol. 26 (May 20 Supplement), abstract No. 5168 (2008).

(56) References Cited

OTHER PUBLICATIONS

Cannell, 100th Annual Meeting of the American Association for Cancer Research, Los Angeles, CA, USA;, http://oncology.thelancet.com, 2007, pp. 471, vol. 8.
Campbell-Walsh Urology, Ninth Edition, Saunders, vol. 3, Chapters 104 and 105, 2007.
Burke et al., "Active-Site Conformation of 17-(3-Pyridyl) Androsta-5, 16-Dien-3Beta-ol, a Potent Inhibitor of the P450 Enzyme C17alpha-Hydroxylase/C17-20 Lyase," Bioorganic & Medicinal Chemistry letters, vol. 5(11):1125-1130 (1995).
Bubley, G.J., et al., Eligibility and response guidelines for phase II clinical trials in adrogen-independent prostate cancer: recommendations from the Prostate-Specific Antigen Working Group, J. Clin Oncol, 17(11) (1999) pp. 3461-3467.
Bruno et al, Targeting cytochrome P450 enzymes: A new approach in anti-cancer drug development, Elsevier, 2007, pp. 5047-5060, vol. 15.
Bonnie Gillis, "ASCO GU Highlights New Treatment Options for Prostate Cancer", 2016 Highlights from ASH: CLL News, 2015, 5 Pages.
Blutt et al., "A calcitriol analogue, EB 1089, inhibits the growth of LNCaP tumors in nude mice," Cancer Res., vol. 60(4), pp. 779-782 (2000).
Biophosphonates Fact Sheet. The Paget Foundation http://www.paget.org/Information.FactSheet/bisfact/html (Jul. 2006).
Beer et al., "Weekly high-dose calcitriol and docetaxel in metastatic androgen-independent prostate cancer," .J Clin. Oncology, vol. 21(1) pp. 123-128 (2003).
Beardsley et al., "Systemic Therapy After First-Line Docetaxel in Metastatic Castration-Resistant Prostate Cancer," Current Opinion in Supportive and Palliative Care, vol. 2:161-166 (2008).
Barrie et al., "Inhibitors of Cytochrome P450 17alpha (17alpha-Hydroxylase/C17,20 Lyase)," Endocrine-Related Cancer, vol. 3:25-39 (1996).
Barrie et al., "Highly Potent Inhibitors of Human Cytochrome P-450(17alpha): Activity in Vitro and in Vivo," British J. Cancer (1993), p. 75, BACR/ACP/BOA Annual Meeting, abstract No. 175 (1993).
Barrie et al., "Highly potent inhibitors of human cytochrome P-450 (17alpha): Activity in vitro and in vivo," Poster presented at the British Association for Cancer Research meeting in Sheffield, England (1993).
Barrie et al., "CB7598: A Potent Inhibitor of Steroidal 17alpha-Hydroxylase/c17,20 Lyase. A Potential New Drug for the Treatment of Prostate Cancer," J. Pharmacy and Pharmacology, vol. 47(12B):1076 (1995).
Barrie et al., "Biochemistry of Potent Cytochrome P45017alpha Inhibitors," British J. Cancer, vol. 75 (Suppl. 1):6, abstract No. 1.7 (1997).
Barrie et al., "Biochemistry and Pharmacokinetics of Potent Non-Steroidal Cytochrome P45017Alpha Inhibitors," J. Steroid Biochem. Malec. Biol., vol. 60(5-6):347-351 (1997).
Barrie et al., "17-(3-Pyridyl) Substituted Irreversible Inhibitors of Cytochrome P45017alpha" British J. Cancer, vol. 78(Suppl. 1):34, abstract No. 33 (1998).
Azad et al., "Outcomes with Abiraterone Acetate in Metastatic Castration-resistant Prostate Cancer Patients Who Have Poor Performance Status", European Urology, vol. 67, Issue 3, Mar. 2015, pp. 441-447.
Ayub, M., Inhibition of testicular 17a-hydroxylase and 17,20-lyase but not 3B-hydroxysteroid dehydrogenase-isomerase or 17B-hydroxysteroid oxidoreductase by ketoconazole and other imidazole drugs, Journal of Steroid Biochemistry (1987) 28(5), p. 521-531.
Auchuz-3, R.J,, "The genetics, pathophysiology, and the management of human deficiencies of P450c17", Endocrinol Metab Clin North Am (2001), 30, p. 101-119.
Auchus et al., "Use of Prednisone With Abiraterone Acetate in Metastatic Castration-Resistant Prostate Cancer", The Oncologist published online Oct. 31, 2014, 12 pages.
Auchus et al., "Human steroid biosynthesis for the oncologist", NIH Public Access, J Investing Med. Author manuscript; available in PMC May 14, 2013, 22 pages.
Attard et al., "Activity, toxicity, and effect on steroid precursor levels of abiraterone (A), an oral irreversible inhibitor of CYP17 (17Alfa-hydroxylase/17.20, lyase), in castrate men with castration refractory prostate cancer (CRPC)," 2007 Prostate Cancer Symposium, Abstract No. 264.
Attard et al., "Steroid Hormone Receptors in Prostate Cancer: A Hard Habit to Break?", Cancer Cell, vol. 16, Dec. 8, 2009, pges 458-462.
Attard et al., "Selective Inhibition of CYP17 with Abiraterone Acetate is Well Tolerated and Results in a High Response Rate in Castration-Resistant Prostate Cancer (CRPC)," Molecular Cancer Therapeutics (Dec. 2007), vol. 6(12): 3455s, 2007 AACR-NCI-EORTC International Conference, Poster Session B, abstract No. B73 (2007).
Attard et al., "Prostate Cancer's Day in the Sun," BMJ, vol. 337: a1256 (2008).
Attard et al., "Predictors of Response and Pharmacodynamic (PD) Endpoints in a Phase I and Pharmacokinetic Study of Abiraterone Acetate (AA) in Castration-Resistant Prostate Cancer (CRPC)," ASCO 2008 Genitourinary Cancers Symposium, abstract No. 214 (2008).
Attard et al., "Management Strategies for Hormone-Refractory Prostate Cancer", Therapy in Practice, Am. J. 2006, vol. 5, No. 3, pp. 193-169.
Allard et al., "Improving the Outcome of Patients with Castration-Resistant Prostate Cancer Through Rational Drug Development," British Journal of Cancer, vol. 95:767-774 (2006).
Allard et al., "Dissecting Prostate Carcinogenesis Through ETS Gene Rearrangement Studies: Implications for Anticancer Drug Development," J. Clin. Pathol., vol. 61:891-896 (2008).
Allard et al., "Antitumor Activity with CYP17 Blockade Indicates That Castration-Resistant Prostate Cancer Frequently Remains Hormone Driven", Cancer Res 2009, vol. 69, No. 12, Jun. 15, 2009, pp. 4937-4940.
Attard et al., "Abiraterone, an oral, irreversible CYP450C17 enzyme inhibitor appears to have activity in post-docetaxel castration refractory prostate cancer (CRPC) patients (pts)," Annals of Oncology, vol. 18(Supplement 9): ix173-ix174. Abstract No. 51PD (2007).
Allard et al., "Abiraterone Acetate Is Well", Journal of Clinical Oncology, vol. 28, No. 29, Oct. 10, 2010, pp. e560-e561.
Assessment Report for Zytiga (abiraterone) published 2011 by the CHMP of the EMA.
ASCO Cancer Foundation, Poster Session F: Hormone Refractory, ASCO, 2005.
Armstrong et al., "New Drug Development in Metastatic Prostate Cancer," Urologic Oncology: Seminars and Original Investigations, vol. 26: 430-437 (2008).
American Cancer Society: Cancer Drug Guide: mitoxantrone from http://www.cancer.org.docroot/CDG/content/CDG_mitoxantrone.asp (Jun. 24, 2010).
Aggarwal et al., "Development of Abiraterone Acetate, a 17-alpha Hydroxylase C17,20-Lyase Inhibitor as a Secondary Hormonal Therapy in Prostate Cancer," Update on Cancer Therapeutics, vol. 2:171-175 (2007).
About ZYTIGA (Registered) Arbiraterone acetate, retrived from https://www.zytiga.com/choosing-zytiga#how-zytiga-works, on Jul. 25, 2017, 7 pages.
"Positive Phase II Data on Cougar Biotechnology's CB7630 Presented at Prostate Cancer Foundation Scientific Retreat," News Release, available at http://www.cougarbiotechnology.com (2008).
"Cougar Biotechnology to Present Clinical Data on CB7630 (Abiraterone Acetate) at American Society of Clinical Oncology 2008 Annual Meeting," News Release, available at: http://www.cougarbiotechnology.com (2008).
"Cougar Biotechnology Presents Positive CB7630 Phase II Data at Prostate Cancer Foundation Scientific Retreat," News Release, available at: http://www.cougarbiotechnology.com (2007).
"Cougar Biotechnology Presents Positive CB7630 Phase II Data at EORTC-NCI-AACR Symposium," News Release, available at: http://www.cougarbiotechnology.com (2008).

(56) References Cited

OTHER PUBLICATIONS

"Cougar Biotechnology Presents Positive CB7630 Phase II Data at Chemotherapy Foundation Symposium," News Release, available at: http://www.cougarbiotechnology.com (2007).

"Cougar Biotechnology Presents Positive CB7630 Phase I and Phase II Data at ASCO 2008 Genitourinary Cancers Symposium," News Release, available at: http://www.cougarbiotechnology.com (2008).

Geoff Cumming, "Inference by eye: reading the overlap of independent confidence intervals", Statistics in Medicine, vol. 28, 2009, pp. 205-220.

Garnick et al., "Androgen deprivation therapy: the future", Prostate Cancer Principles and Practice, 19 pages.

Friel, Patrick N., et al., "Suppression of adrenal function by low-dose prednisone: assessment with 24-hour urinary steroid hormone profiles-A review of five cases", Alternative Medicine Review (2006), 11(1).

Fourteenth Edition Physicians' Desk Reference to Pharmaceutical Specialties and Biologicals, 1960, PDR, 2 pages.

Fossa, et al., Weekly Docetaxel and Prednisone Versus Prednisolone Alone in Androgen-Independent Prostate Cancer: A Randomized Phase II Study, European Urology, 2007, pp. 1691-1699, vol. 52.

Flaig et al., "A phase II trial of dexamethasone, vitamin D, and carboplatin in patients with hormone—refractory prostate cancer," Cancer, vol. 107(2), pp. 266-274 (2006).

Fizazi et al., "Low Incidence of Corticosteroid-associated Adverse Events on Long-term Exposure to Low-dose Prednisone Given with Abiraterone Acetate to Patients with Metastatic Castration-resistant Prostate Cancer", Eur Urol. Sep. 2016, vol. 70, No. 3, pp. 438-444.

Fizazi et al., "Abiraterone plus Prednisone in Metastatic, Castration-Sensitive Prostate Cancer", The new england journal of medicine, Jul. 2017, vol. 377, No. 4, pp. 352-360.

Final Office Action dated Apr. 6, 2010 from the United States Patent and Trademark Office for U.S. Appl. No. 11/844,445, filed Aug. 24, 2007.

Ergun-Longmire, Berrin, et al., "Two Novel Mutations Found in a Patient with 17a-Hydroxylase Enzyme Deficiency", The Journal of Clinical Endocrinology & Metabolism (2006), 91(10), p. 4179-4182.

Endocrinology, Inhibition of Androgen Synthesis in Human Testicular and Prostatic Microsomes and in Male Rats by Novel Steroidal Compounds, Endocrinology, 1999, pp. 2891-2897, vol. 140 No. 6.

Eighteenth Edition Physicians' Desk Reference to Pharmaceutical Specialties and Biologicals, 1964, PDR Published by Medical Economics, Inc. 3 pages.

Efstathiou, Eleni, et al. Effects of Abiraterone Acetate on Androgen Signaling in Castrate-Resistant Prostate Cancer in Bone, American Society of Clinical Oncology, Journal of Clinical Oncology, 2011, pp. 1-8.

Efstathiou et al., "Identification of an Androgen Withdrawal Responsive Phenotype in Castrate Resistant Prostate Cancer (CRPC) Patients Treated with Abiraterone Acetate," presentation (undated).

Efstathiou et al., "Candidate Predictors of Response to Abiraterone Acetate (AA) in Castrate Resistant Prostate Cancer (CRPC)," 2009 Genitourinary Cancers Symposium (Feb. 26-28, 2009), abstract Submission (2008).

Dorff, TB, Crawford, ED. Management and challenges of corticosteroid therapy in men with metastatic castrate-resistant prostate cancer, Annals of Oncology, 2013, pp. 31-38, vol. 24(1).

Discover Zytiga—Patient Brochure.

DELTASONE—prednisone tablet Pharmacia and Upjohn and Company, Deltas one (Registered) prednisone tablets, USP. 13 pages.

Declaration by Helen Grimes in the matter of Opposition by Northern Rivers Pty Ltd., 43 pages, 2004.

Declaration by Dr. Jacqueline Anne Warner in the matter of Opposition by Northern Rivers Pty Ltd., 25 pages, 2004.

DeBono et al., •"Clinical and endocrine evaluation of abiraterone acetate (AA), a rationally designed small molecule inhibitor of androgen synthesis targeting 17Alfa hydroxy lase (17OH)/17,20 lyase in patients with hormone refractory prostate cancer," 2005 Prostate Cancer Symposium, Abstract No. 290.

De Coster et al., "P450-Dependent Enzymes as Targets for Prostate Cancer Therapy," J. Steroid Biochem. Malec-Biol., vol. 56(1-6):133-143 (1996).

De Bono et al., "Antitumor Activity of Abiraterone Acetate, a CYP17 Inhibitor That Blocks Androgen Synthesis, in Castration-Resistant Prostate Cancer," ASCO 2008 Annual Meeting, Presentation.

De Bono et al., "Anti-tumor activity of abiraterone acetate (AA), a CYP17 inhibitor of androgen synthesis, in chemotherapy naive and docetaxel pre-treated castration resistant prostate cancer (CRPC)," J. Clin. Oncol. (Meeting abstracts), vol. 26 (May 20 Supplement), abstract No. 5005 (2008).

De Bono et al, Inhibition of CYP450c17 by abiraterone administered once daily to castrate patients with prostate cancer resistant to LHRH analogues, anti-androgens and steriod therapy is well tolerated . . . , The institute of Cancer Research, 2007.

Danila et al., "Preliminary Phase II Results of Abiraterone Acetate in Patients with Castration-Resistant Metastatic Prostate Cancer After Failure of Docetaxel-Based Chemotherapy," ASCO 2008 Genitourinary Cancers Symposium, abstract No. 3 (2008).

Danila et al., "Preliminary Phase II Results of Abiraterone Acetate in Patients With Castration Resistant Metastatic Prostate Cancer After Failure of Docetaxel-Based Chemotherapy: COU-AA-004," in Innovative Cancer Therapy for Tomorrow: Foundation Symposium XXV; presentation (2007).

Danila et al., "Abiraterone acetate and prednisone in patients (Pts) with progressive metastatic castration resistant prostate cancer (CRPC) after failure of docetaxel-based chemotherapy," J. Clin. Oncol. (Meeting abstracts), vol. 26 (May 20 Supplement), abstract No. 5019 (2008).

Danielenko et al., "Enhancement by other compounds of the anti-cancer activity of vitamin D3 and its analogs," Experimental Cell Research, vol. 298 (2):339-358 (2004).

Dalhoff, K. A., "Phase II Study of the Vitamin D Analogue Seocalcitol in Patients with Inoperable Hepatocellular Carcinoma", 89(2) British Journal of Cancer, 252-257 (2003).

Czock, et al., "Pharmacokinetics and Pharmacodynamics of Systemically Administered Glucocorticoids", Pharmacokinet (2005), 44(1), p. 61-98.

Cougar Biotechnology, Cougar Technology Announces Presentation of Positive CB7630 Clinical Data at ASCO Annual Meeting, The Free Library, Jun. 4, 2007.

Cougar Biotechnology, Cougar Biotechnology presents positive CB7630 Clinical Data at AACR Annual Meeting Late-Breaking Clinical Trials Session, Cougar Biotechnology, Apr. 17, 2007.

Cougar Biotechnology, Cougar Biotechnology presents CB7630 Phase I clinical data at the 2005 Prostate Cancer Symposium, AllBusiness, 2005.

Cougar Biotechnology, Cougar Biotechnology announces presentation of positive phase I and phase II data at ASCO Prostate Cancer Symposium, Cougar Biotechnology, Feb. 23, 2007.

Cougar Biotechnology, Cougar Biotechnology Announces Presentation of Positive CB7630 Clinical Data at ESMO Conference, Drugs.com, Jul. 2007.

Cougar Biotechnology, Cougar Biotechnology Announces Initiation of Phase I/II Trial for CB7630 (Arbiraterone Acetate), Cougar Biotechnology, Dec. 14, 2004.

Coudar Biotechnology Inc. with the U.S. Securities and Exchange Commission, Form 10-QSB, 2013.

Cooper et al., "Mechanisms of Disease: Biomarkers and Molecular Targets from Microarray Gene Expression Studies in Prostate Cancer," Nature Clin. Practice Oncol., vol. 4(12):677-687 (2007).

Consider the impact of ZVTIGA (Registered) 500 mg film-coated tablets over the course of a month or a year for your patients with mCRPC, ZVTIGA (Registered) (abiraterone acetate) Dosing & Monitoring HCP. 7 pages.

Colston, K. W., "Effects of Seocalcitol (EB1089) on Nitrosomethyl Urea-Induced Rat Mammary Tumors", 80(3) Breast Cancer, 303-311 (2003).

(56) References Cited

OTHER PUBLICATIONS

Colston et al., "Mechanisms implicated in the growth regulatory effects of vitamin D in breast cancer," Endocrine-Related Cancer, vol. 9(1):45-59 (2001).
Collins et al., "A systematic review of the effectiveness of docetaxel and mitoxantrone for the treatment of metastatic hormone-refractory prostate cancer," British J. of Cancer, 95, pp. 457-462 (2006).
Cole, "Cancer Expert Doubts Claims About Prostate Cancer Trial," BMJ, vol. 337: a979 (2008).
Clement et al., "Three dimensional pharmacophore modeling of human CYP17 inhibitors. Potential agents for prostate cancer therapy", journal of Medicinal Chemistry, vol. 46, No. 12, 2003, pp. 2345-2351.
Christensen. G.L., "Sequential Versus Combined Treatment of Human Breast Cancer Cells with Antiestrogens and the Vitamin D Analogue EB 1089 and Evaluation of Predictive Markers for Vitamin D Treatment", Breast Cancer Researc and Treatment. 85(1) 53-63 (2004).
Chou et al., "Desoxyepothilone B: An efficacious microtubule-targeted antitumor agent with a promising in vivo profile relative to epothilone B", Proc. Natl. Acad. Sci. USA vol. 95, No. 16, Aug. 1998 Pharmacology, pp. 9642-9647.
Chi et al., "A Phase I Pharmacokinetic and Pharmacodynamic Study of OGX-011, a 2'-Methoxyethyl Antisense Oligonucleotide to Clusterin, in Patients With Localized Prostate Cancer", Journal of the National Cancer Institute, vol. 97, Issue 17, Sep. 7, 2005, pp. 1287-1296.
Chen, C.D, et al., "Molecular determinants of resistance to antiandrogen therapy", Nat Med, 10(1), (2004) pp. 33-39.
Chemicals: Seocalcitol http://ctd.mdibl.org/voc.go:isessionid=126741EAF326D9CE517F360251236091?voc=chem&acc=C078903&queryferms=seocalcitol&qurey Type=contains&browser=r (Jul. 17, 2006).
"Decision on Appeal", In the United States Court of Appeals for the Federal Circuit, Appeal Nos. 2019-1147, 2019-1148, 2019-1323, 2019-1324, decided May 14, 2019, 27 pages.
Kwak et al., "Abiraterone acetate and prednisolone for metastatic castration-resistant prostate cancer failing androgen deprivation and docetaxel-based chemotherapy: A phase II bridging study in Korean and Taiwanese patients", International Journal of Urology, Dec. 2014, 21, 1239-1244.
DeBono et al., "Abiraterone and Increased Survival in Metastatic Prostate Cancer", The New England Journal of Medicine, May 26, 2011, vol. 364, No. 21, 1995-2005.
Trepanier, "Glucocorticoids", Cliniciansbrief.com, Dec. 2015, 5 pages.
Postma, "Treatment of prostate cancer", Annals of Oncology, Sep. 2006, vol. 17, Supplement 10, x207-x210.
Taichman et al., "The evolving biology and treatment of prostate cancer", The Journal of Clinical Investigation, Sep. 2007, vol. 117, No. 9, 2351-2361.
Tewari et al., "Long-term Survival Probability in Men with Clinically Localized Prostate Cancer Treated Either Conservatively or with Definitive Treatment (Radiotherapy or Radical Prostatectomy)", Urology, Dec. 2006, vol. 68, Issue 6, 1268-1274.
"Final Written Decision", United States Patent and Trademark Office Before the Patent Trial and Appeal Board, Case No. IPR2016-00286 U.S. Pat. No. 8,822,438 B2, dated Jan. 17, 2018, 48 pages.
"Final Written Decision", United States Patent and Trademark Office Before the Patent Trial and Appeal Board, Case No. IPR2016-01582 U.S. Pat. No. 8,822,438 B2, dated Jan. 17, 2018, 51 pages.
"Final Written Decision", United States Patent and Trademark Office Before the Patent Trial and Appeal Board, Case No. IPR2016-01332 U.S. Pat. No. 8,822,438 B2, dated Jan. 17, 2018, 50 pages.
United States District Court District of New Jersey, BTG International Limited, Janssen Biotech, Inc., (Plaintiffs) vs. Actavis Laboratories FL, Inc., (Defendants), "Defendants Sun Pharmaceuticals Industries, Ltd. and Sun Pharmaceuticals Industries, Inc.'s Answer and Counterclaim to Plaintiffs' First Amended Complaint for Patent Infringement", Field for Case # 2:15-cv-05909-KM-JBC, Document No. 93, on Oct. 15, 2015, p. 1 of 33.
United States District Court District of New Jersey, BTG International Limited, at el., (Plaintiffs) vs. Actavis Laboratories FL, Inc., et al., (Defendants) for Case # 15-cv-05909-KM-JBC, "Declaration of Brendan F. Barker in Support of Defendants' Opening Claim Construction Brief" Document 210-2 Filed Jun. 30, 2016 p. 1 of 3.
United States Patent and Trademark Office Before the Patent Trial and Appeal Board, Declaration of Marc B. Garnick, M.D., Mylan Pharmaceuticals Incorporated (Petitioner)vs. Janssen Oncology, Inc. (Patent Owner) for U.S. Pat. No. 8,822,438, "Methods and Compositions for Treating Cancer" filed for Case IPR2016-01332, Janssen Exhibit 2015, on Feb. 16, 2017, 93 pages.
Understanding Zytiga Users "Urologist Success" Qualitative Research, Janssen Exhibit 2092, Amerigen vs. Janssen filed for Case # IPR2016-00286, Jan. 2014.
Understanding the role of prednisone in combination with ZYTIGA(Registered), (abiraterone acetate), Putting Prednisone in Perspective, 13 pages.
UBS Research, "Medivation—A Look at the Growth and Share in Prostate Cancer," Feb. 3, 2014.
UBS Investment Research, "Johnson & Johnson—Zytiga Label Extended," Dec. 10, 2012.
U.S. Securities and Exchange Commission, Cougar Biotechnology, Inc., http://www.sec.gov/Archives/data/1335102/000119312507180813/0001193125-07-180813-index.html(Apr. 7, 2014).
U.S. Patent, Alan H. Auerbach, et al., U.S. Pat. No. 8,822,438 B2, "Methods and Compositions for Treating Cancer", filed for Case# 15-cv-05909-KM-JBC, Document# 288-1, filed on Feb. 13, 2011, p. 2 of 13.
U.S. Food and Drug Administration, FDA Website Drugs@FDA—Zytiga, http://www.accessdata.fda.gov/scripts/cder/drugsatfda/index.cfm? fuseaction=Search DrugDetails (accessed Jun. 28, 2016), Mylan Pharms. Inc., Exhibit 1046, 2 pages.
U.S. Food and Drug Administration, "Orange Book: Approved Drug Products with Therapeutic Equivalence Evaluations" Wockhardt v. Janssen IPR2016-00286 Janssen Exhibit 2107 Oct. 3, 2016.
U.S. Food and Drug Administration, "FDA News Release", Press Announcements > FDA approves Zytiga for late-stage prostate cancer, Janssen Exhibit 2070, Amerigen v. Janssen, for Case # IPR2016-00286, Apr. 28, 2011, 2 Pages.
U.S. Food and Drug Administration FDA News Release, "FDA expands Zytiga's use for late-stage prostate cancer", Dec. 10, 2012 http://www.fda.gov/NewsEvents/Newsroom/PressAnnouncements/ucm331492.htm (access Jun. 30, 2016), 2 pages.
U.S. Food and Drug Administration ("FDA"), FDA Approves New Indication for Taxotere-Prostate Cancer, FDA News Release dated May 19, 2004, 2 pages.
U.S. District Court, District of New Jersey, BTG International Limited, Janssen Biotech, Inc., Janssen Oncology, Inc., Janssen Research & Development, LLC. (Plaintiffs) vs. Actavis Laboratories FL Inc., et al. (Defendants), "Defendants Amneal Pharmaceuticals LLC and Amneal Pharmaceuticals of New York, LLC's Answer and Counterclaim to Plaintiffs' Second Amended Complaint for Patent Infringement", filed for case# 15-cv-05909-KM-JBC, Document # 300, filed on Feb. 27, 2017, p. 1 of 35.
U.S. District Court, District of New Jersey, BTG International Limited, Janssen Biotech, Inc., Janssen Oncology, Inc., Janssen Research & Development, LLC. (Plaintiffs) vs. Actavis Laboratories FL Inc., et al. (Defendants), "Defendants Actavis Laboratories FL, Inc's Answer and Counterclaim to Plaintiffs' Second Amended Complaint for Patent Infringement", filed for case# 15-cv-05909-KM-JBC, Document # 299, filed on Feb. 27, 2017, p. 1 of 35.
U.S. District Court, District of New Jersey, BTG International Limited, Janssen Biotech, Inc., Janssen Oncology, Inc., Janssen Research & Development, LLC. (Plaintiffs) vs. Actavis Laboratories FL Inc., et al. (Defendants), "Plaintiffs' Answer to Wockhardt's Counterclaims Raised in Response to Second Amended Complaint", filed for case# 15-cv-05909-KM-JBC, Document # 305, filed on Mar. 6, 2017, p. 1 of 23.
U.S. District Court, District of New Jersey, BTG International Limited, Janssen Biotech, Inc., Janssen Oncology, Inc., Janssen Research & Development, LLC. (Plaintiffs) vs. Actavis Laboratories

(56) References Cited

OTHER PUBLICATIONS

FL Inc., et al. (Defendants), "Plaintiffs' Answer to Teva's Counterclaims Raised in Response to Second Amended Complaint", filed for case# 15-cv-05909-KM-JBC, Document # 311, filed on Mar. 20, 2017, p. 1 of 12.
U.S. District Court, District of New Jersey, *BTG International Limited, Janssen Biotech, Inc., Janssen Oncology, Inc., Janssen Research & Development, LLC.* (Plaintiffs) vs. *Actavis Laboratories FL Inc., et al.* (Defendants), "Plaintiffs' Answer to Sun's Counterclaims Raised in Response to Second Amended Complaint", filed for case# 15-cv-05909-KM-JBC, Document # 310, filed on Mar. 20, 2017, p. 1 of 12.
U.S. District Court, District of New Jersey, *BTG International Limited, Janssen Biotech, Inc., Janssen Oncology, Inc., Janssen Research & Development, LLC.* (Plaintiffs) vs. *Actavis Laboratories FL Inc., et al.* (Defendants), "Plaintiffs' Answer to Mylan's Counterclaims Raised in Response to Second Amended Complaint", filed for case# 15-cv-05909-KM-JBC, Document # 306, filed on Mar. 7, 2017, p. 2 of 11.
U.S. District Court, District of New Jersey, *BTG International Limited, Janssen Biotech, Inc., Janssen Oncology, Inc., Janssen Research & Development, LLC.* (Plaintiffs) vs. *Actavis Laboratories FL Inc., et al.* (Defendants), "Plaintiffs' Answer to Hikma/West Ward's Counterclaims Raised in Response to Second Amended Complaint", filed for case# 15-cv-05909-KM-JBC, Document # 314, filed on Mar. 20, 2017, p. 1 of 13.
U.S. District Court, District of New Jersey, *BTG International Limited, Janssen Biotech, Inc., Janssen Oncology, Inc., Janssen Research & Development, LLC.* (Plaintiffs) vs. *Actavis Laboratories FL Inc., et al.* (Defendants), "Plaintiffs' Answer to DRL's Counterclaims Raised in Response to Second Amended Complaint", filed for case# 15-cv-05909-KM-JBC, Document # 313, filed on Mar. 20, 2017, p. 1 of 13.
U.S. District Court, District of New Jersey, *BTG International Limited, Janssen Biotech, Inc., Janssen Oncology, Inc., Janssen Research & Development, LLC.* (Plaintiffs) vs. *Actavis Laboratories FL Inc., et al.* (Defendants), "Plaintiffs' Answer to Amneal's Counterclaims Raised in Response to Second Amended Complaint", filed for case# 15-cv-05909-KM-JBC, Document # 312, filed on Mar. 20, 2017, p. 1 of 13.
U.S. District Court, District of New Jersey, *BTG International Limited, Janssen Biotech, Inc., Janssen Oncology, Inc., Janssen Research & Development, LLC.* (Plaintiffs) vs. *Actavis Laboratories FL Inc., et al.* (Defendants), "Plaintiffs' Answer to Actavis's Counterclaims Raised in Response to Second Amended Complaint", filed for case# 15-cv-05909-KM-JBC, Document # 315, filed on Mar. 20, 2017, p. 1 of 14.
U.S. District Court, District of New Jersey, *BTG International Limited, Janssen Biotech, Inc., Janssen Oncology, Inc., Janssen Research & Development, LLC.* (Plaintiffs) vs. *Actavis Laboratories FL Inc., et al.* (Defendants), "Defendants West-Ward Pharmaceuticals Corp. and Hikma Pharmaceuticals, LLC's Answer and Counterclaim to Plaintiffs' Second Amended Complaint for Patent Infringement", filed for case# 15-cv-05909-KM-JBC, Document # 303, filed on Feb. 27, 2017, p. 1 of 37.
U.S. District Court, District of New Jersey, *BTG International Limited, Janssen Biotech, Inc., Janssen Oncology, Inc., Janssen Research & Development, LLC.* (Plaintiffs) vs. *Actavis Laboratories FL Inc., et al.* (Defendants), "Defendants Sun Pharmaceuticals Industries, Ltd. and Sun Pharmaceuticals Industries, Inc.'s Answer and Counterclaim to Plaintiffs' Second Amended Complaint for Patent Infringement", filed for case# 15-cv-05909-KM-JBC, Document # 302, filed on Feb. 27, 2017, p. 1 of 34.
U.S. District Court, District of New Jersey, *BTG International Limited, Janssen Biotech, Inc., Janssen Oncology, Inc., Janssen Research & Development, LLC.* (Plaintiffs) vs. *Actavis Laboratories FL Inc., et al.* (Defendants), "Defendants Dr. Reddy's Laboratories, Inc. and Dr. Reddy's Laboratories, Ltd.'s Answer and Counterclaim to Plaintiffs' Second Amended Complaint for Patent Infringement", filed for case# 15-cv-05909-KM-JBC, Document # 301, filed on Feb. 27, 2017, p. 1 of 34.
U.S. District Court, District of New Jersey, *BTG International Limited, Janssen Biotech, Inc., Janssen Oncology, Inc., Janssen Research & Development, LLC.* (Plaintiffs) vs. *Actavis Laboratories FL Inc., et al.* (Defendants), "Apotex Corp. and Apotex Inc.'s Answer and Affirmative Defenses to Plaintiffs' Second Amended Complaint for Patent Infringement", filed for case# 15-cv-05909-KM-JBC, Document # 297, filed on Feb. 27, 2017, p. 1 of 122.
U.S. District Court, District of New Jersey, *BTG International Limited, Janssen Biotech, Inc., Janssen Oncology, Inc., Janssen Research & Development, LLC.* (Plaintiffs) vs. *Actavis Laboratories FL Inc., et al.* (Defendants), "Answer of Defendant Teva Pharmaceuticals USA, Inc. to Plaintiffs' Second Amended Complaint for Patent Infringement and Counterclaim for Declaratory Judgment", filed for case# 15-cv-05909-KM-JBC, Document # 298, filed on Feb. 27, 2017, p. 1 of 33.
U.S. District Court, District of New Jersey, *BTG International Limited, Janssen Biotech, Inc., Janssen Oncology, Inc., Janssen Research & Development, LLC.* (Plaintiffs) vs. *Actavis Laboratories FL Inc., et al.* (Defendants), "Answer. Affirmative Defenses and Counterclaims of Wockhardt Bio AG, Wockhardt USA LLC, and Wockhardt LTD. to Plaintiffs' Second Amended Complaint for Patent Infringement", filed for case# 15-cv-05909-KM-JBC, Document # 288, filed on Feb. 13, 2017, 2 pages.
U.S. District Court, District of New Jersey, *BTG International Limited, et al.*(Plaintiffs) vs. *Actavis Laboratories FL Inc., et al.* (Defendants), "Answer to Second Amended Complaint, Separate Defenses, and Counterclaims by Defendants Mylan Pharmaceuticals Inc. and Mylan Inc.", filed for case# 15-cv-05909-KM-JBC, Document # 289, filed on Feb. 14, 2017, p. 1 of 115.
Tucker et al., "Reversible Adrenal Insufficiency induced by Ketoconazole" Janssen Exhibit 2090, *Wockhardt* vs. *Janssen*, Case # IPR2016-01582, JAMA, vol. 253, No. 16 Apr. 26, 1985, 2 Pages.
Truven Commercial and Medicare Data, *Wockhardt* vs. *Janssen*, Filed for case IPR2016-01332, Janssen Exhibit 2135, 12 pages.
Toshihiko Yanase et al., "Deletion of a phenylalanine in the N-terminal region of human cytochrome P-450(17 alpha) results in partial combined 17 alpha-hydroxylase/17, 20-lyase deficiency", Journal of Biological Chemistry May 24, 1989, vol. 264 No. 30 pp. 18076-18082.
Top 50 pharmaceutical products by global sales, from Internaet URL: http://www.pmlive.com/top_pharma_list/Top_50_pharmaceutical_products_by_global_sales, *Wockhardt* v. *Janssen*, Filed for Case, IPR2016-01582, Janssen Exhibit 2012, on Feb. 1, 2017, 2 pages.
Therasse et al., "New Guidelines to Evaluate the Response to Treatment in Solid Tumors Journal of the National Cancer Institute", vol. 92, No. 3, Feb. 2, 2000 pp. 205-216.
The Institute of Cancer Research, "Abiraterone: a story of scientific innovation and commercial partnership",Making the discoveries that defeat cancer filed for IPR2.016-00286 Oct. 3, 2016.
Taxotere(Registered),"RX Taxotere (Docetaxel) injecton Concentrate", Informatin as of May 2004, 35 pages.
Taxotere prescribing information (Dec. 2015), Taxotere (docetaxel) Injection Concentrate, Intravenous Infusion (IV). Initial U.S. Approval: 1996, 63 pages.
Taxotere label, May 2004, Mylan Pharms. Inc. Exhibit 1140.
Tannock I. et al., "Docetaxel plus prednisone or mitoxantrone plus prednisone for advanced prostate cancer", N. Eng. J. Med. 351, Oct. 7, 2004, pp. 1502-12.
T. Saika et al., Treatment of androgen-independent prostate cancer with dexamethasone: A prospective study in stage D2 patients, International Journal of UrologyM 8, pp. 290-294 (2001).
Sweeney et al., "Chemohonnonal Therapy in Metastatic Hormone-Sensitive Prostate Cancer", New England Journal of Medicine, filed for Case *Wockhardt* vs. *Janssen* IPR2016-01582, Janssen Exhibit 2163, on Aug. 20, 2015, vol. 373, No. 8, pp. 737-746.
Swartz and Dluhy, "Corticosteroids: Clinical Pharmacology and Therapeutic Use", Clinical Pharmacology and Therapeutic, Drugs, file for Case IPR2016-00286, Janssen Exhibit 2068, on 1978, vol. 16, pp. 238-255.

(56) References Cited

OTHER PUBLICATIONS

Strother et al., "Novel cytotoxic and biological agents for prostate cancer" Where will the money be in 2005?, European Journal of Cancer 2005, filed for Case IPR2016-00286, Janssen Exhibit 2008, vol. 41, pp. 954-964.
Sternberg, "Hormone refractory metastatic prostate cancer", Annals of Oncology, file for Case IPR2016-00286, Janssen Exhibit 2056, on 1992, vol. 3, pp. 331-335.
Starney et al., "Prostate-Specific Antigen as a Serum Marker for Adenocarcinoma of the Prostate," The New England journal of Medicine, vol. 317, No. 15, Oct. 8, 1987 pp. 909-916.
Sonino et at., "The Use of Ketoconazole as an Inhibitor of Steroid Production", New England Journal of Medicine, file for Case IPR2016-01332, Janssen Exhibit 2163, on September 24, 1987, vol. 317, No. 13, pp. 812-818.
Small et at., "Antiandrogen Withdrawal Alone or in Combination With Ketoconazole in Androgen-Independent Prostate Cancer Patients: A Phase III Trial (CAL.GB 9583)", Journal of Clinical Oncology, file for Case IPR2016-00286, Janssen Exhibit 2063, on Mar. 15, 2004, vol. 22, No. 6, pp. 1025-1033.
Sephton, et at., "Diurnal Cortisol Rhythm as a Predictor of Breast Cancer Survival", Journal of the National Cancer Institute, vol. 92, No. 12, Jun. 21, 2000, pp. 994-1000.
United States Patent and Trademark Office, Before the Patent Trial and Appeal Board, *Mylan Pharmaceuticals Inc*(Petitioners) vs. *Janssen Oncology, Inc.* (Patent Owner)for U.S. Pat. No. 8,822,438 B2, "Patent Owner's Response", filed for Case IPR2016-01332, Mar. 8, 2017. 70 Pages.
United States Patent and Trademark Office, Before the Patent Trial and Appeal Board, *Mylan Pharmaceuticals Inc* (Petitioner) vs. *Janssen Oncology, Inc* (Patent Owner) for U.S. Pat. No. 8,822,438 B2, "Janssen Oncology, Inc's Preliminary Response", filed for Case IPR2016-01332, Oct. 12, 2016, 11 Pages.
United States Patent and Trademark Office, Before the Patent Trial and Appeal Board, *Mylan Pharmaceuticals Inc* (Petitioner) vs. *Janssen Oncology, Inc.* (Patent Owner) for U.S. Pat. No. 8,822,438 B2, "Before Lora M. Green, Rama G. Elluru, and Kristina M. Kalan, Administrative Patent Judges" filed for Case IPR2016-01332, Jan. 10, 2011, 13 Pages.
United States Patent and Trademark Office, Before the Patent Trial and Appeal Board, In the Inter Partes Review (IPR) for U.S. Pat. No. 8,822,438, "Declaration of Dr. Scott R. Serels", filed for Case IPR2016-01582 Janssen Exhibit 2017, on Dec. 4, 2015, 46 pages.
United States Patent and Trademark Office, Before the Patent Trial and Appeal Board, *Argentum Pharmaceuticals LLC.* (Petitioner) vs. *Janssen Oncology, Inc.* (Patent Owner) for U.S. Pat. No. 8,822,438 B2, "Before Lora M. Green, Rama O. Elluru, and Kristina M. Kalan, Administrative Patent Judges", filed for Case IPR2016-01317, Sep. 19, 2016, 11 Pages.
United States Patent and Trademark Office, Before the Patent Trial and Appeal Board, *Ametigen Pharmaceuticals Limited, Argentum Pharmaceuticals LLC* (Petitioner) vs. *Janssen Oncology, Inc* (Patent Owner) for U.S. Pat. No. 8,822,438 B2. "Patent Owner's Motion for Observations on Cross-Examination", filed tor Case IPR2016-00286, Jan. 30, 2017, 17 Pages.
United States Patent and Trademark Office, Before the Patent Trial and Appeal Board, Amerigen Pharmaceuticals Limited, *Argentum Pharmaceuticals, LLC,* (Petitioner) vs. *Janssen Oncology, Inc.* (Patent Owner) for U.S. Pat. No. 8,822,438 B2, "Supplemental Declaration of Mark J. Ratain, M.D. in Response to Patent Owner's", filed for Case IPR2016-00286, Amerigen Exhibit 1193 on Jan. 25, 2017, 5 pages.
United States Patent and Trademark Office, Before the Patent Trial and Appeal Board, *Amerigen Pharmaceuticals Limited, Argentum Pharmaceuticals, LLC,* (Petitioner) vs. *Janssen Oncology, Inc* (Patent Owner) for U.S. Pat. No. 8,822,438 B2, "Declaration of William D. Hare in Response to Patent Owner's", filed for Case IPR2016-00286, Amerigen Exhibit 1194 on Jan. 26, 2017, 3 pages.
United States Patent and Trademark Office, Before the Patent Trial and Appeal Board, *Amerigen Pharmaceuticals Limited, Argentum Pharmaceuticals, LLC,* (Petitioner) vs. *Janssen Oncology, Inc.* (Patent Owner) for U.S. Pat. No. 8,822,438 B2, "Declaration of Gabriela Malerassi in Response to Patent Owner's", filed for Case IPR2016-00286, Amerigen Exhibit 1195 on Jan. 26, 2017, 3 pages.
United States Patent and Trademark Office, Before the Patent Trial and Appeal Board, *Amerigen Pharmaceuticals Limited, and Argentum Pharmaceuticals LLC.* (Petitioner) vs. *Janssen Oncology, Inc.* (Patent Owner) for U.S. Pat. No. 8,822,438 B2, "Supplemental Declaration of Renita Rathinam in Response to Patent Owner's", filed for Case IPR2016-00286, Amerigen Exhibit 1192 on Jan. 23, 2017, 3 pages.
United States Patent and Trademark Office, Before the Patent Trial and Appeal Board. *Amerigen Pharmaceuticals Limited*(Petitioner) vs. *Janssen Oncology, Inc.*(Patent Owner), U.S. Pat. No. 8,822,438 B2, "Declaration of Scott Sereis, M. D. in Support of Amerigen Pharmaceuticals Limited's Petition for Inter Partes Review of U.S. Pat. No. 8,822,438", filed for Case# IPR2016-00286, 6 pages.
United States Patent and Trademark Office, Before the Patent Trial and Appeal Board, *Amerigen Pharmaceuticals Limited*(Petitioner) vs. *Janssen Oncology, Inc.*(Patent Owner), U.S. Pat. No. 8,822,438 B2, "Declaration of Jayesh Bindra in Support of Amerigen Pharmaceuticals Limited's Petition for Inter Partes Review of U S. Pat. No. 8,822,438", filed for Case# IPR2016-00286, 3 pages.
United States Patent and Trademark Office, Before the Patent Trial and Appeal Board, *Amerigen Pharmaceuticals Limited Argentum Pharmaceuticals LLC* (Petitioner) vs. *Janssen Oncology, Inc.* (Patent Owner) for U.S. Pat. No. 8,822,438 B2, "Patent Owner's Response", filed for Case IPR2016-00286, Oct. 4, 2016, 18 Pages.
United States Patent and Trademark Office, Before the Patent Trial and Appeal Board, *Amerigen Pharmaceuticals Limited and Argentum Pharmaceuticals LLC.,* (Petitioners) vs. *Janssen Oncology. Inc.,* (Patent Owner) for U.S. Pat. No. 8,822,438 B2, "Declaration of Richard Auchus, M. D., Ph.D. in Support of Janssen Oncology, Inc.'s Patent Owner Response" filed for Case IPR2016-00286, Janssen Exhibit 2040.
United States Patent and Trademark Office, Before the Patent Trial and Appeal Board, *Amerigen Pharmaceuticals Limited and Argentum Pharmaceuticals LLC.,* (Petitioner) vs. *Janssen Oncology. Inc.,* (Patent Owner) for U.S. Pat. No. 8,822,438 B2, "Declaration of Matthew B. Retting, M D. in Support of Janssen Oncology, Inc.'s Patent Owner Response" Filed for Case IPR2016-00286, Janssen Exhibit 2038 on (2009) 1581-1594.
United States Patent and Trademark Office, Before the Patent Trial and Appeal Board, *Amerigen Pharmaceuticals Limited and Argentum Pharmaceuticals LLC.,* (Petitioner) vs. *Janssen Oncology, Inc.,* (Patent Owner) for U.S. Pat. No. 8,822,438 B2, "Declaration of Gerald Walter Chodak, MD in Support of Janssen Oncology, Inc.'s Patent Owner Response" filed for Case IPR2016-00286, Janssen Exhibit 2042.
United States Patent and Trademark Office, Before the Patent Trial and Appeal Board, *Amerigen Pharmaceuticals Limited and Argentum Pharmaceuticals LLC,* (Petitioners) vs. *Janssen Oncology, Inc* (Patent Owner) for U.S. Pat. No. 8,822,438 B2, "Declaration of Christopher A. Vellturo. Ph.D. In Support of Patent Owner Response" filed for Case IPR2016-00286, Janssen Exhibit 2044.
United States Patent and Trademark Office, Before the Patent Trial and Appeal Board, Amerigen Pharmaceuticals Limited and Argentum Pharmaceuticals LLC (Petitioners), Janssen Oncology, Inc. (Patent Owner) for U.S. Pat. No. 8,822,438 B2, file for Case IPR2016-01332, Janssen Exhibit 2151, on Oct. 4, 2016, 73 pages.
United States Patent and Trademark Office, Before the Patent Trial and Appeal Board, *Amerigen Pharmaceuticals Limited and Argentum Pharmaceuticals LLC* (Petitioners) vs. *Janssen Oncology, Inc* (Patent Owner), U.S. Pat. No. 8,822,438, "Methods and Compositions for Treating Cancer", "Declaration of Dr. Richard I. Dorin", filed for Case# 2016-00286, 54 pages.
United States Patent and Trademark Office, Before the Patent Trial and Appeal Board, *Amerigen Pharmaceuticals Limited and Argentum Pharmaceuticals LLC* (Petitioners) vs. *Janssen Oncology, Inc* (Patent Owner), U.S. Pat. No. 8,822,438, "Methods and Compositions for Treating Cancer", Declaration of Dr. Mark J. Ratain, 42 pages.
United States Patent and Trademark Office, Before the Patent Trial and Appeal Board, *Amerigen Pharmaceuticals Limited and Argentum*

(56) References Cited

OTHER PUBLICATIONS

*Pharmaceuticals LLC* (Petitioner) vs. *Janssen Oncology, Inc.* (Patent Owner) for U.S. Pat. No. 8,822,438, "Methods and Compositions for Treating Cancer", "Petitioners' Reply to Patent Owner's Response to Petition", filed for Case IPR2016-00286. 28 Pages.
United States Patent and Trademark Office, Before the Patent Trial and Appeal Board, *Amerigen Pharmaceuticals Limited and Argentum Pharmaceuticals LLC* (Petitioner) vs. *Janssen Oncology, Inc.* (Patent Owner) for U.S. Pat. No. 8,822.438 B2, "Petitioners' Response to Patent Owner's Motion for Observations on Cross-Examination", filed for Case IPR2016-00288, 12 Pages.
United States Patent and Trademark Office, Before the Patent Trial and Appeal Board, *Amerigen Pharmaceuticals Limited and Argentum Pharmaceuticals LLC* (Petitioner) vs. *Janssen Oncology, Inc.* (Patent Owner) for U.S. Pat. No. 8,822,438 B2, "Petitioners' Reply to Patent Owner's Identification of New Arguments and Evidence in Petitioners Reply", filed for Case IPR2016-00286, 06 Pages.
United States Patent and Trademark Office, Before the Patent Trial and Appeal Board, *Amerigen Pharmaceuticals Limited and Argentum Pharmaceuticals LLC* (Petitioner) vs. *Janssen Oncology, Inc* (Patent Owner) for U.S. Pat. No. 8,822,438 B2, "Patent Owner's Response", filed for Case IPR2016-00286, 73 Pages.
United States Patent and Trademark Office, Before the Patent Trial and Appeal Board, *Amerigen Pharmaceuticals Limited* (Petitioners) vs. *Janssen Oncology, Inc.* (Patent Owner)for U.S. Pat. No. 8,822,438 B2. "Patent Owner's Request for Reconsideration Pursuant to 37 C.F.R. (Section) 42.71(c)", filed for Case IPR2016-00286, Jun. 14, 2016, 19 Pages.
United States Patent and Trademark Office, Before the Patent Trial and Appeal Board, *Amerigen Pharmaceuticals Limited* (Petitioners) vs. *Janssen Oncology, Inc.* (Patent Owner)for U.S. Pat. No. 8,822,438 B2, "Janssen Oncology, Inc.'s Patent Owner Preliminary Response Under 37 C.F.R. (Section) 42.107", filed for Case IPR2016-00286, Mar. 10, 2016. 66 Pages.
United States Patent and Trademark Office, Before the Patent Trial and Appeal Board, *Amerigen Pharmaceuticals Limited* (Petitioners) vs. *Janssen Oncology, Inc.* (Patent Owner)for U.S. Pat. No. 8,822,438 B2, "Before Lora M. Green, Rama G. Elluru, and Kristina M. Kalan, Administrative Patent Judges", filed for Case IPR2016-00286, May 31, 2016. 20 Pages.
United States Patent and Trademark Office, Before the Patent Trial and Appeal Board, *Amerigan Pharmaceuticals Limited and Argentum Pharmaceuticals LLC* (Petitioner) vs. *Janssen Oncology, Inc.* (Patent Owner) for U.S. Pat. No. 8,882,438 B2, "Declaration of Matthew B Retting, M.D. in Support of Janssen Oncology, Inc.'s Patent Owner Response", for Case # IPR2016-00286.
United States Patent and Trademark Office, Before the Patent Trial and Appeal Board, *Actavis Laboratories FL, Inc, et at.* (Petitioners) vs. *Janssen Oncology, Inc.* (Patent Owner)for U.S. Pat. No. 8,822,438 B2, "Before Lora M. Green, Rama G Elluru, and Kristina M Kalan, Administrative Patent Judges.", filed for Case IPR2017-00853, Apr. 12, 2017, 14 Pages.
United States Patent and Trademark Office, Before the Patent Trial and Appeal Board *Mylan Pharmaceuticals Inc.*, (Petitioners) vs. *Janssen Oncology Inc.*, Case # IPR2016-01332, U.S. Pat. No. 8,822,438, Filed on Mar. 8, 2017 Mylan Pharms Inc. 70 pages.
United States Patent and Trademark Office, Before the Patent Trial and Appeal Board *Mylan Pharmaceuticals Inc. Actavis Laboratories FL Inc.* (Petitioners) vs. *Janssen Oncology Inc.* "Reply Declaration of Ivan T. Hofmann", Case # IPR2016-013321, U.S. Pat. No. 8,822,438, Mylan Pharms. Inc., 36 pages.
United States District Court, For The District of New Jersey,BTG International Limited, *Janssen Biotech, Inc , Janssen Oncology, Inc., Janssen Research and Development, LLC*, (Plaintiffs) vs. *Actavis Laboratories FL., Inc.*, Case # 15-cv-05909-KM-JBC, "Answer, Affirmative 2017 Defenses and Counterclaims of Wockhardt Bio AG, Wockhadt USA LLC, and Wockhardt Ltd. To Plaintiffs' First Amended Complaint for Patent Inferingement", Document # 76 filed Oct. 13, 2015, p. 2 of 62.

United States District Court, The District of New Jersey, *BTG International Limited* (Plaintiff) vs. *Actavis Laboratories FL, Inc.* (Defendants), "Order (Markman Patent Claim Construction)", Document# 240, Filed for Case 15-cv-05909-KM-JBC, IPR2016-01332, Janssen Exhibit 2005, on Nov. 14, 2015, p. 1 of 2.
United States District Court, The District of New Jersey, *BTG International Limited* (Plaintiff) vs. *Actavis Laboratories FL, Inc.* (Defendants), "Opinion (Markman Patent Claim Construction)", Document# 239, Filed for Case 15-cv-05909-KM-JBC, IPR2016-01332, Janssen Exhibit 2004, on Nov. 10, 2010, p. 1 of 30.
United States District Court, The District of New Jersey ,*BTG International Limited, et al.* (Plaintiffs) vs. *Amneal Pharmaceuticals LLC., et al.* (Defendants), "Responsive Expert Report of Richard Auchus. M.D., Ph.D.", filed for case# 15-cv-06909-KM-JBC, Document # 345-5. filed on Aug. 11, 2017, p. 2 of 121.
United States District Court, for The District of New Jersey, *BTG International Limited, et al.*, (Plaintiffs) vs. *Actavis Laboratories FL, Inc., et al.*, (Defendants) filed for Case # 5-cv-05909-KM-JBC, "Order (Markman Patent Claim Construction)", Documnent # 240 on Nov. 14, 2016 pp. 1 of 2.
United States District Court, for The District of New Jersey, *BTG International Limited, et al.*, (Plaintiffs) vs. *Actavis Laboratories FL, Inc., el al* , (Defendants) filed for Case # 15-cv-05909-(KM)-(JBC), "Opinion (Madman Patent Claim Construollon)", Document # 239 Filed Nov. 10, 2016 p. 1 of 30.
United States District Court, District of New Jersey, *BTG International Limited, Janssen Biotech, Inc., Janssen Oncology, Inc., Janssen Research & Development, LLC*, (Plaintiffs) vs. *Actavis Laboratories FL, Inc.*, Case # Case 2:15-cv-05909-KM-JBC. "Defendants Amneal Pharmaceuticals LLC and Amneal Pharmaceuticals of New York LLC's Answer and Counterclaim to Plaintiffs' First Amended Complaint for Patent Infringement", Document # 87 filed Oct. 15, 2015 p. 1 of 34.
United States District Court, District of New Jersey, *BTG International Limited, Janssen Biotech, Inc., Janssen Oncology, Inc., Janssen Research & Development, LLC*, (Plaintiffs) vs *Actavis Laboratories FL, Inc.*, Case # 15-cv-05909-KM-JBC, Document # 85 Filed Oct. 15, 2015 p. 1 of 35.
United States District Court, District of New Jersey, *BTG International Limited, Janssen Biotech, Inc., Janssen Oncology, Inc., Janssen Research & Development, LLC*, (Plaintiffs) vs. *Actavis Laboratories FL, Inc.*, Case # 15-cv-05909-KM-JBC. "Defendants Dr. Reddy's Laboratories, Inc. and Dr. Reddy's Laboratories, Ltd 's Answer and Counterclaim to Plaintiffs' First Amended Complaint for Patent Infringement" Document # 89, Filed Oct. 15, 2015 p. 1 of 33.
United States District Court, District of New Jersey, *BTG International Limited, Janssen Biotech, Inc., Janssen Oncology, Inc., Janssen Research & Development. LLC*, (Plaintiffs) vs. *Actavis Laboratories FL, Inc.*, Case # 15-cv-05909-KM-JBC, "Answer of Defendant Teva Pharmaceuticals USA, Inc. and Counterclaim for Declaratory Judgment", Document # Document 83, Filed Oct. 15, 2015 p. 1 of 31.
United States District Court, District of New Jersey, *BTG International Limited, Janssen Biotech, Inc., Janssen Oncology, Inc., and Janssen Research & Development, LLC*, (Plaintiffs/Conterclaim—Defendants) vs. *Mylan Pharmaceuticals Inc and Mylan Inc.*, (Defendants/Counterclaim—Plaintiffs), Case # 15-cv-05909-KM-JBC, "Answer to Amended Complaint, Separate Defenses, and Counterclaims by Defendants Mylan Pharmaceuticals Inc. and Mylan Inc.", Document # 194 Filed Apr. 22, 2016 p. 1 of 115.
United States District Court, District of New Jersey, *BTG International Limited, et al.* (Plaintiffs) vs. *Actavis Laboratories FL. Inc., et al.* (Defendants) for Case # 15-cv-05909-KM-JBC, "Declaration of John P. Fruehauf, M.D., Ph.D. on Claim Construction" Document # 210-1 Filed Jun. 30, 2016 p. 1 of 41.
United States District Court, District of New Jersey, *BTG International Limited, et al.* (Plaintiffs) vs *Actavis Laboratories FL, Inc., et al.* (Defendants) filed for Case # 15-cv-05909-KM-JBC, "Declaration of Brendan F. Barker in Support of Defendants' Responsive Claim Construction Brief" Document # 221-1 Filed Aug. 31, 2016 p. 1 of 2.

(56) References Cited

OTHER PUBLICATIONS

United States District Court, District of New Jersey, *BTG International Limited, et al.* (Plaintiffs) v. *Actavis Laboratories FL, Inc., et al* , (Defendants), for Case # 15-cv-05909-KM-JBC, "Defendants' Opening Claim Construction Brief" Document # Document 210 Filed Jun. 30, 2016 p. 1 of 24.

United States District Court for the District of New Jersey, *BTG International Limited, et al., vs. Actavis Laboratories FL, Inc, et al.*, "Second Amended Complaint for Patent Infringement" filed for case# 15-cv-05909-KM-JBC, Document No. 274 on Jan. 30, 2017, p. 1 of 114.

United States District Court Forthe District of New Jersey, *BTG International Limited, et al.*, (Plaintiffs) vs. *Actavis Laboratories FL, Inc, et al.*, (Defendants) "Second Amended Complaint for Patent Infringement" filed for case# 15-cv-05909-KM-JBC, Document No. 283 on Feb. 10, 2017, p. 1 of 4.

United States District Court for The District of New Jersey, *BTG International Limited et al.*, (Plaintiffs) vs. *Actavis Laboratories FL Inc., et. al.* (Defendants), "Opinion (Markman Patent Claim Construction)", filed for case# 15-cv-05909-KM-JBC, Document No. 240 on Nov. 14, 2016, p. 1 of 2.

United States District Court District of New Jersey, *BTG International Limited, Janssen Biotech, Inc., et al.*, (Plaintiffs) vs. *Actavis Laboratories FL, Inc., et al.*, (Defendants), "Responsive Pleading and of Defendants Hetero USA, Inc.,". Field for Case # 2:15-cv-05909-KM-JBC, Document No. 156, on Dec. 30, 2015, p. 1 of 33.

United States District Court District of New Jersey, *BTG International Limited, Janssen Biotech, Inc.*, (Plaintiffs) vs *Actavis Laboratories FL, Inc., et al.*, (Defendants), "Defendants West-Ward Pharmaceuticals Corp, and Hikma Pharmaceuticals, LLC's Answer and Counterclaim to Plaintiffs' First Amended Complaint for Patent Infringement", Field for Case # 2:15-cv-05909-KM-JBC, Document No. 91, on Oct. 15, 2015, p. 1 of 6.

Clinical Drug Application Manual, Tong Rujing et al., Shanghai Science and Technology Press, 1st edition, p. 318, 2006; 5 pages.

\* cited by examiner

METHODS AND COMPOSITIONS FOR TREATING CANCER

CROSS REFERENCE TO RELATED APPLICATIONS

This application is a continuation of U.S. application Ser. No. 15/419,148, filed on Jan. 30, 2017, which is a continuation of U.S. application Ser. No. 15/019,353, filed on Feb. 9, 2016, which is a continuation of U.S. application Ser. No. 14/750,297, filed on Jun. 25, 2015, which is a continuation of U.S. application Ser. No. 14/485,083, filed on Sep. 12, 2014, which is a continuation of U.S. application Ser. No. 14/444,513, filed on Jul. 28, 2014, which is a continuation of U.S. application Ser. No. 13/034,340, filed on Feb. 24, 2011, now U.S. Pat. No. 8,822,438, which is a continuation of U.S. application Ser. No. 11/844,440, filed on Aug. 24, 2007, which claims the benefit of U.S. Provisional Application Ser. No. 60/921,506, filed on Aug. 25, 2006, the entire disclosures of which are incorporated herein by reference.

FIELD OF THE INVENTION

Methods and compositions for treating cancer are described herein. More particularly, the methods for treating cancer comprise administering a 17α-hydroxylase/$C_{17,20}$-lyase inhibitor, such as abiraterone acetate (i.e., 3β-acetoxy-17-(3-pyridyl) androsta-5, 16-diene), in combination with at least one additional therapeutic agent, such as an anti-cancer agent or a steroid. Furthermore, disclosed are compositions comprising a 17α-hydroxylase/$C_{17,20}$-lyase inhibitor, and at least one additional therapeutic agent such as an anti-cancer agent or a steroid, e.g., a corticosteroid or, more specifically, a glucocorticoid.

BACKGROUND

The number of people diagnosed with cancer has significantly increased. Of special interest are individuals diagnosed with androgen-dependent disorders, such as prostate cancer, and estrogen-dependent disorders, such as breast cancer since such diagnoses are increasing in number at an alarming rate.

Prostate cancer is currently the most common non-skin cancer and the second leading cause of cancer-related death in men after lung cancer. The primary course of treatment for patients diagnosed with organ-confined prostate cancer is usually prostatectomy or radiotherapy. Not only are these treatments highly invasive and have undesirable side effects, such localized treatments are not effective on prostate cancer after it has metastasized. Moreover, a large percent of individuals who receive localized treatments will suffer from recurring cancer.

Additionally, breast cancer incidence in women has increased from one out of every 20 women in 1960 to one out of every eight women in 2005. Moreover, it is the most common cancer among white and African-American women. Similar to treating prostate cancer, most options for women diagnosed with breast cancer are highly invasive and have significant side-effects. Such treatments include surgery, radiation and chemotherapy.

Hormone therapy is another treatment option for individuals diagnosed with prostate or breast cancer. Hormone therapy is a form of systemic treatment for prostate or breast cancer wherein hormone ablation agents are used to suppress the production or block the effects of hormones, such as estrogen and progesterone in the body, which are believed to promote the growth of breast cancer, as well as testosterone and dihydrotestosterone, which are believed to promote the growth of prostate cancer. Moreover, hormone therapy is less invasive than surgery and does not have many of the side effects associated with chemotherapy or radiation. Hormone therapy can also be used by itself or in addition to localized therapy and has shown to be effective in individuals whose cancer has metastasized.

Even though hormone therapy is less invasive and can be used on more advanced stages of cancer, some individuals administered current hormone therapy treatments may not show a significant response or may not show any response at all to such treatments. Additionally, some patients treated with current hormone therapy treatments may also suffer from relapsing or recurring cancer. Currently, such refractory cancer patients are left with very few treatment options.

Despite the progress made in the treatment of cancer, there remains a need for more effective ways to treat cancer such as, but not limited to, prostate cancer and breast cancer. Additionally, there is a need for effective anti-cancer treatment options for patients who are not responding to current anti-cancer treatments. Also, there is a need for effective anti-cancer treatment options for patients whose cancer has recurred.

SUMMARY OF THE INVENTION

Described herein are methods for treating a cancer in which a therapeutically effective amount of a 17α-hydroxylase/$C_{17,20}$-lyase inhibitor, such as abiraterone acetate (i.e. 3β-acetoxy-17-(3-pyridyl)androsta-5,16-diene), is administered to a patient, e.g., a patient in need thereof, in combination with a therapeutically effective amount of at least one additional therapeutic agent including, but not limited to, an anti-cancer agent or steroid. Such methods can also provide an effective treatment for individuals with a refractory cancer, including individuals who are currently undergoing a cancer treatment. Therefore, in certain embodiments, the method is directed to treating a refractory cancer in a patient, in which a therapeutically effective amount of 17α-hydroxylase/$C_{17,20}$-lyase inhibitor is administered to a patient currently receiving an anti-cancer agent.

For example, in certain embodiments, the method for the treatment of a cancer in a mammal comprises administering an amount of about 0.01 mg/kg/day to about 100 mg/kg/day of abiraterone acetate and an amount of about 0.1 mg/m² to about 20 mg/m² of mitoxantrone.

In another embodiment, the method for the treatment of a cancer in a mammal comprises administering an amount of about 0.01 mg/kg/day to about 100 mg/kg/day of abiraterone acetate and an amount of about 1 mg/m² to about 175 mg/m² of paclitaxel.

In still other embodiments, the method for the treatment of a cancer in a mammal comprises administering an amount of about 0.01 mg/kg/day to about 100 mg/kg/day of abiraterone acetate and an amount of about 1 mg/m² to about 100 mg/m² of docetaxel.

Furthermore, described herein is a method for the treatment of a cancer in a mammal comprising administering an amount of about 0.01 mg/kg/day to about 100 mg/kg/day of abiraterone acetate; and an amount of about 0.01 mg to about 200 mg of leuprolide, wherein the leuprolide is administered over a period of about 3 days to about 12 months.

In other embodiments, the method for the treatment of a cancer in a mammal comprises administering an amount of about 0.01 mg/kg/day to about 100 mg/kg/day of abiraterone acetate and an amount of about 0.01 mg to about 20 mg of goserelin, wherein the goserelin is administered over a period of about 28 days to about 3 months.

Additionally, in another embodiment, the method for the treatment of a cancer in a mammal comprises administering an amount of about 0.01 mg/kg/day to about 100 mg/kg/day of abiraterone acetate and an amount of about 0.01 mg to about 20 mg of triptorelin, wherein the triptorelin is administered over a period of about 1 month.

The method for the treatment of a cancer in a mammal can also comprise administering an amount of about 0.01 mg/kg/day to about 100 mg/kg/day of abiraterone acetate and an amount of about 0.1 µg/day to about 500 µg/day of seocalcitol, such as about 100 µg/day of seocalcitol.

Also, the method for the treatment of a cancer in a mammal can comprise administering an amount of about 0.01 mg/kg/day to about 100 mg/kg/day of abiraterone acetate and an amount of about 1 mg/day to about 300 mg/day of bicalutamide.

In yet another embodiment, the method for the treatment of a cancer in a mammal can comprise administering an amount of about 0.01 mg/kg/day to about 100 mg/kg/day of abiraterone acetate and an amount of about 1 mg/day to about 2000 mg/day of flutamide.

Moreover, the method for the treatment of a cancer in a mammal can comprise administering an amount of about 50 mg/day to about 2000 mg/day of abiraterone acetate and an amount of about 0.01 mg/day to about 500 mg/day of a glucocorticoid including, but not limited to, hydrocortisone, prednisone or dexamethasone.

Also described herein are compositions for the treatment of cancer that comprise a combination of a therapeutically effective amount of at least one 17α-hydroxylase/$C_{17,20}$-lyase inhibitor and a therapeutically effective amount of at least one additional anti-cancer agent, such as, but not limited to, mitoxantrone, paclitaxel, docetaxel, leuprolide, goserelin, triptorelin, seocalcitol, bicalutamide, flutamide, or a steroid including, but not limited to, hydrocortisone, prednisone, or dexamethasone.

Finally, single unit dosage forms comprising abiraterone acetate and a glucocorticoid, optionally with carriers, diluents or excipients, are contemplated. Also, kits comprising at least one 17α-hydroxylase/$C_{17,20}$-lyase inhibitor and an additional anti cancer agent or steroid are contemplated. For example, the kit may include a vial containing abiraterone acetate and another vial containing a glucocorticoid.

Definitions

As used herein and unless otherwise defined the word "cancer," refers to the growth, division or proliferation of abnormal cells in the body. Cancers that can be treated with the methods and the compositions described herein include, but are not limited to, prostate cancer, breast cancer, adrenal cancer, leukemia, lymphoma, myeloma, Waldenström's macroglobulinemia, monoclonal gammopathy, benign monoclonal gammopathy, heavy chain disease, bone and connective tissue sarcoma, brain tumors, thyroid cancer, pancreatic cancer, pituitary cancer, eye cancer, vaginal cancer, vulvar cancer, cervical cancer, uterine cancer, ovarian cancer, esophageal cancer, stomach cancer, colon cancer, rectal cancer, liver cancer, gallbladder cancer, cholangiocarcinoma, lung cancer, testicular cancer, penal cancer, oral cancer, skin cancer, kidney cancers, Wilms' tumor and bladder cancer.

As used herein, and unless otherwise defined, the terms "treat," "treating" and "treatment" include the eradication, removal, modification, management or control of a tumor or primary, regional, or metastatic cancer cells or tissue and the minimization or delay of the spread of cancer.

As used herein, and unless otherwise defined, the term "patient" means an animal, including but not limited to an animal such as a human, monkey, cow, horse, sheep, pig, chicken, turkey, quail, cat, dog, mouse, rat, rabbit, or guinea pig. In one embodiment, the patient is a mammal and in another embodiment the patient is a human. In certain embodiments, the patient can be an adult male or female. In some embodiments, the patient is a male of age about 30 years to about 85 years. In other embodiments, the patient is a female of age about 30 years to about 85 years. In a particular embodiment, the patient has or is susceptible to having (e.g., through genetic or environmental factors) cancer. In a further embodiment, the patient has or is susceptible to having (e.g., through genetic or environmental factors) a tumor. In other embodiments, the patient can be castrated or non-castrated.

The term "17α-hydroxylase/$C_{17,20}$-lyase inhibitor" as used herein refers to an inhibitor of 17α-hydroxylase/$C_{17,20}$-lyase, (which is an enzyme in testosterone synthesis), an analog thereof, derivative thereof, metabolite thereof or pharmaceutically acceptable salt thereof. Also, unless otherwise noted, reference to a particular 17α-hydroxylase/$C_{17,20}$-lyase inhibitor can include analogs, derivatives, metabolites or pharmaceutically acceptable salts of such particular 17α-hydroxylase/$C_{17,20}$-lyase inhibitor.

The term "anti-cancer agent" as used herein refers to any therapeutic agent that directly or indirectly kills cancer cells or directly or indirectly prohibits stops or reduces the proliferation of cancer cells. It should be noted that even though throughout this specification and in the claims the phrase "anti-cancer agent" is written as a singular noun, for example; "an anti-cancer agent" or "the anti-cancer agent," the phrase "anti-cancer agent" should not be interpreted as being limited to the inclusion of a single anti-cancer agent.

As used herein, and unless otherwise defined, the phrase "therapeutically effective amount" when used in connection with a 17α-hydroxylase/$C_{17,20}$-lyase inhibitor or therapeutic agent means an amount of the 17α-hydroxylase/$C_{17,20}$-lyase inhibitor or therapeutic agent effective for treating a disease or disorder disclosed herein, such as cancer.

As used herein and unless otherwise defined the phrase "refractory cancer," means cancer that is not responding to an anti-cancer treatment or cancer that is not responding sufficiently to an anti-cancer treatment. Refractory cancer can also include recurring or relapsing cancer.

As used herein and unless otherwise defined the phrase "refractory patient," means a patient who has refractory cancer.

As used herein and unless otherwise defined the phrase "relapse cancer," means cancer that was at one time responsive to an anti-cancer treatment but has become no longer responsive to such treatment or is no longer responding sufficiently to such treatment.

As used herein and unless otherwise defined the phrase "recurring cancer," means cancer that has returned after a patient has been earlier diagnosed with cancer, under gone treatment or had been previously diagnosed as cancer-free.

As used herein and unless otherwise defined the term "derivative" refers to a chemically modified compound wherein the chemical modification takes place at one or more functional groups of the compound. The derivative may retain or improve the pharmacological activity of the compound from which it is derived.

As used herein and unless otherwise defined the term "analog" refers to a chemical compound that is structurally similar to another but differs slightly in composition (as in the replacement of one atom by an atom of a different element or in the presence of a particular functional group).

As used herein and unless otherwise defined the phrase "pharmaceutically acceptable salt" refers to any salt of a 17α-hydroxylase/$C_{17, 20}$-lyase inhibitor which retains the biological effectiveness of the 17α-hydroxylase/$C_{17,20}$-lyase inhibitor. Examples of pharmaceutically acceptable salts include, but are not limited to, acetates, sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phylacetates, phenylpropionates, phenylbutyrates, citrates, lactates, gamma-hydroxybutyrates, glycollates, tartarates, alkanesulfonates (e.g. methane-sulfonate or mesylate), propanesulfonates, naphthalene-1-sulfonates, naphthalene-2-sulfonates, and mandelates. Several of the officially approved salts are listed in Remington: The Science and Practice of Pharmacy, Mack Publ. Co., Easton.

DETAILED DESCRIPTION OF THE INVENTION

The methods described herein for treating cancer comprise administering to a mammal, preferably a human, a 17α-hydroxylase/$C_{17, 20}$-lyase inhibitor in addition to at least one therapeutic agent, such as an anti-cancer agent or steroid, particularly a glucocorticoid. The compositions described herein comprise a 17α-hydroxylase/$C_{17, 20}$-lyase inhibitor and at least one additional therapeutic agent, such as an anti-cancer agent or steroid, particularly a corticosteroid or glucocorticoid. Other anti-cancer treatments such as, administration of yet another anti-cancer agent, radiotherapy, chemotherapy, photodynamic therapy, surgery or other immunotherapy, can be used with the methods and compositions.

17α-hydroxylase/$C_{17, 20}$-lyase Inhibitors

17α-hydroxylase/$C_{17, 20}$-lyase inhibitors have been shown to be useful in the treatment of cancer, specifically hormone-dependent disorders such as, androgen-dependent and estrogen-dependent disorders like prostate cancer and breast cancer respectively, as described in U.S. Pat. No. 5,604,213 to Barrie et al., which is herein incorporated by reference in its entirety.

In certain embodiments, the 17α-hydroxylase/$C_{17, 20}$-lyase inhibitor can be 17-(3-pyridyl)androsta-5,16-dien-3β-ol; 17-(3-pyridyl)androsta-3,5,16-triene; 17-(3-pyridyl)androsta-4,16-dien-3-one; 17-(3-pyridyl)estra-1,3,5[10],16-tetraen-3-ol; 17-(3-pyridyl)-5α-androst-16-en-3α-ol; 17-(3-pyridyl)-5α-androst-16-en-3-one; 17-(3-pyridyl)-androsta-4,16-diene-3,11-dione; 17-(3-pyridyl)-androsta-3,5,16-trien-3-ol; 6α- and 6β-fluoro-17-(3-pyridyl)androsta-4,16-dien-3-one 17-(3-pyridyl)androsta-4,16-dien-3,6-dione; 3α-trifluoromethyl-17-(3-pyridyl)androst-16-en-3β-ol or their acid addition salts and 3-esters as well as metabolites, analogs, derivatives or a pharmaceutically acceptable salt thereof.

In certain embodiments, the 17α-hydroxylase/$C_{17, 20}$-lyase inhibitor can have the structure of formula (I):

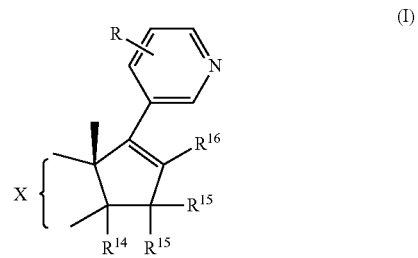

wherein X represents the residue of the A, B and C rings of a steroid which can be, without limitation, androstan-3α- or 3β-ol; androst-5-en-3α- or 3β-ol; androst-4-en-3-one; androst-2-ene; androst-4-ene; androst-5-ene; androsta-5,7-dien-3α or 3β-ol; androsta-1,4-dien-3-one; androsta-3,5-diene; androsta-3,5-diene-3-ol; estra-1,3,5[10]-triene; estra-1,3,5[10]-trien-3-ol; 5α-androstan-3-one; androst-4-ene-3,11-dione; 6-fluoroandrost-4-ene-3-one; or androstan-4-ene-3,6-dione; each of which, where structurally permissible, can be further derivatized in one or more of the following ways, including, but not limited to, to form 3-esters; to have one or more carbon or carbon ring double bonds in any of the 5,6-, 6,7-, 7,8-, 9,11- and 11,12-positions; as 3-oximes; as 3-methylenes; as 3-carboxylates; as 3-nitriles; as 3-nitros; as 3-desoxy derivatives; to have one or more hydroxy, halo, $C_{1-4}$-alkyl, trifluoro-methyl, $C_{1-4}$-alkoxy, $C_{1-4}$-alkanoyloxy, benzoyloxy, oxo, methylene or alkenyl substituents in the A, B, or C-ring; or to be 19-nor;

R represents a hydrogen atom or an alkyl group of 1-4 carbon atoms;

$R^{14}$ represents a hydrogen atom, a halogen atom or an alkyl group of 1 to 4 carbon atoms;

each of the $R^{15}$ substituents independently represents a hydrogen atom or an alkyl or alkoxy group of 1-4 carbon atoms, a hydroxy group or an alkylcarbonyloxy group of 2 to 5 carbon atoms or together represent an oxo or methylene group or $R^{14}$ and one of the $R^{15}$ groups together represent a double bond and the other $R^{15}$ group represents a hydrogen atom or an alkyl group of 1 to 4 carbon atoms; and $R^{16}$ represents a hydrogen atom, halogen atom, or an alkyl group of 1 to 4 carbon atoms, in the form of the free bases or pharmaceutically acceptable acid addition salts, but excluding 3β-acetoxy-17-(3-pyridyl)androsta-5,14,16-triene, 3β,15α- and 3β,15β-diacetoxy-17-(3-pyridyl)androsta-5,16-diene and 3β-methoxy-17-(3-pyridyl-5α-androst-16-ene. Suitable inhibitors also include metabolites, derivatives, analogs, or pharmaceutically acceptable salts of formula (I).

In another embodiment, the 17α-hydroxylase/$C_{17, 20}$-lyase inhibitor can have the structure of formula (I):

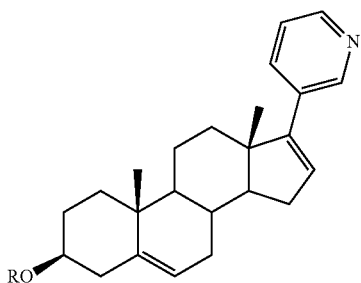

(I)

wherein R represents hydrogen or a lower acyl group having 1 to 4 carbons. Suitable inhibitors also include derivatives, analogs, or pharmaceutically acceptable salts of formula (I).

In still another embodiment, the 17α-hydroxylase/$C_{17,\ 20}$-lyase inhibitor can be a 3β-alkanoyloxy-17-(3-pyridyl) androsta-5,16-diene in which the alkanoyloxy group has from 2 to 4 carbon atoms.

In a preferred embodiment, the 17α-hydroxylase/$C_{17,\ 20}$-lyase inhibitor comprises abiraterone acetate or 3β-acetoxy-17-(3-pyridyl)androsta-5,16-diene which has the following structural formula:

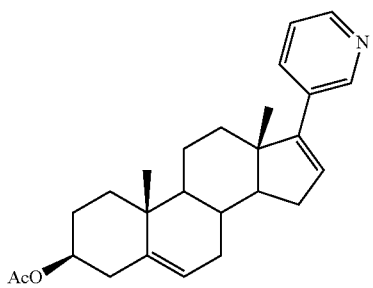

(II)

and pharmaceutically acceptable salts thereof.

Preferred salts of abiraterone acetate and methods of making such salts are also disclosed in U.S. Provisional Application No. 60/603,559 to Hunt, which is incorporated by reference in its entirety. Preferred salts include, but are not limited to, acetates, citrates, lactates, alkanesulfonates (e.g. methane-sulfonate or mesylate) and tartarates. Of special interest is the abiraterone acetate mesylate salt (i.e. 3β-acetoxy-17-(3-pyridyl)androsta-5,16-diene mesylate salt) which has the following structural formula:

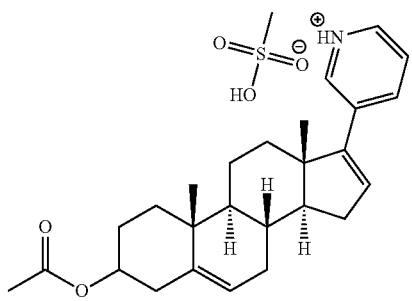

(III)

The 17α-hydroxylase/$C_{17,\ 20}$-lyase inhibitors can be made according to any method known to one skilled in the art. For example, such inhibitors can be synthesized according to the method disclosed in U.S. Pat. Nos. 5,604,213 and 5,618,807 to Barrie et al., herein incorporated by reference. Another method of making 17α-hydroxylase/$C_{17,\ 20}$-lyase inhibitors is disclosed in U.S. provisional application 60/603,558 to Bury, herein incorporated by reference.

The amount of 17α-hydroxylase/$C_{17,\ 20}$-lyase inhibitor administered to a mammal having cancer is an amount that is sufficient to treat the cancer, whether the 17α-hydroxylase/$C_{17,\ 20}$-lyase inhibitor is administered alone or in combination with an additional anti-cancer treatment, such as an additional anti-cancer agent.

Additional Therapeutic Agents

Suitable compounds that can be used in addition to 17α-hydroxylase/$C_{17,\ 20}$-lyase inhibitors as an anti-cancer agent include, but are not limited to, hormone ablation agents, anti-androgen agents, differentiating agents, anti-neoplastic agents, kinase inhibitors, anti-metabolite agents, alkylating agents, antibiotic agents, immunological agents, interferon-type agents, intercalating agents, growth factor inhibitors, cell cycle inhibitors, enzymes, topoisomerase inhibitors, biological response modifiers, mitotic inhibitors, matrix metalloprotease inhibitors, genetic therapeutics, and anti-androgens. The amount of the additional anti-cancer agent administered to a mammal having cancer is an amount that is sufficient to treat the cancer whether administered alone or in combination with a 17α-hydroxylase/$C_{17,\ 20}$-lyase inhibitor. Below are lists of examples of some of the above classes of anti-cancer agents. The examples are not all inclusive and are for purposes of illustration and not for purposes of limitation. Many of the examples below could be listed in multiple classes of anti-cancer agents and are not restricted in any way to the class in which they are listed in.

Suitable hormonal ablation agents include, but are not limited to, androgen ablation agents and estrogen ablation agents. In preferred embodiments, the 17α-hydroxylase/$C_{17,\ 20}$-lyase inhibitor is administered with a hormonal ablation agent, such as deslorelin, leuprolide, goserelin or triptorelin. Even though throughout this specification and in the claims the phrase "hormonal ablation agent" is written as a singular noun, for example; "a hormonal ablation agent" or "the hormonal ablation agent," the phrase "hormonal ablation agent" should not be interpreted as being limited to the inclusion of a single hormonal ablation agent. The amount of the hormonal ablation agent administered to a mammal having cancer is an amount that is sufficient to treat the cancer whether administered alone or in combination with a 17α-hydroxylase/$C_{17,\ 20}$-lyase inhibitor.

Suitable anti-androgen agents include but are not limited to bicalutamide, flutamide and nilutamide. The amount of the anti-androgen agent administered to a mammal having cancer is an amount that is sufficient to treat the cancer whether administered alone or in combination with a 17α-hydroxylase/$C_{17,\ 20}$-lyase inhibitor.

In another embodiment, the 17α-hydroxylase/$C_{17,\ 20}$-lyase inhibitor may be administered with a differentiating agent. Suitable differentiating agents include, but are not limited to, polyamine inhibitors; vitamin D and its analogs, such as, calcitriol, doxercalciferol and seocalcitol; metabolites of vitamin A, such as, ATRA, retinoic acid, retinoids; short-chain fatty acids; phenylbutyrate; and nonsteroidal anti-inflammatory agents. The amount of the differentiating agent administered to a mammal having cancer is an amount that is sufficient to treat the cancer whether administered alone or in combination with a 17α-hydroxylase/$C_{17,\ 20}$-lyase inhibitor.

In another preferred embodiment, the 17α-hydroxylase/$C_{17, 20}$-lyase inhibitor may be administered with an antineoplastic agent, including, but not limited to, tubulin interacting agents, topoisomerase inhibitors and agents, acitretin, alstonine, amonafide, amphethinile, amsacrine, ankinomycin, anti-neoplaston, aphidicolin glycinate, asparaginase, baccharin, batracylin, benfluron, benzotript, bromofosfamide, caracemide, carmethizole hydrochloride, chlorsulfaquinoxalone, clanfenur, claviridenone, crisnatol, curaderm, cytarabine, cytocytin, dacarbazine, datelliptinium, dihaematoporphyrin ether, dihydrolenperone, dinaline, distamycin, docetaxel, elliprabin, elliptinium acetate, epothilones, ergotamine, etoposide, etretinate, fenretinide, gallium nitrate, genkwadaphnin, hexadecylphosphocholine, homoharringtonine, hydroxyurea, ilmofosine, isoglutamine, isotretinoin, leukoregulin, lonidamine, merbarone, merocyanlne derivatives, methylanilinoacridine, minactivin, mitonafide, mitoquidone, mitoxantrone, mopidamol, motretinide, N-(retinoyl)amino acids, N-acylated-dehydroalanines, nafazatrom, nocodazole derivative, ocreotide, oquizanocinc, paclitaxel, pancratistatin, pazelliptine, piroxantrone, polyhaematoporphyrin, polypreic acid, probimane, procarbazine, proglumide, razoxane, retelliptine, spatol, spirocyclopropane derivatives, spirogermanium, strypoldinone, superoxide dismutase, teniposide, thaliblastine, tocotrienol, topotecan, ukrain, vinblastine sulfate, vincristine, vindesine, vinestramide, vinorelbine, vintriptol, vinzolidine, and withanolides. The amount of the anti-neoplastic agent administered to a mammal having cancer is an amount that is sufficient to treat the cancer whether administered alone or in combination with a 17α-hydroxylase/$C_{17, 20}$-lyase inhibitor.

The 17α-hydroxylase/$C_{17, 20}$-lyase inhibitors may also be used with a kinase inhibitor including p38 inhibitors and CDK inhibitors, TNF inhibitors, metallomatrix proteases inhibitors (MMP), COX-2 inhibitors including celecoxib, rofecoxib, parecoxib, valdecoxib, and etoricoxib, SOD mimics or $α_v β_3$ inhibitors. The amount of the kinase inhibitor administered to a mammal having cancer is an amount that is sufficient to treat the cancer whether administered alone or in combination with a 17α-hydroxylase/$C_{17, 20}$-lyase inhibitor.

In another embodiment, the 17α-hydroxylase/$C_{17, 20}$-lyase inhibitor may be administered with an anti-metabolite agent. Suitable anti-metabolite agents may be selected from, but not limited to, 5-FU-fibrinogen, acanthifolic acid, aminothiadiazole, brequinar sodium, carmofur, cyclopentyl cytosine, cytarabine phosphate stearate, cytarabine conjugates, dezaguanine, dideoxycytidine, dideoxyguanosine, didox, doxifluridine, fazarabine, floxuridine, fludarabine phosphate, 5-fluorouracil, N-(2'-furanidyl)-5-fluorouracil, isopropyl pyrrolizine, methobenzaprim, methotrexate, norspermidine, pentostatin, piritrexim, plicamycin, thioguanine, tiazofurin, trimetrexate, tyrosine kinase inhibitors, and uricytin. The amount of the anti-metabolite agent administered to a mammal having cancer is an amount that is sufficient to treat the cancer whether administered alone or in combination with a 17α-hydroxylase/$C_{17, 20}$-lyase inhibitor.

In another embodiment, the 17α-hydroxylase/$C_{17, 20}$-lyase inhibitor may be administered with an alkylating agent. Suitable alkylating agents may be selected from, but not limited to, aldo-phosphamide analogues, altretamine, anaxirone, bestrabucil, budotitane, carboplatin, carmustine, chlorambucil, cisplatin, cyclophosphamide, cyplatate, diphenylspiromustine, diplatinum cytostatic, elmustine, estramustine phosphate sodium, fotemustine, hepsul-fam, ifosfamide, iproplatin, lomustine, mafosfamide, mitolactol, oxaliplatin, prednimustine, ranimustine, semustine, spiromustine, tauromustine, temozolomide, teroxirone, tetraplatin and trimelamol. The amount of the alkylating agent administered to a mammal having cancer is an amount that is sufficient to treat the cancer whether administered alone or in combination with a 17α-hydroxylase/$C_{17, 20}$-lyase inhibitor.

In another preferred embodiment, the 17α-hydroxylase/$C_{17, 20}$-lyase inhibitor may be administered with an antibiotic agent. Suitable antibiotic agents may be selected from, but not limited to, aclarubicin, actinomycin D, actinoplanone, adriamycin, aeroplysinin derivative, amrubicin, anthracycline, azino-mycin-A, bisucaberin, bleomycin sulfate, bryostatin-1, calichemycin, chromoximycin, dactinomycin, daunorubicin, ditrisarubicin B, dexamethasone, doxorubicin, doxorubicin-fibrinogen, elsamicin-A, epirubicin, erbstatin, esorubicin, esperamicin-Al, esperamicin-Alb, fostriecin, glidobactin, gregatin-A, grincamycin, herbimycin, corticosteroids such as hydrocortisone, idarubicin, illudins, kazusamycin, kesarirhodins, menogaril, mitomycin, neoenactin, oxalysine, oxaunomycin, peplomycin, pilatin, pirarubicin, porothramycin, prednisone, prednisolone, pyrindanycin A, rapamycin, rhizoxin, rodorubicin, sibanomicin, siwenmycin, sorangicin-A, sparsomycin, talisomycin, terpentecin, thrazine, tricrozarin A, and zorubicin. The amount of the antibiotic agent administered to a mammal having cancer is an amount that is sufficient to treat the cancer whether administered alone or in combination with a 17α-hydroxylase/$C_{17, 20}$-lyase inhibitor.

Alternatively, the 17α-hydroxylase/$C_{17, 20}$-lyase inhibitors may also be used with other anti-cancer agents, including but not limited to, acemannan, aclarubicin, aldesleukin, alemtuzumab, alitretinoin, altretamine, amifostine, amsacrine, anagrelide, anastrozole, ancestim, bexarotene, broxuridine, capecitabine, celmoleukin, cetrorelix, cladribine, clotrimazole, daclizumab, dexrazoxane, dilazep, docosanol, doxifluridine, bromocriptine, carmustine, cytarabine, diclofenac, edelfosine, edrecolomab, eflornithine, emitefur, exemestane, exisulind, fadrozole, filgrastim, finasteride, fludarabine phosphate, formestane, fotemustine, gallium nitrate, gemcitabine, glycopine, heptaplatin, ibandronic acid, imiquimod, iobenguane, irinotecan, irsogladine, lanreotide, leflunomide, lenograstim, lentinan sulfate, letrozole, liarozole, lobaplatin, lonidamine, masoprocol, melarsoprol, metoclopramide, mifepristone, miltefosine, mirimostim, mitoguazone, mitolactol, molgramostim, nafarelin, nartograstim, nedaplatin, nilutamide, noscapine, oprelvekin, osaterone, oxaliplatin, pamidronic acid, pegaspargase, pentosan polysulfate sodium, pentostatin, picibanil, pirarubicin, porfimer sodium, raloxifene, raltitrexed, rasburicase, rituximab, romurtide, sargramostim, sizofiran, sobuzoxane, sonermin, suramin, tasonermin, tazarotene, tegafur, temoporfin, temozolomide, teniposide, tetrachlorodecaoxide, thalidomide, thymalfasin, thyrotropin alfa, topotecan, toremifene, trastuzumab, treosulfan, tretinoin, trilostane, trimetrexate, ubenimex, valrubicin, verteporfin, vinorelbine. The amount of the anti-cancer agent administered to a mammal having cancer is an amount that is sufficient to treat the cancer whether administered alone or in combination with a 17α-hydroxylase/$C_{17, 20}$-lyase inhibitor.

The 17α-hydroxylase/$C_{17, 20}$-lyase inhibitors may also be administered or combined with steroids, such as corticosteroids or glucocorticoids. The 17α-hydroxylase/$C_{17,20}$-lyase inhibitors and the steroid may be administered in the same or in different compositions. Non-limiting examples of suitable steroids include hydrocortisone, prednisone, or dexamethasone. The amount of the steroid administered to a mammal having cancer is an amount that is sufficient to treat the cancer whether administered alone or in combination with a 17α-hydroxylase/$C_{17, 20}$-lyase inhibitor.

In one embodiment, provided herein are methods and compositions comprising both abiraterone acetate and a steroid particularly a corticosteroid, or more particularly a glucocorticoid. Steroids within the scope of the disclosure include, but are not limited to, (1) hydrocortisone (cortisol; cyprionate (e.g., CORTEF), oral; sodium phosphate injection (HYDROCORTONE PHOSPHATE); sodium succinate (e.g., A-HYDROCORT, Solu-CORTEF); cortisone acetate oral or injection forms, etc.), (2) dexamethasone (e.g., Decadron, oral; Decadron-LA injection, etc.), (3) prednisolone (e.g., Delta-CORTEF, prednisolone acetate (ECONO-PRED), prednisolone sodium phosphate (HYDELTRA-SOL), prednisolone tebutate (HYDELTRA-TBA, etc.)), or (4) prednisone DELTASONE, etc.) and combinations thereof. See, e.g., GOODMAN & GILMAN'S THE PHARMACOLOGICAL BASIS OF THERAPEUTICS, $10^{TH}$ EDITION 2001.

In a specific embodiment, single unit solid oral dosage forms which comprise an amount from about 50 mg to about 300 mg of abiraterone acetate and an amount from about 0.5 mg to about 3.0 mg of a steroid, e.g., glucocorticoid in a single composition, optionally with excipients, carriers, diluents, etc. is contemplated. For instance, the single unit dosage form can comprise about 250 mg of abiraterone acetate and about 1.0 mg, 1.25 mg, 1.5 mg, or 2.0 mg of a steroid, such as but not limited to corticosteroids or glucocorticoids.

Administration of the 17α-hydroxylase/$C_{17, 20}$-lyase Inhibitor and an Additional Therapeutic Agent The 17α-hydroxylase/$C_{17, 20}$-lyase inhibitor and the additional therapeutic agent, such as an anti-cancer agent or a steroid can be administered by any method known to one skilled in the art. In certain embodiments, the 17α-hydroxylase/$C_{17, 20}$-lyase inhibitor and the additional therapeutic agent can be in separate compositions prior to administration. In the alternative, the 17α-hydroxylase/$C_{17, 20}$-lyase inhibitor and the additional therapeutic agent can be combined into a single composition for administration.

The 17α-hydroxylase/$C_{17, 20}$-lyase inhibitor and the additional therapeutic agent can be administered sequentially or simultaneously. If administered sequentially, the order of administration is flexible. For instance, 17α-hydroxylase/$C_{17, 20}$-lyase inhibitor acetate can be administered prior to administration of the additional therapeutic agent. Alternatively, administration of the additional therapeutic agent can precede administration of 17α-hydroxylase/$C_{17, 20}$-lyase inhibitor.

Whether they are administered as separate compositions or in one composition, each composition is preferably pharmaceutically suitable for administration. Moreover, the 17α-hydroxylase/$C_{17, 20}$-lyase inhibitor and the therapeutic agent, if administered separately, can be administered by the same or different modes of administration. Examples of modes of administration include parenteral (e.g., subcutaneous, intramuscular, intraorbital, intracapsular, intraspinal, intrasternal, intravenous, intradermal, intraperitoneal, intraportal, intra-arterial, intrathecal, transmucosal, intra-articular, and intrapleural,), transdermal (e.g., topical), epidural, and mucosal (e.g., intranasal) injection or infusion, as well as oral, inhalation, pulmonary, and rectal administration. In specific embodiments, both are oral.

For example, the 17α-hydroxylase/$C_{17, 20}$-lyase inhibitor can be administered transdermally and the additional therapeutic agent can be administered parenterally. Alternatively, the 17α-hydroxylase/$C_{17, 20}$-lyase inhibitor can be administered orally, such as in a tablet, caplet or capsule, while the additional therapeutic agent can be administered intravenously. Such intravenous administered therapeutic agents include, but are not limited to, docetaxel injections, such as Taxotere®; paclitaxel injections, such as Paclitaxel® and mitoxantrone injections, such as Novantrone. Also, the additional therapeutic agent can be in the form of depots or implants such as leuprolide depots and implants, e.g. Viadur® and Lupron Depot®; triptorelin depots, e.g. Trelstar®; goserelin implants, e.g. Zoladex®.

The suitable daily dosage of the 17α-hydroxylase/$C_{17, 20}$-lyase inhibitor depends upon a number of factors, including, the nature of the severity of the condition to be treated, the particular inhibitor, the route of administration and the age, weight, and response of the individual patient. Suitable daily dosages of 17α-hydroxylase/$C_{17, 20}$-lyase inhibitors can generally range from about 0.0001 mg/kg/day to about 1000 mg/kg/day, or from about 0.001 mg/kg/day to about 200 mg/kg/day, or from about 0.01 mg/kg/day to about 200 mg/kg/day, or from about 0.01 mg/kg/day to about 100 mg/kg/day in single or multiple doses.

In some embodiments, the 17α-hydroxylase/$C_{17, 20}$-lyase inhibitor can be administered in an amount from about 0.004 mg/day to about 5,000 mg/day, or from about 0.04 mg/day to about 3,000 mg/day, or from about 0.4 mg/day to about 1500 mg/day. In certain embodiments, the 17α-hydroxylase/$C_{17, 20}$-lyase inhibitor can be administered in an amount from about 0.1 mg/day to about 2000 mg/day or from about 1 mg/day to about 2000 mg/day or from about 50 mg/day to about 2000 mg/day or from about 100 mg/day to about 1500 mg/day or from about 5 mg/day to about 1,000 mg/day or from about 5 mg/day to about 900 mg/day or from about 10 mg/day to about 800 mg/day or from about 15 mg/day to about 700 mg/day or from about 20 mg/day to about 600 mg/day or from about 25 mg/day to about 500 mg/day in single or multiple doses.

In certain embodiments, the 17α-hydroxylase/$C_{17, 20}$-lyase inhibitor is co-administered with an additional anti-cancer agent such as mitoxantrone, paclitaxel or docetaxel. For example, a method for the treatment of a cancer in a mammal comprises administering an amount of abiraterone acetate and an amount of mitoxantrone. For example, the abiraterone acetate can be administered in an amount of about 0.01 mg/kg/day to about 100 mg/kg/day and the mitoxantrone can be administered in an amount of about 0.1 mg/m$^2$ to about 20 mg/m$^2$. Preferably, the mitoxantrone is administered over a period of between about 10 to about 20 minutes once every 21 days.

Also, a method for the treatment of a cancer in a mammal can comprise administering an amount of abiraterone acetate and an amount of paclitaxel. In one embodiment, the abiraterone acetate can be administered in an amount of about 0.01 mg/kg/day to about 100 mg/kg/day and the paclitaxel can be administered in the amount of about 1 mg/m$^2$ to about 175 mg/m$^2$. Preferably, the paclitaxel is administered over a period of between about 2 to about 5 hours once every three months.

Additionally, a method for the treatment of a cancer in a mammal comprises administering an amount of abiraterone acetate and an amount of docetaxel. For example, the abiraterone acetate can be administered in an amount of about 0.01 mg/kg/day to about 100 mg/kg/day and the docetaxel can be administered in an amount of about 1 mg/m$^2$ to about 100 mg/m$^2$. Preferably, the docetaxel is administered over a period of between about 1 to about 2 hours once every three weeks.

In certain embodiments, the 17α-hydroxylase/$C_{17,\,20}$-lyase inhibitor is administered along with an anticancer agent that comprises a hormonal ablation agent, including, but not limited to, leuprolide, goserelin, or triptorelin. For example, one method for the treatment of a cancer in a mammal also comprises administering an amount of abiraterone acetate and an amount of leuprolide. The amount of abiraterone acetate can be about 0.01 mg/kg/day to about 100 mg/kg/day and the amount of leuprolide can be about 0.01 mg to about 200 mg over a period of about 3 days to about 12 months. Preferably, the leuprolide is administered in the amount of about 3.6 mg of leuprolide over a period of about 3 days to about 12 months.

Additionally, the methods for the treatment of cancer in a mammal include administering an amount of abiraterone acetate and an amount of goserelin. For example, the amount of abiraterone acetate can be about 0.01 mg/kg/day to about 100 mg/kg/day and the amount of goserelin can be about 0.01 mg to about 20 mg over a period of about 28 days to about 3 months. Preferably, the goserelin is administered in the amount of about 3.6 mg to about 10.8 mg over a period of about 28 days to about 3 months.

In certain embodiments the methods for the treatment of cancer in a mammal comprises administering an amount of abiraterone acetate and an amount of triptorelin. For example, the amount of abiraterone acetate can be about 0.01 mg/kg/day to about 100 mg/kg/day and the amount of triptorelin can be about 0.01 mg to about 20 mg, over a period of about 1 month, preferably the triptorelin is administered in the amount of about 3.75 mg over a period of about 1 month.

Also, in one embodiment, the method for the treatment of a cancer in a mammal comprises administering an amount of abiraterone acetate and an amount of seocalcitol. For instance, the method involves administering an amount of about 0.01 mg/kg/day to about 100 mg/kg/day of abiraterone acetate and an amount of about 0.1 μg/day to about 500 μg/day of seocalcitol, such as about 100 μg/day of seocalcitol.

In another embodiment, the method for the treatment of a cancer in a mammal comprises administering an amount of abiraterone acetate and an amount of bicalutamide. For instance, the method involves administering an amount of about 0.01 mg/kg/day to about 100 mg/kg/day of abiraterone acetate and an amount of about 1 mg/day to about 300 mg/day of bicalutamide.

In yet another embodiment, the method for the treatment of a cancer in a mammal comprises administering an amount of abiraterone acetate and an amount of flutamide. For example, the method comprises administering an amount of about 0.01 mg/kg/day to about 100 mg/kg/day of abiraterone acetate and an amount of about 1 mg/day to about 2000 mg/day of flutamide.

Moreover, the method for the treatment of a cancer in a mammal can comprise administering an amount of a 17α-hydroxylase/$C_{17,\,20}$-lyase inhibitor such as abiraterone acetate and an amount of a glucocorticoid including, but not limited to, hydrocortisone, prednisone or dexamethasone. For example, the method can comprise administering an amount of about 50 mg/day to about 2000 mg/day of abiraterone acetate and an amount of about 0.01 mg/day to about 500 mg/day of hydrocortisone. In other instances, the method can comprise administering an amount of about 500 mg/day to about 1500 mg/day of abiraterone acetate and an amount of about 10 mg/day to about 250 mg/day of hydrocortisone.

The method for the treatment of a cancer can also comprise administering an amount of a 17α-hydroxylase/$C_{17,\,20}$-lyase inhibitor, such as abiraterone acetate, and an amount of a glucocorticoid, such as prednisone. For example, the method can comprise administering an amount of about 50 mg/day to about 2000 mg/day of abiraterone acetate and an amount of about 0.01 mg/day to about 500 mg/day of prednisone. Also, the method can comprise administering an amount of about 500 mg/day to about 1500 mg/day of abiraterone acetate and an amount of about 10 mg/day to about 250 mg/day of prednisone.

In addition, the method for the treatment of a cancer can also comprise administering an amount of a 17α-hydroxylase/$C_{17,\,20}$-lyase inhibitor, such as abiraterone acetate, and an amount of a glucocorticoid, such as dexamethasone. For example, the method can comprise administering an amount of about 50 mg/day to about 2000 mg/day of abiraterone acetate and an amount of about 0.01 mg/day to about 500 mg/day of dexamethasone. Also, the method can comprise administering an amount of about 500 mg/day to about 1500 mg/day of abiraterone acetate and an amount of about 0.5 mg/day to about 25 mg/day of dexamethasone.

Compositions Containing a 17α-hydroxylase/$C_{17,20}$-Lyase Inhibitor and an Additional Therapeutic Agent In certain embodiments, the compositions can contain a combination of a 17α-hydroxylase/$C_{17,\,20}$-lyase inhibitor, preferably abiraterone acetate, and any of the therapeutic agents recited above. Whether the 17α-hydroxylase/$C_{17,\,20}$-lyase inhibitor and the additional therapeutic agent are administered in separate compositions or as a single composition, the compositions can take various forms. For example, the compositions can take the form of solutions, suspensions, emulsions, tablets, pills, capsules, powders or sustained-release formulations, depending on the intended route of administration.

For topical or transdermal administration, the compositions can be formulated as solutions, gels, ointments, creams, suspensions or salves.

For oral administration, the compositions may be formulated as tablets, pills, dragees, troches, capsules, liquids, gels, syrups, slurries, suspensions and the like, for oral ingestion by a patient to be treated.

The composition may also be formulated in rectal or vaginal compositions such as suppositories or retention enemas that contain conventional suppository bases such as cocoa butter or other glycerides.

In addition to the formulations described previously, the composition may also be formulated as a depot preparation. Such long acting formulations may be administered by implantation (for example subcutaneously or intramuscularly) or by intramuscular injection. Thus, for example, the therapeutic agents may be formulated with suitable polymeric or hydrophobic materials (for example as an emulsion in an acceptable oil) or ion exchange resins, or as sparingly soluble derivatives, for example, as a sparingly soluble salt.

Additionally, the composition may be delivered using a sustained-release system, such as semi-permeable matrices of solid polymers containing the composition. Various forms of sustained-release materials have been established and are well known by those skilled in the art. Sustained-release capsules may, depending on their chemical nature can release the composition over a period of hours, days, weeks, months. For example a sustained release capsule can release the compositions over a period of 100 days or longer. Depending on the chemical nature and the biological stability of the composition, additional strategies for stabilization may be employed.

The compositions can further comprise a pharmaceutically acceptable carrier. The term "carrier" refers to a diluent, adjuvant (e.g., Freund's adjuvant (complete and incomplete)), excipient, or vehicle with which the therapeutic is administered.

For parenteral administrations, the composition can comprise one or more of the following carriers: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium hi sulfite; chelating agents such as ethylenediaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

For oral solid formulations suitable carriers include fillers such as sugars, e.g., lactose, sucrose, mannitol and sorbitol; cellulose preparations such as maize starch, wheat starch, rice starch, potato starch, gelatin, gum tragacanth, methyl cellulose, hydroxypropylmethyl-cellulose, sodium carboxymethylcellulose, fats and oils; granulating agents; and binding agents such as microcrystalline cellulose, gum tragacanth or gelatin; disintegrating agents, such as cross-linked polyvinylpyrrolidone, agar, or alginic acid or a salt thereof such as sodium alginate, Primogel, or corn starch; lubricants, such as magnesium stearate or Sterotes; glidants, such as colloidal silicon dioxide; a sweetening agent, such as sucrose or saccharin; or flavoring agents, such as peppetinint, methyl salicylate, or orange flavoring. If desired, solid dosage forms may be sugar-coated or enteric-coated using standard techniques.

For intravenous administration, suitable carriers include physiological saline, bacteriostatic water, phosphate buffered saline (PBS). In all cases, the composition must be sterile and should be fluid to the extent that easy injectability with a syringe. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars; polyalcohols such as mannitol, sorbitol; sodium chloride in the composition. Prolonged absorption of the injectable compositions can be brought about by including in the composition an agent which delays absorption, for example, aluminum monostearate and gelatin.

Also for intravenous administration, the compositions may be formulated in solutions, preferably in physiologically compatible buffers such as Hanks's solution, Ringer's solution, or physiological saline buffer. The solution may contain formulatory agents such as suspending, stabilizing and/or dispersing agents. In a preferred embodiment, the compositions are formulated in sterile solutions.

For transmucosal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories.

For administration by inhalation, the compositions may be formulated as an aerosol spray from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges of gelatin for use in an inhaler or insufflator may be formulated containing a powder mix of the composition and a suitable powder base such as lactose or starch.

The pharmaceutical compositions may be manufactured by means of conventional mixing, dissolving, granulating, dragee-making, levigating, emulsifying, encapsulating, entrapping or lyophilizing processes.

One example of a composition comprising a 17α-hydroxylase/$C_{17, 20}$-lyase inhibitor and an additional therapeutic agent is an oral composition or composition suitable for oral administration comprising abiraterone acetate in combination with a steroid. For example, the oral composition can be a solid dosage form such as a pill, a tablet or a capsule. The oral composition can comprise about 10 mg, 25 mg, 50 mg, 75 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, or 1000 mg of abiraterone acetate. The oral composition comprises about 0.25 mg, 0.5 mg, 0.75 mg, 1.0 mg, 1.25 mg, 1.5 mg, 1.75 mg, 2.0 mg, 2.25 mg, 2.5 mg, 2.75 mg, 3.0 mg, 3.25 mg, 3.5 mg, 3.75 mg, 4.0 mg, 4.25 mg, 4.5 mg, 4.75 mg, 5.0 mg, 7.5 mg, 10 mg, 20 mg, 30 mg, 40 mg or 50 mg of a steroid, such as a glucocorticoid.

In one embodiment, the oral composition can comprise about 50 mg to about 500 mg of abiraterone acetate and an amount of about 0.25 mg to about 3.5 mg of the steroid, such as hydrocortisone, prednisone or dexamethasone. In other instances, the composition can comprise about 50 mg to about 300 mg of abiraterone acetate and an amount of about 1.0 mg to about 2.5 mg of the steroid, such as hydrocortisone, prednisone or dexamethasone. In another embodiment the composition can comprise about 50 mg to about 300 mg of abiraterone acetate and about 0.5 mg to about 3.0 mg of a steroid. For example, the oral composition can be a tablet containing 250 mg of abiraterone acetate; 1.25 mg or 2.0 mg of a steroid, such as hydrocortisone, prednisone or dexamethasone; and one or more carriers, excipients, diluents or additional ingredients. Additionally, the oral composition can be a capsule containing 250 mg of abiraterone acetate; 1.25 mg or 2.0 mg of a steroid, such as hydrocortisone, prednisone or dexamethasone; and one or more carriers, excipients, diluents or additional ingredients.

The description contained herein is for purposes of illustration and not for purposes of limitation. The methods and compositions described herein can comprise any feature described herein either alone or in combination with any other feature(s) described herein. Changes and modifications may be made to the embodiments of the description. Furthermore, obvious changes, modifications or variations will occur to those skilled in the art. Also, all references cited above are incorporated herein, in their entirety, for all purposes related to this disclosure.

What is claimed is:

1. A method for the treatment of a refractory prostate cancer in a human comprising administering to said human a therapeutically effective amount of at least two anti-cancer agents, wherein the at least two anti-cancer agents are:
（a) abiraterone acetate or a pharmaceutically acceptable salt thereof, and
(b) a prednisolone.

2. The method of claim 1, wherein the therapeutically effective amount of the abiraterone acetate or pharmaceutically acceptable salt thereof is from about 500 mg/day to about 1500 mg/day.

3. The method of claim 2, wherein the therapeutically effective amount of the prednisolone is from about 0.25 mg/day to about 50 mg/day.

4. The method of claim 2, wherein the therapeutically effective amount of the prednisolone is from about 5 mg/day to about 10 mg/day.

5. The method of claim 4, wherein the therapeutically effective amount of the prednisolone is about 10 mg/day.

6. The method of claim 1, wherein the prednisolone is selected from prednisolone acetate, prednisolone sodium phosphate, and prednisolone tebutate.

7. The method of claim 1, wherein the refractory prostate cancer is metastatic refractory prostate cancer.

8. The method of claim 1, wherein the amount of the prednisolone is effective to enhance the response of the refractory prostate cancer to abiraterone acetate or a pharmaceutically acceptable salt thereof.

9. The method of claim 1, wherein the amount of the prednisolone is effective to reduce the resistance of the refractory prostate cancer to abiraterone acetate or a pharmaceutically acceptable salt thereof.

* * * * *